(12) United States Patent
Stulen et al.

(10) Patent No.: US 12,426,913 B2
(45) Date of Patent: Sep. 30, 2025

(54) SURGICAL INSTRUMENTS WITH ARTICULATING SHAFTS

(71) Applicant: Cilag GmbH International, Zug (CH)

(72) Inventors: Foster B. Stulen, Johns Island, SC (US); Zhifan F. Huang, Mason, OH (US); Patrick A. Weizman, Liberty Township, OH (US); Steven P. Smolik, West Chester, OH (US); Carl J. Draginoff, Jr., Mason, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/411,741

(22) Filed: Jan. 12, 2024

(65) Prior Publication Data

US 2024/0268853 A1    Aug. 15, 2024

Related U.S. Application Data

(62) Division of application No. 16/233,911, filed on Dec. 27, 2018, now Pat. No. 11,871,955, which is a
(Continued)

(51) Int. Cl.
*A61B 17/32* (2006.01)
*A61B 17/22* (2006.01)
(Continued)

(52) U.S. Cl.
CPC ...... *A61B 17/320092* (2013.01); *A61B 17/29* (2013.01); *A61B 17/320016* (2013.01);
(Continued)

(58) Field of Classification Search
CPC .................. A61B 17/320016; A61B 17/320068–17/320092;
(Continued)

(56) References Cited

U.S. PATENT DOCUMENTS 5,203,380 A   4/1993   Chikama
5,269,297 A   12/1993  Weng et al.
(Continued)

FOREIGN PATENT DOCUMENTS

JP   H0833644 A      2/1996
JP   2008017876 A    1/2008
JP   200833644 A     2/2008

*Primary Examiner* — Kathleen S Holwerda

(57) ABSTRACT

Various embodiments are directed to articulatable surgical instruments. Some embodiments comprise an end effector to treat tissue, where the end effector comprises an ultrasonic blade. A hollow shaft may extend proximally from the end effector along a longitudinal axis. A waveguide may extend through the shaft and may be acoustically coupled to the ultrasonic blade. The waveguide may comprise a distally positioned flange positioned within the hollow shaft proximally from the blade and may be held stationary at a first pivot point positioned within the hollow shaft proximally from the flange. A reciprocating wedge may be positioned within the hollow shaft such that distal motion of the wedge pushes the wedge between the flange and the hollow shaft, causing the ultrasonic blade to pivot about the first pivot point in a first direction.

17 Claims, 71 Drawing Sheets

Related U.S. Application Data division of application No. 15/212,742, filed on Jul. 18, 2016, now Pat. No. 10,335,182, which is a division of application No. 13/538,700, filed on Jun. 29, 2012, now Pat. No. 9,408,622.

(51) Int. Cl.
*A61B 17/29* (2006.01)
*A61B 18/14* (2006.01)
*A61B 34/30* (2016.01)
*A61B 17/00* (2006.01)
*A61B 18/00* (2006.01)

(52) U.S. Cl.
CPC .......... *A61B 18/1447* (2013.01); *A61B 34/30* (2016.02); *A61B 2017/003* (2013.01); *A61B 2017/00398* (2013.01); *A61B 2017/22015* (2013.01); *A61B 2017/22018* (2013.01); *A61B 2017/2927* (2013.01); *A61B 2017/2932* (2013.01); *A61B 2017/294* (2013.01); *A61B 2017/320069* (2017.08); *A61B 2017/320071* (2017.08); *A61B 2017/320075* (2017.08); *A61B 2017/320078* (2017.08); *A61B 2017/320089* (2017.08); *A61B 2017/320093* (2017.08); *A61B 2017/320094* (2017.08); *A61B 2017/320095* (2017.08); *A61B 2018/00196* (2013.01); *A61B 2018/00589* (2013.01); *A61B 2018/00595* (2013.01); *A61B 2018/00607* (2013.01); *A61B 2018/0063* (2013.01); *A61B 2018/00642* (2013.01); *A61B 2018/00702* (2013.01); *A61B 2018/00875* (2013.01); *A61B 2018/0091* (2013.01); *A61B 2018/00994* (2013.01); *A61B 2018/1452* (2013.01)

(58) Field of Classification Search
CPC ........... A61B 2017/320071; A61B 2017/2927; A61B 17/32009; A61B 2017/320072; A61B 2017/320073; A61B 2017/32074; A61B 2017/320093; A61B 2017/320094
See application file for complete search history.

(56) References Cited

U.S. PATENT DOCUMENTS

| | | | |
|---|---|---|---|
| 5,549,637 A | | 8/1996 | Crainich |
| 5,649,955 A | | 7/1997 | Hashimoto et al. |
| 5,704,534 A | | 1/1998 | Huitema et al. |
| 5,792,135 A | | 8/1998 | Madhani et al. |
| 5,817,084 A | | 10/1998 | Jensen |
| 5,878,193 A | | 3/1999 | Wang et al. |
| 5,897,523 A | * | 4/1999 | Wright ........... A61B 17/320068 600/459 |
| 6,063,098 A | | 5/2000 | Houser et al. |
| 6,132,368 A | | 10/2000 | Cooper |
| 6,231,565 B1 | | 5/2001 | Tovey et al. |
| 6,364,888 B1 | | 4/2002 | Niemeyer et al. |
| 6,390,973 B1 | | 5/2002 | Ouchi |
| 6,454,782 B1 | * | 9/2002 | Schwemberger ........................... A61B 17/320068 606/174 |
| 6,480,796 B2 | | 11/2002 | Wiener |
| 6,500,312 B2 | | 12/2002 | Wedekamp |
| 6,533,784 B2 | | 3/2003 | Truckai et al. |
| 6,537,291 B2 | | 3/2003 | Friedman et al. |
| 6,589,200 B1 | | 7/2003 | Schwemberger et al. |
| 6,656,177 B2 | | 12/2003 | Truckai et al. |
| 6,662,127 B2 | | 12/2003 | Wiener et al. |
| 6,679,899 B2 | | 1/2004 | Wiener et al. |
| 6,752,815 B2 | | 6/2004 | Beaupre |
| 6,770,072 B1 | | 8/2004 | Truckai et al. |
| 6,773,409 B2 | | 8/2004 | Truckai et al. |
| 6,783,524 B2 | | 8/2004 | Anderson et al. |
| 6,802,843 B2 | | 10/2004 | Truckai et al. |
| 6,905,497 B2 | | 6/2005 | Truckai et al. |
| 6,913,579 B2 | | 7/2005 | Truckai et al. |
| 6,926,716 B2 | | 8/2005 | Baker et al. |
| 6,929,644 B2 | | 8/2005 | Truckai et al. |
| 6,977,495 B2 | | 12/2005 | Donofrio |
| 6,981,628 B2 | | 1/2006 | Wales |
| 7,011,657 B2 | | 3/2006 | Truckai et al. |
| 7,041,102 B2 | | 5/2006 | Truckai et al. |
| 7,070,597 B2 | | 7/2006 | Truckai et al. |
| 7,077,853 B2 | | 7/2006 | Kramer et al. |
| 7,083,619 B2 | | 8/2006 | Truckai et al. |
| 7,087,054 B2 | | 8/2006 | Truckai et al. |
| 7,135,030 B2 | | 11/2006 | Schwemberger et al. |
| 7,179,271 B2 | | 2/2007 | Friedman et al. |
| 7,273,483 B2 | | 9/2007 | Wiener et al. |
| 7,300,431 B2 | | 11/2007 | Dubrovsky |
| 7,449,004 B2 | | 11/2008 | Yamada et al. |
| 7,524,320 B2 | | 4/2009 | Tierney et al. |
| 7,621,930 B2 | | 11/2009 | Houser |
| 7,691,098 B2 | | 4/2010 | Wallace et al. |
| 7,806,891 B2 | | 10/2010 | Nowlin et al. |
| 7,824,401 B2 | | 11/2010 | Manzo et al. |
| 8,257,387 B2 | | 9/2012 | Cunningham |
| 8,623,027 B2 | | 1/2014 | Price et al. |
| 8,663,220 B2 | | 3/2014 | Wiener et al. |
| 9,028,494 B2 | | 5/2015 | Shelton, IV et al. |
| 9,101,385 B2 | | 8/2015 | Shelton, IV et al. |
| 9,119,657 B2 | | 9/2015 | Shelton, IV et al. |
| 9,125,662 B2 | | 9/2015 | Shelton, IV |
| 9,198,714 B2 | | 12/2015 | Worrell et al. |
| 9,204,879 B2 | | 12/2015 | Shelton, IV |
| 9,226,767 B2 | | 1/2016 | Stulen et al. |
| 9,283,045 B2 | | 3/2016 | Rhee et al. |
| 9,289,256 B2 | | 3/2016 | Shelton, IV et al. |
| 9,326,788 B2 | | 5/2016 | Batross et al. |
| 9,351,754 B2 | | 5/2016 | Vakharia et al. |
| 9,393,037 B2 | | 7/2016 | Olson et al. |
| 9,408,622 B2 | | 8/2016 | Stulen et al. |
| 9,820,768 B2 | | 11/2017 | Gee et al. |
| 10,022,142 B2 | | 7/2018 | Aranyi et al. |
| 10,335,182 B2 | | 7/2019 | Stulen et al. |
| 11,871,955 B2 | | 1/2024 | Stulen et al. |
| 2002/0032452 A1 | | 3/2002 | Tierney et al. |
| 2003/0028217 A1 | * | 2/2003 | Nakamura ............ A61B 34/72 606/205 |
| 2003/0212392 A1 | | 11/2003 | Fenton et al. |
| 2006/0247558 A1 | | 11/2006 | Yamada |
| 2007/0027468 A1 | | 2/2007 | Wales et al. |
| 2007/0032704 A1 | | 2/2007 | Gandini et al. |
| 2008/0214967 A1 | * | 9/2008 | Aranyi ........... A61B 17/320068 601/3 |
| 2009/0023985 A1 | | 1/2009 | Ewers |
| 2010/0036370 A1 | | 2/2010 | Mirel et al. |
| 2014/0005640 A1 | | 1/2014 | Shelton, IV et al. |
| 2014/0005702 A1 | | 1/2014 | Timm et al. |
| 2014/0005705 A1 | | 1/2014 | Weir et al. |
| 2014/0005718 A1 | | 1/2014 | Shelton, IV et al. |

* cited by examiner

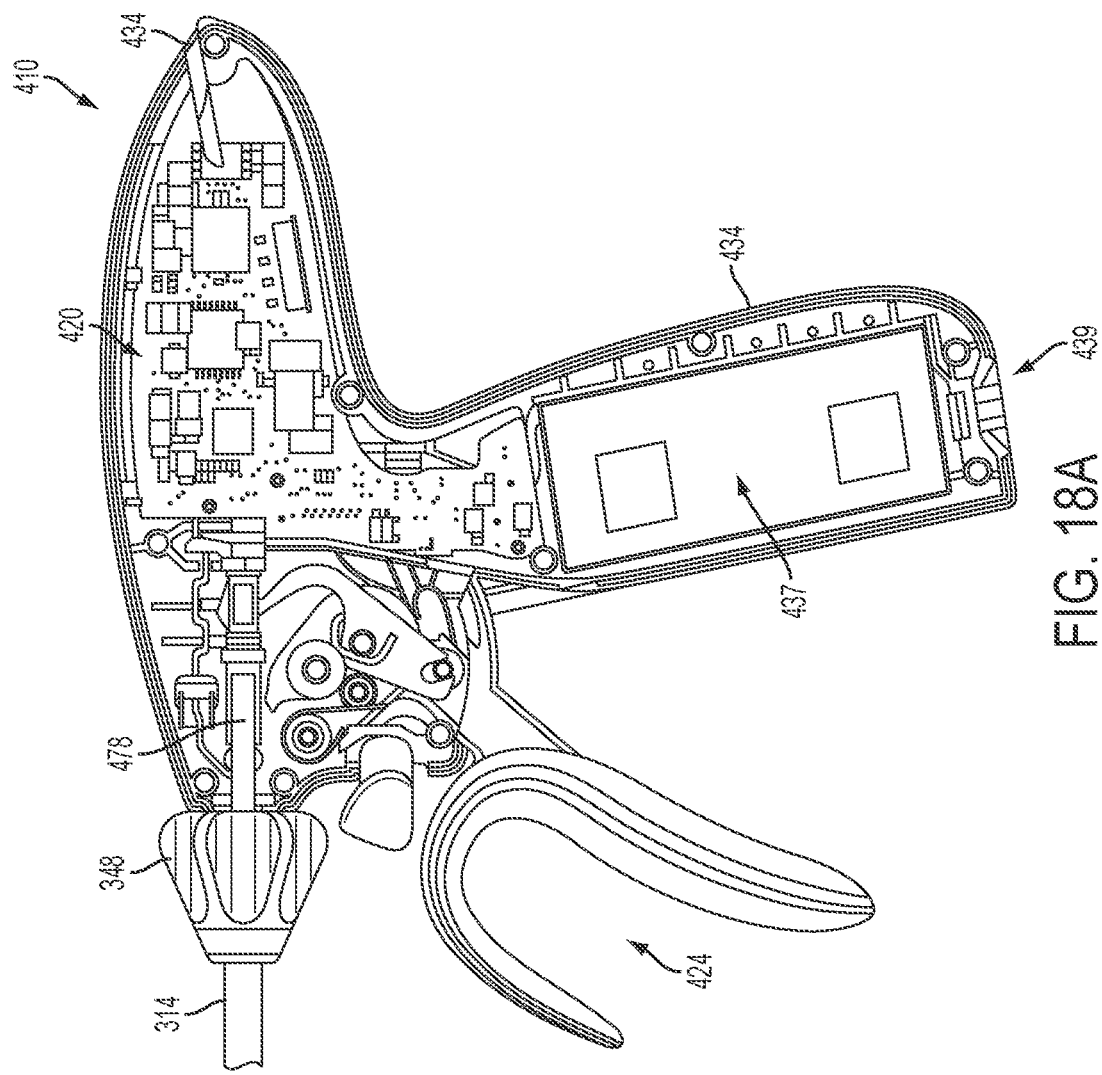

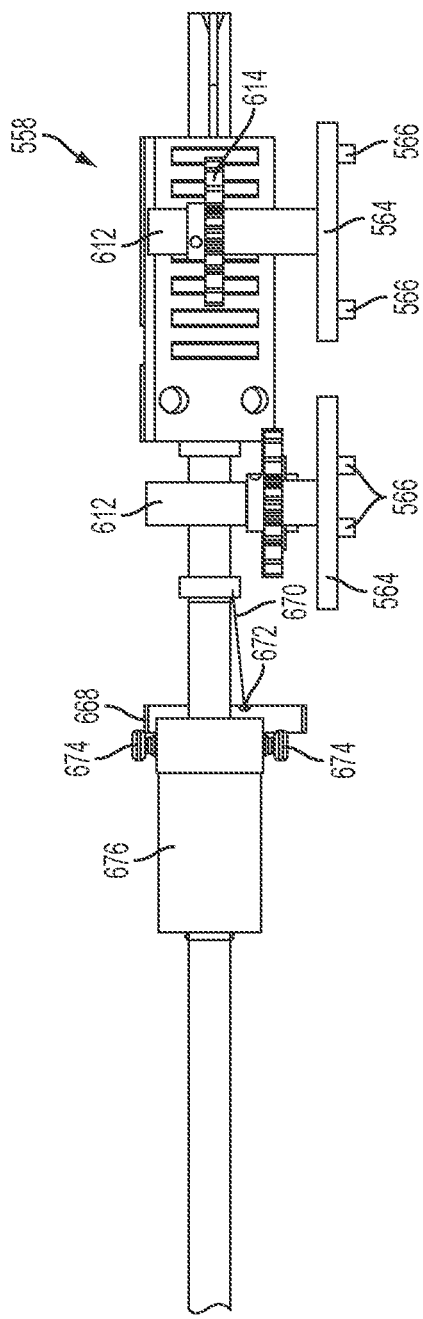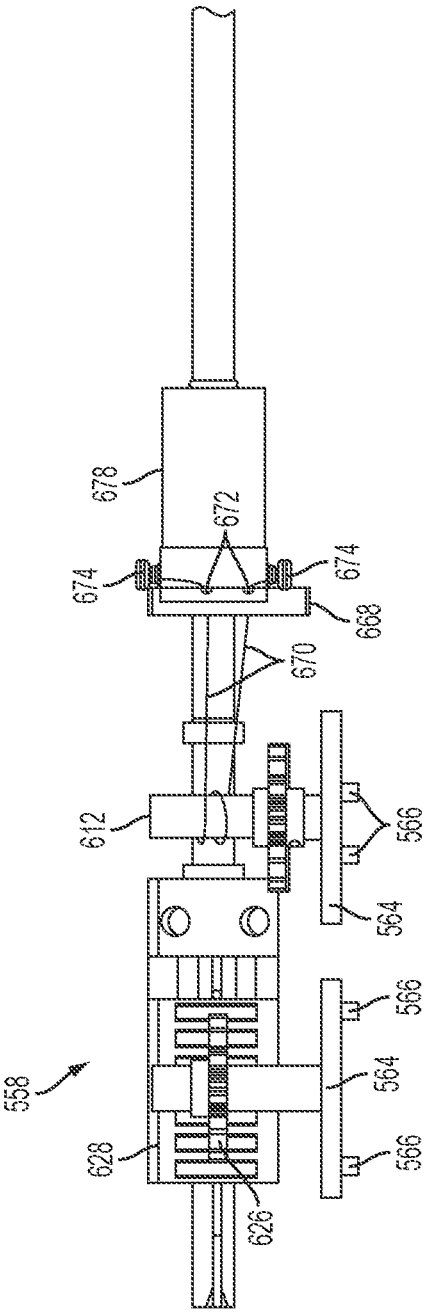

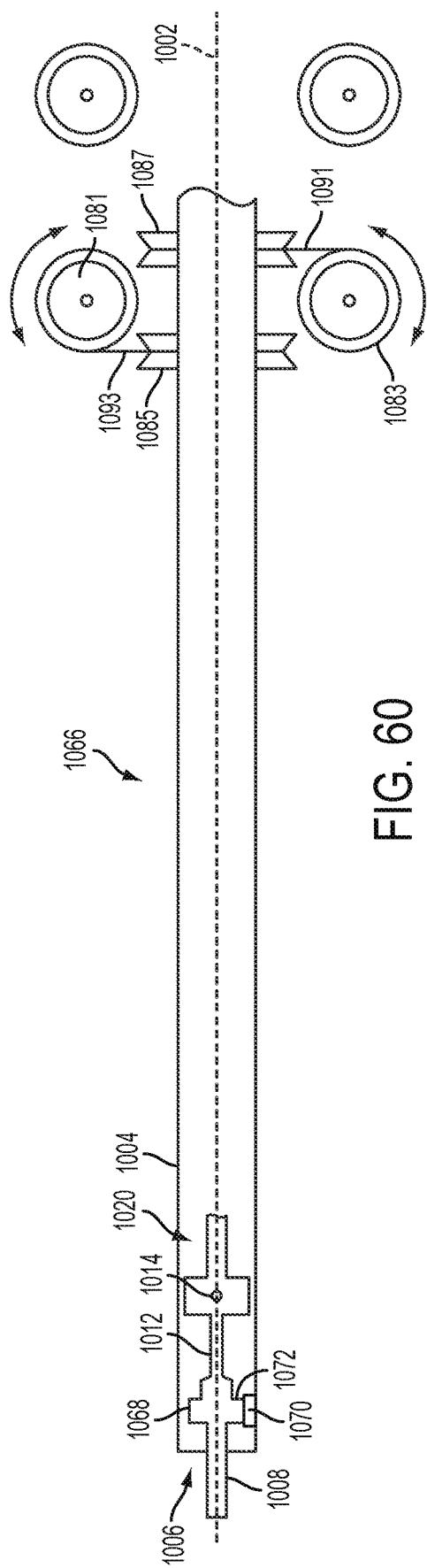
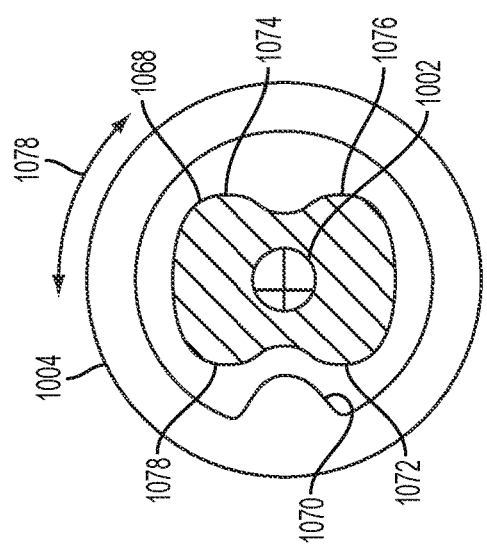
FIG. 60
FIG. 61

SURGICAL INSTRUMENTS WITH ARTICULATING SHAFTS

CROSS-REFERENCE TO RELATED APPLICATIONS

This application is a divisional application claiming priority under 35 U.S.C. § 121 to U.S. patent application Ser. No. 16/233,911, entitled SURGICAL INSTRUMENTS WITH ARTICULATING SHAFTS, filed Dec. 27, 2018, which issued on Jan. 16, 2024 as 11,871,955, which is a divisional application claiming priority under 35 U.S.C. § 121 to U.S. patent application Ser. No. 15/212,742, entitled SURGICAL INSTRUMENTS WITH ARTICULATING SHAFTS, filed Jul. 18, 2016, which issued on Jul. 2, 2019 as U.S. Pat. No. 10,335,182, which is a divisional application claiming priority under 35 U.S.C. § 121 to U.S. patent application Ser. No. 13/538,700, entitled SURGICAL INSTRUMENTS WITH ARTICULATING SHAFTS, filed Jun. 29, 2012, which issued on Aug. 9, 2016 as U.S. Pat. No. 9,408,622, the entire disclosures of which are hereby incorporated by reference herein.

This application is related to the following U.S. patent applications, filed Jun. 29, 2012, which are incorporated herein by reference in their entirety:

U.S. patent application Ser. No. 13/539,096, entitled "Haptic Feedback Devices for Surgical Robot," now U.S. Pat. No. 9,198,714;

U.S. patent application Ser. No. 13/539,110, entitled "Lockout Mechanism for Use with Robotic Electrosurgical Device," now U.S. Pat. No. 9,326,788;

U.S. patent application Ser. No. 13/539,117, entitled "Closed Feedback Control for Electrosurgical Device," now U.S. Pat. No. 9,226,767;

U.S. patent application Ser. No. 13/538,588, entitled "Surgical Instruments with Articulating Shafts," now U.S. Patent Application Publication No. 2014/0005701;

U.S. patent application Ser. No. 13/538,601, entitled "Ultrasonic Surgical Instruments with Distally Positioned Transducers," now U.S. Patent Application Publication No. 2014/0005702;

U.S. patent application Ser. No. 13/538,711, entitled "Ultrasonic Surgical Instruments with Distally Positioned Jaw Assemblies," now U.S. Pat. No. 9,351,754;

U.S. patent application Ser. No. 13/538,720, entitled "Surgical Instruments with Articulating Shafts," now U.S. Patent Application Publication No. 2014/0005705;

U.S. patent application Ser. No. 13/538,733, entitled "Ultrasonic Surgical Instruments with Control Mechanisms," now U.S. Pat. No. 9,820,768; and U.S. patent application Ser. No. 13/539,122, entitled "Surgical Instruments With Fluid Management System," now U.S. Pat. No. 9,283,045.

BACKGROUND

Various embodiments are directed to surgical devices, including various articulatable shafts and ultrasonic blades for use with surgical devices.

Ultrasonic surgical devices, such as ultrasonic scalpels, are used in many applications in surgical procedures by virtue of their unique performance characteristics. Depending upon specific device configurations and operational parameters, ultrasonic surgical devices can provide substantially simultaneous transection of tissue and homeostasis by coagulation, desirably minimizing patient trauma. An ultrasonic surgical device comprises a proximally-positioned ultrasonic transducer and an instrument coupled to the ultrasonic transducer having a distally-mounted end effector comprising an ultrasonic blade to cut and seal tissue. The end effector is typically coupled either to a handle and/or a robotic surgical implement via a shaft. The blade is acoustically coupled to the transducer via a waveguide extending through the shaft. Ultrasonic surgical devices of this nature can be configured for open surgical use, laparoscopic, or endoscopic surgical procedures including robotic-assisted procedures.

Ultrasonic energy cuts and coagulates tissue using temperatures lower than those used in electrosurgical procedures. Vibrating at high frequencies (e.g., 55,500 times per second), the ultrasonic blade denatures protein in the tissue to form a sticky coagulum. Pressure exerted on tissue by the blade surface collapses blood vessels and allows the coagulum to form a hemostatic seal. A surgeon can control the cutting speed and coagulation by the force applied to the tissue by the end effector, the time over which the force is applied and the selected excursion level of the end effector.

Also used in many surgical applications are electrosurgical devices. Electrosurgical devices apply electrical energy to tissue in order to treat tissue. An electrosurgical device may comprise an instrument having a distally-mounted end effector comprising one or more electrodes. The end effector can be positioned against tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flow through the tissue may form haemostatic seals within the tissue and/or between tissues and thus may be particularly useful for sealing blood vessels, for example. The end effector of an electrosurgical device sometimes also comprises a cutting member that is movable relative to the tissue and the electrodes to transect the tissue.

Electrical energy applied by an electrosurgical device can be transmitted to the instrument by a generator. The electrical energy may be in the form of radio frequency ("RF") energy. RF energy is a form of electrical energy that may be in the frequency range of 300 kHz to 1 MHz. During its operation, an electrosurgical device can transmit low frequency RF energy through tissue, which causes ionic agitation, or friction, in effect resistive heating, thereby increasing the temperature of the tissue. Because a sharp boundary may be created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy may work particularly well on connective tissue, which is primarily comprised of collagen and shrinks when contacted by heat.

With respect to both ultrasonic and electrosurgical devices, it is often desirable for clinicians to articulate a distal portion of the instrument shaft in order to direct the application of ultrasonic and/or RF energy. Bringing about and controlling such articulation, however, is often a considerable challenge.

DRAWINGS

The features of the various embodiments are set forth with particularity in the appended claims. The various embodiments, however, both as to organization and methods of operation, together with advantages thereof, may best be understood by reference to the following description, taken in conjunction with the accompanying drawings as follows:

FIG. 18A illustrates a side view of a handle of one embodiment of the surgical instrument of FIG. 17 with a half handle body removed to illustrate various components therein.

FIGS. 38-42 illustrate an alternate embodiment of the instrument mounting portion FIGS. 24-25 showing another alternate example mechanism for translating rotation of the driven elements into rotational motion about the axis of the shaft.

FIGS. 43-46A illustrate an alternate embodiment of the instrument mounting portion showing an alternate example mechanism for differential translation of members along the axis of the shaft (e.g., for articulation).

FIG. 60 illustrates one example embodiment of a shaft for use with various surgical instruments having a cammed articulation mechanism, including those described herein.

FIG. 61 illustrates a cross-sectional view of the shaft of FIG. 60 providing a view of the shaft cam feature and waveguide cam feature.

DESCRIPTION

Figure 1:
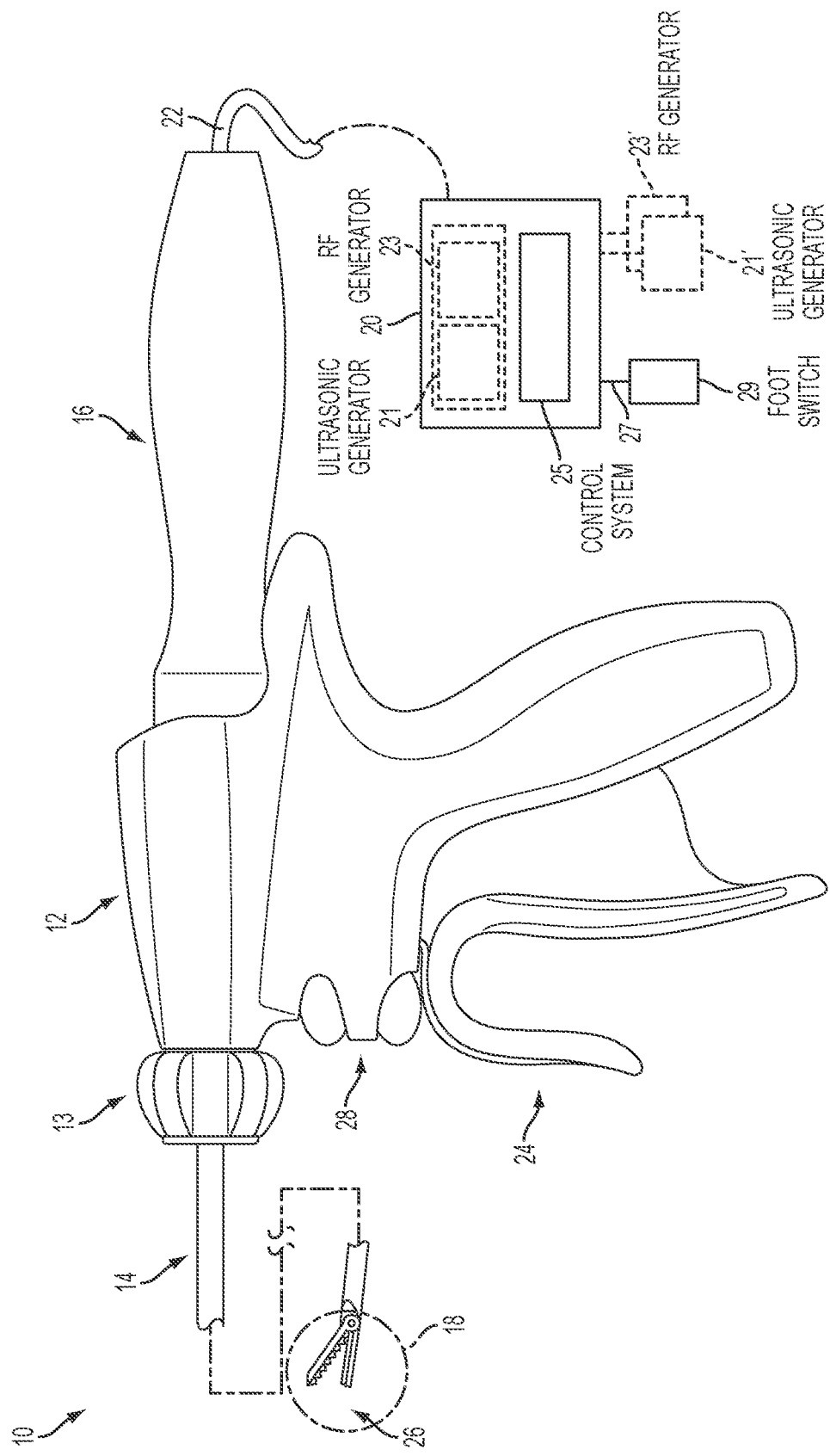
FIG. 1 illustrates one embodiment of a surgical system including a surgical instrument and an ultrasonic generator.

Example embodiments described herein are directed to articulating surgical instruments, shafts thereof, and methods of using the same. The surgical instruments may comprise an end effector configured to treat tissue in any suitable manner. In some example embodiments, the end effector comprises an ultrasonic blade for cutting and/or coagulating tissue. Details of example ultrasonic blades and the operation thereof are provided herein. Also, in some example embodiments, the end effector can comprise one or more electrodes for providing electrical energy to tissue for cutting, coagulating and/or "welding" tissue. Surgical instruments described herein may be utilized in different surgical settings. For example, different embodiments may be optimized for endoscopic, laparoscopic and/or traditional open surgical techniques. Also, different example embodiments of the surgical instruments described herein may be optimized for manual use by a clinician and/or for robotic use by a clinician in conjunction with a surgical robot.

Various example embodiments of surgical instruments described herein comprise an elongated shaft extending proximally from the end effector along a longitudinal axis. In some example embodiments, the end effector comprises an ultrasonic blade that may be articulated and/or directed from within the shaft (e.g., without otherwise articulating the shaft or in addition to otherwise articulating the shaft). For example, in some example embodiments, the ultrasonic blade is acoustically coupled to a waveguide extending proximally from the ultrasonic blade through the shaft. The waveguide may define a distally positioned flange positioned within the hollow shaft proximally from the blade. The waveguide may further be held stationary at a first pivot point positioned within the shaft proximally from the flange. A reciprocating wedge may be positioned to reciprocate distally and proximally within the shaft. Distal translation of the wedge may push the wedge between the flange and an interior wall of the shaft, ending to cause the ultrasonic blade and waveguide to pivot away from a longitudinal axis of the shaft about the first pivot point. Additional wedges may be placed at different angular positions around the interior wall of the shaft so as to articulate the ultrasonic blade in different directions.

In some example embodiments, an interior wall of the shaft defines a longitudinally directed slot and at least a portion of the reciprocating wedge is positioned within the longitudinal slot as the wedge translates distally and proximally. Also, in some example embodiments, the wedge and flange have corresponding keyed surfaces. For example, the flange may define a notch and the wedge may define a corresponding step such that the step rides within the notch as the reciprocating wedge is translated distally. Additional notches and wedges may also be present and, in some example embodiments, form a step pattern. In some example embodiments, the reciprocating wedge may be stepped, where steps are arranged along the longitudinal axis such that successive steps of the wedge cause the ultrasonic blade and waveguide to pivot about the pivot point by differing amounts.

In some example embodiments, the shaft is translatable along the longitudinal axis relative to the waveguide and ultrasonic blade. For example, the shaft may define first and second axially-directed slots, wherein the flange of the waveguide comprises first and second pegs positioned within the first and second slots. The shaft may be translatable relative to the ultrasonic blade to alternately sheathe and unsheathe the blade.

In some example embodiments, an interior portion of the hollow shaft defines a shaft cam feature directed towards the longitudinal axis. The shaft may be rotatable such that the shaft cam alternately contacts and does not contact the flange of the waveguide. In some embodiments, the flange of the waveguide has a corresponding cam feature. When the cam feature contacts the flange, it may cause the waveguide and ultrasonic blade to pivot about the pivot point. In various example embodiments, multiple surface cam features and/or multiple cam features on the flange may be utilized to bring about pivoting of the ultrasonic blade and waveguide in different directions.

In various example embodiments, the interior wall of the shaft defines a groove. Different portions of the groove are positioned at different axial distances from the end effector. The instrument may further comprise first and second interface members coupled to the ultrasonic blade and/or the waveguide at a coupling point. Each interface member extends proximally from the coupling point to a peg member. The peg members are positioned within the groove. The first interface member has a first length from the coupling point to its peg member while the second interface member has a second length from the coupling point to its peg member, where the second length is less than the first length. When the shaft rotates relative to the waveguide and ultrasonic blade, the pegs may ride within the groove and be forced either distally and/or proximally depending on the position of the pegs within the groove. When the distance from the pegs to the coupling point is different than the length of the respective coupling members, the coupling members may bend, deflecting the ultrasonic blade away from the longitudinal axis.

In various example embodiments, a surgical instrument may comprise an end effector with an ultrasonic blade, a hollow shaft and a waveguide. The shaft may comprise a rigid portion and a flexible portion. The end effector may comprises a member from which the ultrasonic blade extends, a clamp arm coupled to the member at a pivot point offset from the longitudinal axis and a flexible control cable coupled to the clamp arm at a point offset from the pivot point. Distal and proximal translation of the control cable may cause the clamp arm to pivot relative to the ultrasonic blade.

Reference will now be made in detail to several embodiments, including embodiments showing example implementations of manual and robotic surgical instruments with end effectors comprising ultrasonic and/or electrosurgical elements. Wherever practicable similar or like reference numbers may be used in the figures and may indicate similar or like functionality. The figures depict example embodiments of the disclosed surgical instruments and/or methods of use for purposes of illustration only. One skilled in the art will readily recognize from the following description that alternative example embodiments of the structures and methods illustrated herein may be employed without departing from the principles described herein.

FIG. 1 is a right side view of one embodiment of an ultrasonic surgical instrument 10. In the illustrated embodiment, the ultrasonic surgical instrument 10 may be employed in various surgical procedures including endoscopic or traditional open surgical procedures. In one example embodiment, the ultrasonic surgical instrument 10 comprises a handle assembly 12, an elongated shaft assembly 14, and an ultrasonic transducer 16. The handle assembly 12 comprises a trigger assembly 24, a distal rotation assembly 13, and a switch assembly 28. The elongated shaft assembly 14 comprises an end effector assembly 26, which comprises elements to dissect tissue or mutually grasp, cut, and coagulate vessels and/or tissue, and actuating elements to actuate the end effector assembly 26. The handle assembly 12 is adapted to receive the ultrasonic transducer 16 at the proximal end. The ultrasonic transducer 16 is mechanically engaged to the elongated shaft assembly 14 and portions of the end effector assembly 26. The ultrasonic transducer 16 is electrically coupled to a generator 20 via a cable 22. Although the majority of the drawings depict a multiple end effector assembly 26 for use in connection with laparoscopic surgical procedures, the ultrasonic surgical instrument 10 may be employed in more traditional open surgical procedures and in other embodiments, may be configured for use in endoscopic procedures and in other embodiments, may be configured for use in endoscopic procedures. For the purposes herein, the ultrasonic surgical instrument 10 is described in terms of an endoscopic instrument; however, it is contemplated that an open and/or laparoscopic version of the ultrasonic surgical instrument 10 also may include the same or similar operating components and features as described herein.

In various embodiments, the generator 20 comprises several functional elements, such as modules and/or blocks. Different functional elements or modules may be configured for driving different kinds of surgical devices. For example, an ultrasonic generator module 21 may drive an ultrasonic device, such as the ultrasonic surgical instrument 10. In some example embodiments, the generator 20 also comprises an electrosurgery/RF generator module 23 for driving an electrosurgical device (or an electrosurgical embodiment of the ultrasonic surgical instrument 10). In various embodiments, the generator 20 may be formed integrally within the handle assembly 12. In such implementations, a battery would be co-located within the handle assembly 12 to act as the energy source. FIG. 18A and accompanying disclosures provide one example of such implementations. As shown in FIG. 1, according to various embodiments, the ultrasonic generator module 21 and/or the electrosurgery/RF generator module 23 may be located external to the generator (shown in phantom as ultrasonic generator module 21' and electrosurgery/RF generator module 23'). In some embodiments, the electrosurgery/RF generator module 23 may be configured to generate a therapeutic and/or a sub-therapeutic energy level. In the example embodiment illustrated in FIG. 1, the generator 20 includes a control system 25 integral with the generator 20, and a foot switch 29 connected to the generator via a cable 27. The generator 20 may also comprise a triggering mechanism for activating a surgical instrument, such as the instrument 10. The triggering mechanism may include a power switch (not shown) as well as a foot switch 29. When activated by the foot switch 29, the generator 20 may provide energy to drive the acoustic assembly of the surgical instrument 10 and to drive the end effector 18 at a predetermined excursion level. The generator 20 drives or excites the acoustic assembly at any suitable resonant frequency of the acoustic assembly and/or derives the therapeutic/sub-therapeutic electromagnetic/RF energy.

In one embodiment, the electrosurgical/RF generator module 23 may be implemented as an electrosurgery unit (ESU) capable of supplying power sufficient to perform bipolar electrosurgery using radio frequency (RF) energy. In one embodiment, the ESU can be a bipolar ERBE ICC 350 sold by ERBE USA, Inc. of Marietta, Ga. In bipolar electrosurgery applications, as previously discussed, a surgical instrument having an active electrode and a return electrode can be utilized, wherein the active electrode and the return electrode can be positioned against, or adjacent to, the tissue to be treated such that current can flow from the active electrode to the return electrode through the tissue. Accordingly, the electrosurgical/RF module 23 generator may be configured for therapeutic purposes by applying electrical energy to the tissue T sufficient for treating the tissue (e.g., cauterization).

In one embodiment, the electrosurgical/RF generator module 23 may be configured to deliver a sub-therapeutic RF signal to implement a tissue impedance measurement module. In one embodiment, the electrosurgical/RF generator module 23 comprises a bipolar radio frequency generator as described in more detail below. In one embodiment, the electrosurgical/RF generator module 23 may be configured to monitor electrical impedance Z, of tissue T and to control the characteristics of time and power level based on the tissue T by way of a return electrode provided on a clamp member of the end effector assembly 26. Accordingly, the electrosurgical/RF generator module 23 may be configured for sub-therapeutic purposes for measuring the impedance or other electrical characteristics of the tissue T. Techniques and circuit configurations for measuring the impedance or other electrical characteristics of tissue T are discussed in more detail in commonly assigned U.S. Patent Publication No. 2011/0015631, titled "Electrosurgical Generator for Ultrasonic Surgical Instruments," the disclosure of which is herein incorporated by reference in its entirety.

A suitable ultrasonic generator module 21 may be configured to functionally operate in a manner similar to the GEN300 sold by Ethicon Endo-Surgery, Inc of Cincinnati, Ohio as is disclosed in one or more of the following U.S. patents, all of which are incorporated by reference herein: U.S. Pat. No. 6,480,796 (Method for Improving the Start Up of an Ultrasonic System Under Zero Load Conditions); U.S. Pat. No. 6,537,291 (Method for Detecting Blade Breakage Using Rate and/or Impedance Information); U.S. Pat. No. 6,662,127 (Method for Detecting Presence of a Blade in an Ultrasonic System); U.S. Pat. No. 6,679,899 (Method for Detecting Transverse Vibrations in an Ultrasonic Hand Piece); U.S. Pat. No. 6,977,495 (Detection Circuitry for Surgical Handpiece System); U.S. Pat. No. 7,077,853 (Method for Calculating Transducer Capacitance to Determine Transducer Temperature); U.S. Pat. No. 7,179,271 (Method for Driving an Ultrasonic System to Improve Acquisition of Blade Resonance Frequency at Startup); and U.S. Pat. No. 7,273,483 (Apparatus and Method for Alerting Generator Function in an Ultrasonic Surgical System).

It will be appreciated that in various embodiments, the generator 20 may be configured to operate in several modes. In one mode, the generator 20 may be configured such that the ultrasonic generator module 21 and the electrosurgical/RF generator module 23 may be operated independently.

For example, the ultrasonic generator module 21 may be activated to apply ultrasonic energy to the end effector assembly 26 and subsequently, either therapeutic or sub-therapeutic RF energy may be applied to the end effector assembly 26 by the electrosurgical/RF generator module 23. As previously discussed, the sub-therapeutic electrosurgical/RF energy may be applied to tissue clamped between claim elements of the end effector assembly 26 to measure tissue impedance to control the activation, or modify the activation, of the ultrasonic generator module 21. Tissue impedance feedback from the application of the sub-therapeutic energy also may be employed to activate a therapeutic level of the electrosurgical/RF generator module 23 to seal the tissue (e.g., vessel) clamped between claim elements of the end effector assembly 26.

In another embodiment, the ultrasonic generator module 21 and the electrosurgical/RF generator module 23 may be activated simultaneously. In one example, the ultrasonic generator module 21 is simultaneously activated with a sub-therapeutic RF energy level to measure tissue impedance simultaneously while the ultrasonic blade of the end effector assembly 26 cuts and coagulates the tissue (or vessel) clamped between the clamp elements of the end effector assembly 26. Such feedback may be employed, for example, to modify the drive output of the ultrasonic generator module 21. In another example, the ultrasonic generator module 21 may be driven simultaneously with electrosurgical/RF generator module 23 such that the ultrasonic blade portion of the end effector assembly 26 is employed for cutting the damaged tissue while the electrosurgical/RF energy is applied to electrode portions of the end effector clamp assembly 26 for sealing the tissue (or vessel).

When the generator 20 is activated via the triggering mechanism, electrical energy is continuously applied by the generator 20 to a transducer stack or assembly of the acoustic assembly. In another embodiment, electrical energy is intermittently applied (e.g., pulsed) by the generator 20. A phase-locked loop in the control system of the generator 20 may monitor feedback from the acoustic assembly. The phase lock loop adjusts the frequency of the electrical energy sent by the generator 20 to match the resonant frequency of the selected longitudinal mode of vibration of the acoustic assembly. In addition, a second feedback loop in the control system 25 maintains the electrical current supplied to the acoustic assembly at a pre-selected constant level in order to achieve substantially constant excursion at the end effector 18 of the acoustic assembly. In yet another embodiment, a third feedback loop in the control system 25 monitors impedance between electrodes located in the end effector assembly 26. Although FIGS. 1-9 show a manually operated ultrasonic surgical instrument, it will be appreciated that ultrasonic surgical instruments may also be used in robotic applications, for example, as described herein, as well as combinations of manual and robotic applications.

In ultrasonic operation mode, the electrical signal supplied to the acoustic assembly may cause the distal end of the end effector 18, to vibrate longitudinally in the range of, for example, approximately 20 kHz to 250 kHz. According to various embodiments, the blade 22 may vibrate in the range of about 54 kHz to 56 kHz, for example, at about 55.5 kHz. In other embodiments, the blade 22 may vibrate at other frequencies including, for example, about 31 kHz or about 80 kHz. The excursion of the vibrations at the blade can be controlled by, for example, controlling the amplitude of the electrical signal applied to the transducer assembly of the acoustic assembly by the generator 20. As noted above, the triggering mechanism of the generator 20 allows a user to activate the generator 20 so that electrical energy may be continuously supplied to the acoustic assembly. The generator 20 also has a power line for insertion in an electrosurgical unit or conventional electrical outlet. It is contemplated that the generator 20 can also be powered by a direct current (DC) source, such as a battery. The generator 20 can comprise any suitable generator, such as Model No. GEN04, and/or Model No. GEN11 available from Ethicon Endo-Surgery, Inc.

Figure 2:
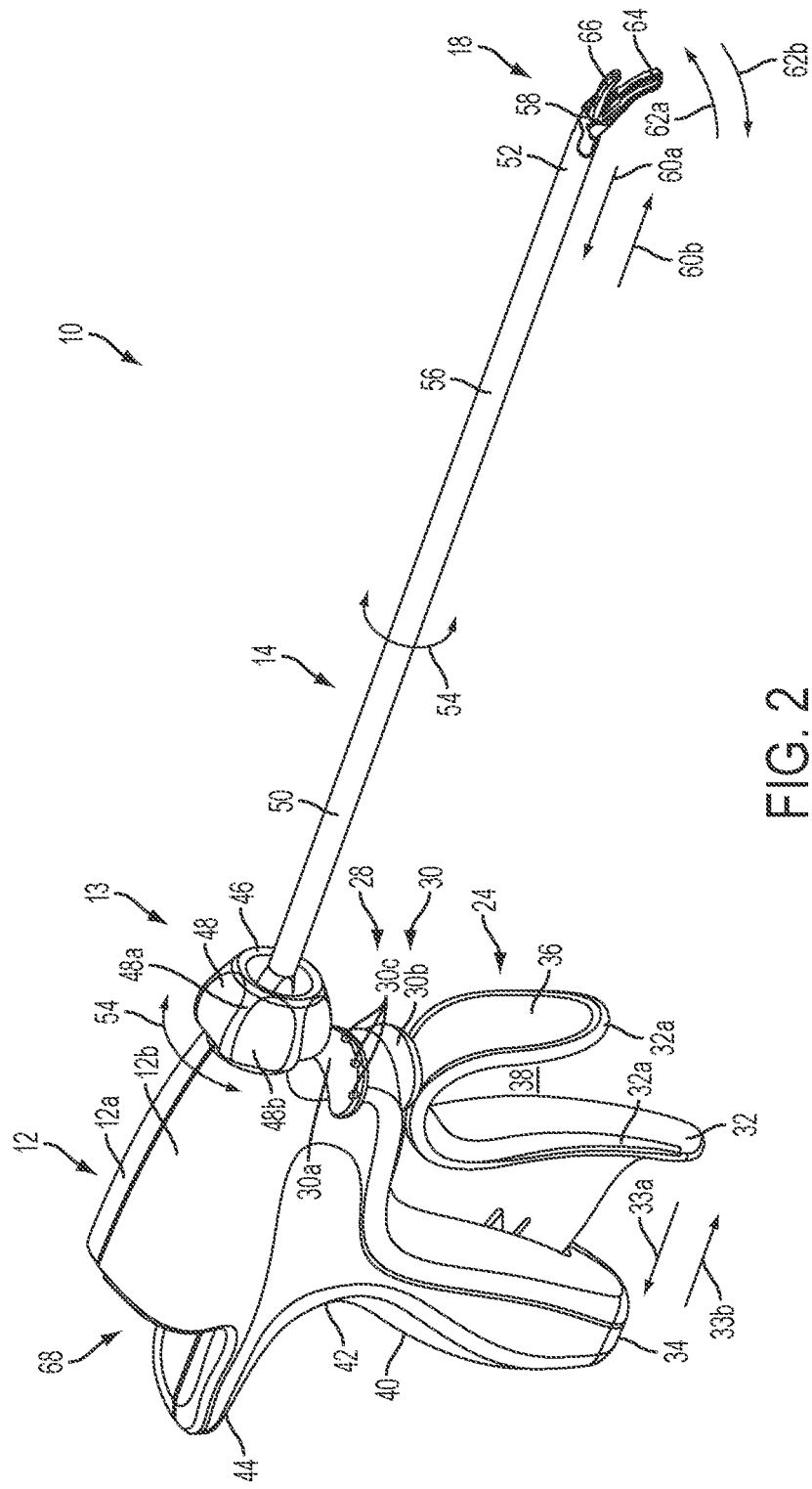
FIG. 2 illustrates one embodiment of the surgical instrument shown in FIG. 1.

FIG. 2 is a left perspective view of one example embodiment of the ultrasonic surgical instrument 10 showing the handle assembly 12, the distal rotation assembly 13, the elongated shaft assembly 14, and the end effector assembly 26. In the illustrated embodiment the elongated shaft assembly 14 comprises a distal end 52 dimensioned to mechanically engage the end effector assembly 26 and a proximal end 50 that mechanically engages the handle assembly 12 and the distal rotation assembly 13. The proximal end 50 of the elongated shaft assembly 14 is received within the handle assembly 12 and the distal rotation assembly 13. More details relating to the connections between the elongated shaft assembly 14, the handle assembly 12, and the distal rotation assembly 13 are provided in the description of FIGS. 5 and 7.

In the illustrated embodiment, the trigger assembly 24 comprises a trigger 32 that operates in conjunction with a fixed handle 34. The fixed handle 34 and the trigger 32 are ergonomically formed and adapted to interface comfortably with the user. The fixed handle 34 is integrally associated with the handle assembly 12. The trigger 32 is pivotally movable relative to the fixed handle 34 as explained in more detail below with respect to the operation of the ultrasonic surgical instrument 10. The trigger 32 is pivotally movable in direction 33A toward the fixed handle 34 when the user applies a squeezing force against the trigger 32. A spring element 98 (FIG. 5) causes the trigger 32 to pivotally move in direction 33B when the user releases the squeezing force against the trigger 32.

In one example embodiment, the trigger 32 comprises an elongated trigger hook 36, which defines an aperture 38 between the elongated trigger hook 36 and the trigger 32. The aperture 38 is suitably sized to receive one or multiple fingers of the user therethrough. The trigger 32 also may comprise a resilient portion 32a molded over the trigger 32 substrate. The resilient portion 32a is formed to provide a more comfortable contact surface for control of the trigger 32 in outward direction 33B. In one example embodiment, the resilient portion 32a may also be provided over a portion of the elongated trigger hook 36 as shown, for example, in FIG. 2. The proximal surface of the elongated trigger hook 32 remains uncoated or coated with a non-resilient substrate to enable the user to easily slide their fingers in and out of the aperture 38. In another embodiment, the geometry of the trigger forms a fully closed loop which defines an aperture suitably sized to receive one or multiple fingers of the user therethrough. The fully closed loop trigger also may comprise a resilient portion molded over the trigger substrate.

In one example embodiment, the fixed handle 34 comprises a proximal contact surface 40 and a grip anchor or saddle surface 42. The saddle surface 42 rests on the web where the thumb and the index finger are joined on the hand. The proximal contact surface 40 has a pistol grip contour that receives the palm of the hand in a normal pistol grip with no rings or apertures. The profile curve of the proximal contact surface 40 may be contoured to accommodate or receive the palm of the hand. A stabilization tail 44 is located towards a more proximal portion of the handle assembly 12. The stabilization tail 44 may be in contact with the uppermost web portion of the hand located between the thumb and the index finger to stabilize the handle assembly 12 and make the handle assembly 12 more controllable.

In one example embodiment, the switch assembly 28 may comprise a toggle switch 30. The toggle switch 30 may be implemented as a single component with a central pivot 304 located within inside the handle assembly 12 to eliminate the possibility of simultaneous activation. In one example embodiment, the toggle switch 30 comprises a first projecting knob 30a and a second projecting knob 30b to set the power setting of the ultrasonic transducer 16 between a minimum power level (e.g., MIN) and a maximum power level (e.g., MAX). In another embodiment, the rocker switch may pivot between a standard setting and a special setting. The special setting may allow one or more special programs to be implemented by the device. The toggle switch 30 rotates about the central pivot as the first projecting knob 30a and the second projecting knob 30b are actuated. The one or more projecting knobs 30a, 30b are coupled to one or more arms that move through a small arc and cause electrical contacts to close or open an electric circuit to electrically energize or de-energize the ultrasonic transducer 16 in accordance with the activation of the first or second projecting knobs 30a, 30b. The toggle switch 30 is coupled to the generator 20 to control the activation of the ultrasonic transducer 16. The toggle switch 30 comprises one or more electrical power setting switches to activate the ultrasonic transducer 16 to set one or more power settings for the ultrasonic transducer 16. The forces required to activate the toggle switch 30 are directed substantially toward the saddle point 42, thus avoiding any tendency of the instrument to rotate in the hand when the toggle switch 30 is activated.

In one example embodiment, the first and second projecting knobs 30a, 30b are located on the distal end of the handle assembly 12 such that they can be easily accessible by the user to activate the power with minimal, or substantially no, repositioning of the hand grip, making it suitable to maintain control and keep attention focused on the surgical site (e.g., a monitor in a laparoscopic procedure) while activating the toggle switch 30. The projecting knobs 30a, 30b may be configured to wrap around the side of the handle assembly 12 to some extent to be more easily accessible by variable finger lengths and to allow greater freedom of access to activation in awkward positions or for shorter fingers.

In the illustrated embodiment, the first projecting knob 30a comprises a plurality of tactile elements 30c, e.g., textured projections or "bumps" in the illustrated embodiment, to allow the user to differentiate the first projecting knob 30a from the second projecting knob 30b. It will be appreciated by those skilled in the art that several ergonomic features may be incorporated into the handle assembly 12. Such ergonomic features are described in U.S. Pat. App. Pub. No. 2009/0105750 entitled "Ergonomic Surgical Instruments," now U.S. Pat. No. 8,623,027, which is incorporated by reference herein in its entirety.

In one example embodiment, the toggle switch 30 may be operated by the hand of the user. The user may easily access the first and second projecting knobs 30a, 30b at any point while also avoiding inadvertent or unintentional activation at any time. The toggle switch 30 may readily operated with a finger to control the power to the ultrasonic assembly 16 and/or to the ultrasonic assembly 16. For example, the index finger may be employed to activate the first contact portion 30a to turn on the ultrasonic assembly 16 to a maximum (MAX) power level. The index finger may be employed to activate the second contact portion 30b to turn on the ultrasonic assembly 16 to a minimum (MIN) power level. In another embodiment, the rocker switch may pivot the instrument 10 between a standard setting and a special setting. The special setting may allow one or more special programs to be implemented by the instrument 10. The toggle switch 30 may be operated without the user having to look at the first or second projecting knob 30a, 30b. For example, the first projecting knob 30a or the second projecting knob 30b may comprise a texture or projections to tactilely differentiate between the first and second projecting knobs 30a, 30b without looking.

In other embodiments, the trigger 32 and/or the toggle switch 30 may be employed to actuate the electrosurgical/RF generator module 23 individually or in combination with activation of the ultrasonic generator module 21.

In one example embodiment, the distal rotation assembly 13 is rotatable without limitation in either direction about a longitudinal axis "T." The distal rotation assembly 13 is mechanically engaged to the elongated shaft assembly 14.

The distal rotation assembly 13 is located on a distal end of the handle assembly 12. The distal rotation assembly 13 comprises a cylindrical hub 46 and a rotation knob 48 formed over the hub 46. The hub 46 mechanically engages the elongated shaft assembly 14. The rotation knob 48 may comprise fluted polymeric features and may be engaged by a finger (e.g., an index finger) to rotate the elongated shaft assembly 14. The hub 46 may comprise a material molded over the primary structure to form the rotation knob 48. The rotation knob 48 may be overmolded over the hub 46. The hub 46 comprises an end cap portion 46a that is exposed at the distal end. The end cap portion 46a of the hub 46 may contact the surface of a trocar during laparoscopic procedures. The hub 46 may be formed of a hard durable plastic such as polycarbonate to alleviate any friction that may occur between the end cap portion 46a and the trocar. The rotation knob 48 may comprise "scallops" or flutes formed of raised ribs 48a and concave portions 48b located between the ribs 48a to provide a more precise rotational grip. In one example embodiment, the rotation knob 48 may comprise a plurality of flutes (e.g., three or more flutes). In other embodiments, any suitable number of flutes may be employed. The rotation knob 48 may be formed of a softer polymeric material overmolded onto the hard plastic material. For example, the rotation knob 48 may be formed of pliable, resilient, flexible polymeric materials including Versaflex® TPE alloys made by GLS Corporation, for example. This softer overmolded material may provide a greater grip and more precise control of the movement of the rotation knob 48. It will be appreciated that any materials that provide adequate resistance to sterilization, are biocompatible, and provide adequate frictional resistance to surgical gloves may be employed to form the rotation knob 48.

In one example embodiment, the handle assembly 12 is formed from two (2) housing portions or shrouds comprising a first portion 12a and a second portion 12b. From the perspective of a user viewing the handle assembly 12 from the distal end towards the proximal end, the first portion 12a is considered the right portion and the second portion 12b is considered the left portion. Each of the first and second portions 12a, 12b includes a plurality of interfaces 69 (FIG. 7) dimensioned to mechanically align and engage each another to form the handle assembly 12 and enclosing the internal working components thereof. The fixed handle 34, which is integrally associated with the handle assembly 12, takes shape upon the assembly of the first and second portions 12a and 12b of the handle assembly 12. A plurality of additional interfaces (not shown) may be disposed at various points around the periphery of the first and second portions 12a and 12b of the handle assembly 12 for ultrasonic welding purposes, e.g., energy direction/deflection points. The first and second portions 12a and 12b (as well as the other components described below) may be assembled together in any fashion known in the art. For example, alignment pins, snap-like interfaces, tongue and groove interfaces, locking tabs, adhesive ports, may all be utilized either alone or in combination for assembly purposes.

In one example embodiment, the elongated shaft assembly 14 comprises a proximal end 50 adapted to mechanically engage the handle assembly 12 and the distal rotation assembly 13; and a distal end 52 adapted to mechanically engage the end effector assembly 26. The elongated shaft assembly 14 comprises an outer tubular sheath 56 and a reciprocating tubular actuating member 58 located within the outer tubular sheath 56. The proximal end of the tubular reciprocating tubular actuating member 58 is mechanically engaged to the trigger 32 of the handle assembly 12 to move in either direction 60A or 60B in response to the actuation and/or release of the trigger 32. The pivotably moveable trigger 32 may generate reciprocating motion along the longitudinal axis "T." Such motion may be used, for example, to actuate the jaws or clamping mechanism of the end effector assembly 26. A series of linkages translate the pivotal rotation of the trigger 32 to axial movement of a yoke coupled to an actuation mechanism, which controls the opening and closing of the jaws of the clamping mechanism of the end effector assembly 26. The distal end of the tubular reciprocating tubular actuating member 58 is mechanically engaged to the end effector assembly 26. In the illustrated embodiment, the distal end of the tubular reciprocating tubular actuating member 58 is mechanically engaged to a clamp arm assembly 64, which is pivotable about a pivot point 70, to open and close the clamp arm assembly 64 in response to the actuation and/or release of the trigger 32. For example, in the illustrated embodiment, the clamp arm assembly 64 is movable in direction 62A from an open position to a closed position about a pivot point 70 when the trigger 32 is squeezed in direction 33A. The clamp arm assembly 64 is movable in direction 62B from a closed position to an open position about the pivot point 70 when the trigger 32 is released or outwardly contacted in direction 33B.

In one example embodiment, the end effector assembly 26 is attached at the distal end 52 of the elongated shaft assembly 14 and includes a clamp arm assembly 64 and a blade 66. The jaws of the clamping mechanism of the end effector assembly 26 are formed by clamp arm assembly 64 and the blade 66. The blade 66 is ultrasonically actuatable and is acoustically coupled to the ultrasonic transducer 16. The trigger 32 on the handle assembly 12 is ultimately connected to a drive assembly, which together, mechanically cooperate to effect movement of the clamp arm assembly 64. Squeezing the trigger 32 in direction 33A moves the clamp arm assembly 64 in direction 62A from an open position, wherein the clamp arm assembly 64 and the blade 66 are disposed in a spaced relation relative to one another, to a clamped or closed position, wherein the clamp arm assembly 64 and the blade 66 cooperate to grasp tissue therebetween. The clamp arm assembly 64 may comprise a clamp pad (not shown) to engage tissue between the blade 66 and the clamp arm 64. Releasing the trigger 32 in direction 33B moves the clamp arm assembly 64 in direction 62B from a closed relationship, to an open position, wherein the clamp arm assembly 64 and the blade 66 are disposed in a spaced relation relative to one another.

The proximal portion of the handle assembly 12 comprises a proximal opening 68 to receive the distal end of the ultrasonic assembly 16. The ultrasonic assembly 16 is inserted in the proximal opening 68 and is mechanically engaged to the elongated shaft assembly 14.

In one example embodiment, the elongated trigger hook 36 portion of the trigger 32 provides a longer trigger lever with a shorter span and rotation travel. The longer lever of the elongated trigger hook 36 allows the user to employ multiple fingers within the aperture 38 to operate the elongated trigger hook 36 and cause the trigger 32 to pivot in direction 33B to open the jaws of the end effector assembly 26. For example, the user may insert three fingers (e.g., the middle, ring, and little fingers) in the aperture 38. Multiple fingers allows the surgeon to exert higher input forces on the trigger 32 and the elongated trigger hook 36 to activate the end effector assembly 26. The shorter span and rotation travel creates a more comfortable grip when closing or squeezing the trigger 32 in direction 33A or when opening the trigger 32 in the outward opening motion in direction 33B lessening the need to extend the fingers further outward. This substantially lessens hand fatigue and strain associated with the outward opening motion of the trigger 32 in direction 33B. The outward opening motion of the trigger may be spring-assisted by spring element 98 (FIG. 5) to help alleviate fatigue. The opening spring force is sufficient to assist the ease of opening, but not strong enough to adversely impact the tactile feedback of tissue tension during spreading dissection.

For example, during a surgical procedure the index finger may be used to control the rotation of the elongated shaft assembly 14 to locate the jaws of the end effector assembly 26 in a suitable orientation. The middle and/or the other lower fingers may be used to squeeze the trigger 32 and grasp tissue within the jaws. Once the jaws are located in the desired position and the jaws are clamped against the tissue, the index finger can be used to activate the toggle switch 30 to adjust the power level of the ultrasonic transducer 16 to treat the tissue. Once the tissue has been treated, the user may release the trigger 32 by pushing outwardly in the distal direction against the elongated trigger hook 36 with the middle and/or lower fingers to open the jaws of the end effector assembly 26. This basic procedure may be performed without the user having to adjust their grip of the handle assembly 12.

Figure 3:
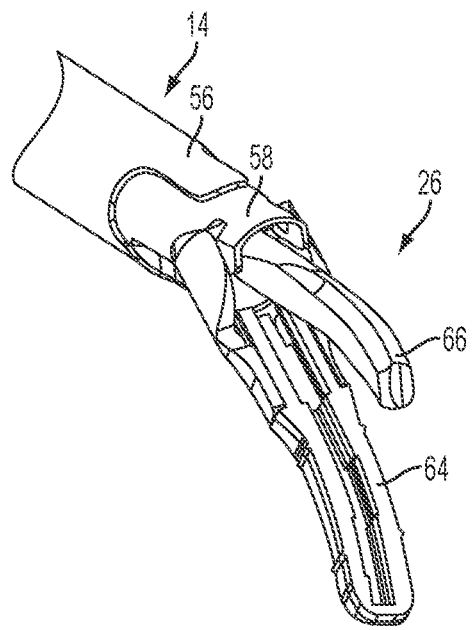
FIG. 3 illustrates one embodiment of an ultrasonic end effector.
Figure 4:
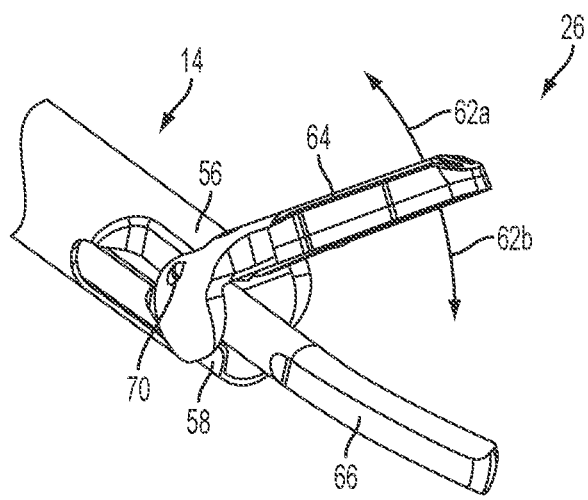
FIG. 4 illustrates another embodiment of an ultrasonic end effector.

FIGS. 3-4 illustrate the connection of the elongated shaft assembly 14 relative to the end effector assembly 26. As previously described, in the illustrated embodiment, the end effector assembly 26 comprises a clamp arm assembly 64 and a blade 66 to form the jaws of the clamping mechanism. The blade 66 may be an ultrasonically actuatable blade acoustically coupled to the ultrasonic transducer 16. The trigger 32 is mechanically connected to a drive assembly. Together, the trigger 32 and the drive assembly mechanically cooperate to move the clamp arm assembly 64 to an open position in direction 62A wherein the clamp arm assembly 64 and the blade 66 are disposed in spaced relation relative to one another, to a clamped or closed position in direction 62B wherein the clamp arm assembly 64 and the blade 66 cooperate to grasp tissue therebetween. The clamp arm assembly 64 may comprise a clamp pad (not shown) to engage tissue between the blade 66 and the clamp arm 64. The distal end of the tubular reciprocating tubular actuating member 58 is mechanically engaged to the end effector assembly 26. In the illustrated embodiment, the distal end of the tubular reciprocating tubular actuating member 58 is mechanically engaged to the clamp arm assembly 64, which is pivotable about the pivot point 70, to open and close the clamp arm assembly 64 in response to the actuation and/or release of the trigger 32. For example, in the illustrated embodiment, the clamp arm assembly 64 is movable from an open position to a closed position in direction 62B about a pivot point 70 when the trigger 32 is squeezed in direction 33A. The clamp arm assembly 64 is movable from a closed position to an open position in direction 62A about the pivot point 70 when the trigger 32 is released or outwardly contacted in direction 33B.

As previously discussed, the clamp arm assembly 64 may comprise electrodes electrically coupled to the electrosurgical/RF generator module 23 to receive therapeutic and/or sub-therapeutic energy, where the electrosurgical/RF energy may be applied to the electrodes either simultaneously or non-simultaneously with the ultrasonic energy being applied to the blade 66. Such energy activations may be applied in any suitable combinations to achieve a desired tissue effect in cooperation with an algorithm or other control logic.

Figure 5:
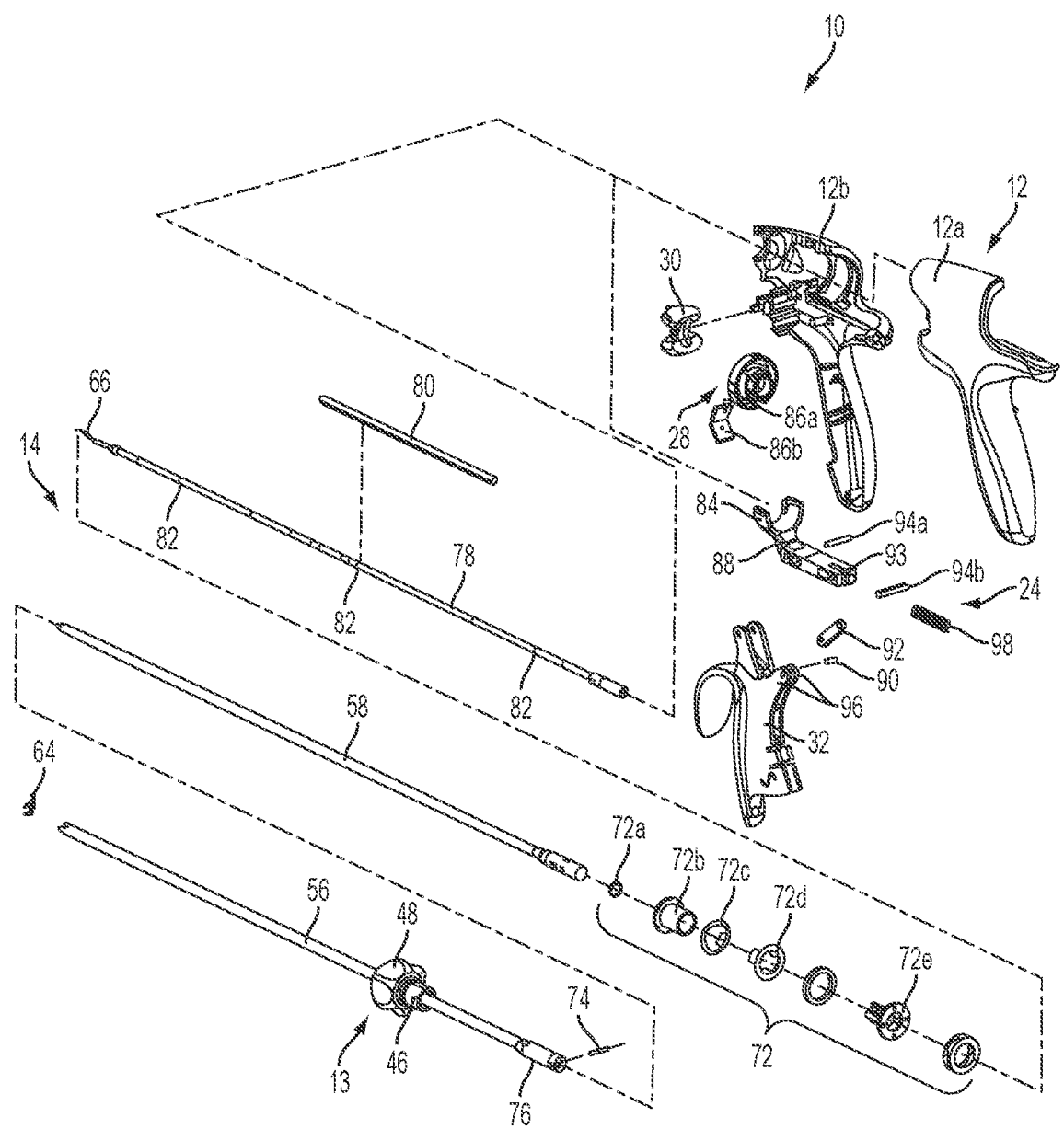
FIG. 5 illustrates an exploded view of one embodiment of the surgical instrument shown in FIG. 1.
Figure 7:
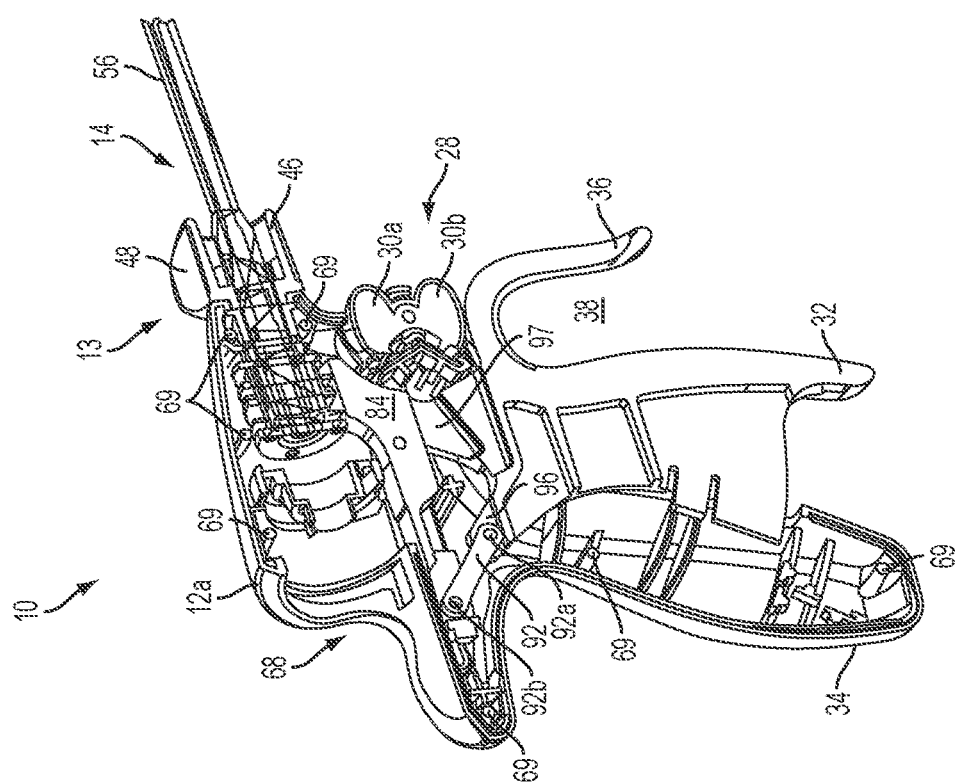
FIG. 7 illustrates various internal components of one embodiment of the surgical instrument shown in FIG. 1
Figure 6:
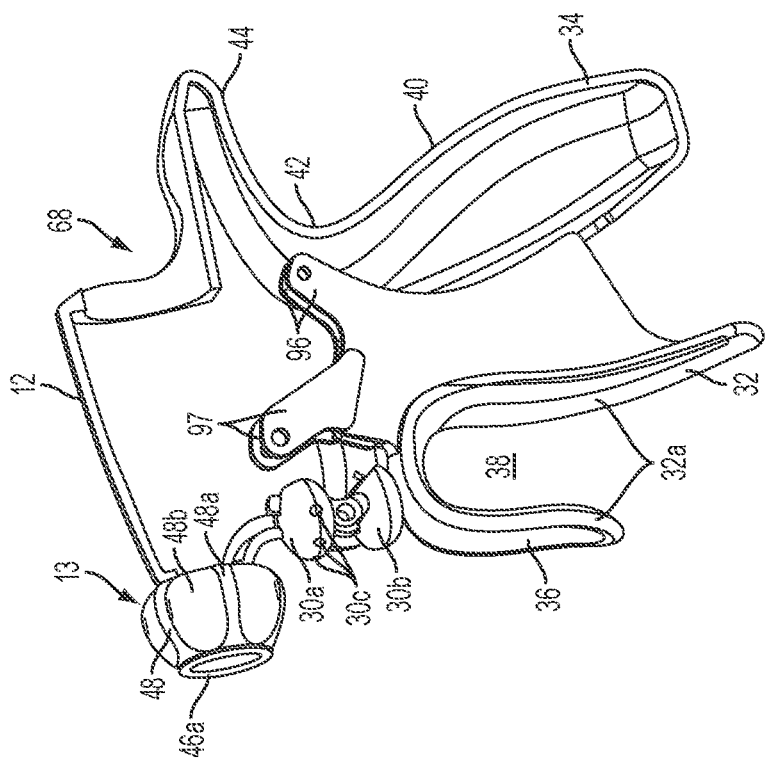
FIG. 6 illustrates a cut-away view of one embodiment of the surgical instrument shown in FIG. 1.

FIG. 5 is an exploded view of the ultrasonic surgical instrument 10 shown in FIG. 2. In the illustrated embodiment, the exploded view shows the internal elements of the handle assembly 12, the handle assembly 12, the distal rotation assembly 13, the switch assembly 28, and the elongated shaft assembly 14. In the illustrated embodiment, the first and second portions 12a, 12b mate to form the handle assembly 12. The first and second portions 12a, 12b each comprises a plurality of interfaces 69 dimensioned to mechanically align and engage one another to form the handle assembly 12 and enclose the internal working components of the ultrasonic surgical instrument 10. The rotation knob 48 is mechanically engaged to the outer tubular sheath 56 so that it may be rotated in circular direction 54 up to 360°. The outer tubular sheath 56 is located over the reciprocating tubular actuating member 58, which is mechanically engaged to and retained within the handle assembly 12 via a plurality of coupling elements 72. The coupling elements 72 may comprise an O-ring 72a, a tube collar cap 72b, a distal washer 72c, a proximal washer 72d, and a thread tube collar 72e. The reciprocating tubular actuating member 58 is located within a reciprocating yoke 84, which is retained between the first and second portions 12a, 12b of the handle assembly 12. The yoke 84 is part of a reciprocating yoke assembly 88. A series of linkages translate the pivotal rotation of the elongated trigger hook 32 to the axial movement of the reciprocating yoke 84, which controls the opening and closing of the jaws of the clamping mechanism of the end effector assembly 26 at the distal end of the ultrasonic surgical instrument 10. In one example embodiment, a four-link design provides mechanical advantage in a relatively short rotation span, for example.

In one example embodiment, an ultrasonic transmission waveguide 78 is disposed inside the reciprocating tubular actuating member 58. The distal end 52 of the ultrasonic transmission waveguide 78 is acoustically coupled (e.g., directly or indirectly mechanically coupled) to the blade 66 and the proximal end 50 of the ultrasonic transmission waveguide 78 is received within the handle assembly 12. The proximal end 50 of the ultrasonic transmission waveguide 78 is adapted to acoustically couple to the distal end of the ultrasonic transducer 16 as discussed in more detail below. The ultrasonic transmission waveguide 78 is isolated from the other elements of the elongated shaft assembly 14 by a protective sheath 80 and a plurality of isolation elements 82, such as silicone rings. The outer tubular sheath 56, the reciprocating tubular actuating member 58, and the ultrasonic transmission waveguide 78 are mechanically engaged by a pin 74. The switch assembly 28 comprises the toggle switch 30 and electrical elements 86a,b to electrically energize the ultrasonic transducer 16 in accordance with the activation of the first or second projecting knobs 30a, 30b.

In one example embodiment, the outer tubular sheath 56 isolates the user or the patient from the ultrasonic vibrations of the ultrasonic transmission waveguide 78. The outer tubular sheath 56 generally includes a hub 76. The outer tubular sheath 56 is threaded onto the distal end of the handle assembly 12. The ultrasonic transmission waveguide 78 extends through the opening of the outer tubular sheath 56 and the isolation elements 82 isolate the ultrasonic transmission waveguide 78 from the outer tubular sheath 56. The outer tubular sheath 56 may be attached to the waveguide 78 with the pin 74. The hole to receive the pin 74 in the waveguide 78 may occur nominally at a displacement node. The waveguide 78 may screw or snap into the hand piece handle assembly 12 by a stud. Flat portions on the hub 76 may allow the assembly to be torqued to a required level.

In one example embodiment, the hub 76 portion of the outer tubular sheath 56 is preferably constructed from plastic and the tubular elongated portion of the outer tubular sheath 56 is fabricated from stainless steel. Alternatively, the ultrasonic transmission waveguide 78 may comprise polymeric material surrounding it to isolate it from outside contact.

In one example embodiment, the distal end of the ultrasonic transmission waveguide 78 may be coupled to the proximal end of the blade 66 by an internal threaded connection, preferably at or near an antinode. It is contemplated that the blade 66 may be attached to the ultrasonic transmission waveguide 78 by any suitable means, such as a welded joint or the like. Although the blade 66 may be detachable from the ultrasonic transmission waveguide 78, it is also contemplated that the single element end effector (e.g., the blade 66) and the ultrasonic transmission waveguide 78 may be formed as a single unitary piece.

In one example embodiment, the trigger 32 is coupled to a linkage mechanism to translate the rotational motion of the trigger 32 in directions 33A and 33B to the linear motion of the reciprocating tubular actuating member 58 in corresponding directions 60A and 60B. The trigger 32 comprises a first set of flanges 97 with openings formed therein to receive a first yoke pin 94a. The first yoke pin 94a is also located through a set of openings formed at the distal end of the yoke 84. The trigger 32 also comprises a second set of flanges 96 to receive a first end 92a of a link 92. A trigger pin 90 is received in openings formed in the link 92 and the second set of flanges 96. The trigger pin 90 is received in the openings formed in the link 92 and the second set of flanges 96 and is adapted to couple to the first and second portions 12a, 12b of the handle assembly 12 to form a trigger pivot point for the trigger 32. A second end 92b of the link 92 is received in a slot 93 formed in a proximal end of the yoke 84 and is retained therein by a second yoke pin 94b. As the trigger 32 is pivotally rotated about the pivot point 190 formed by the trigger pin 90, the yoke translates horizontally along longitudinal axis "T" in a direction indicated by arrows 60A,B.

Figure 8:
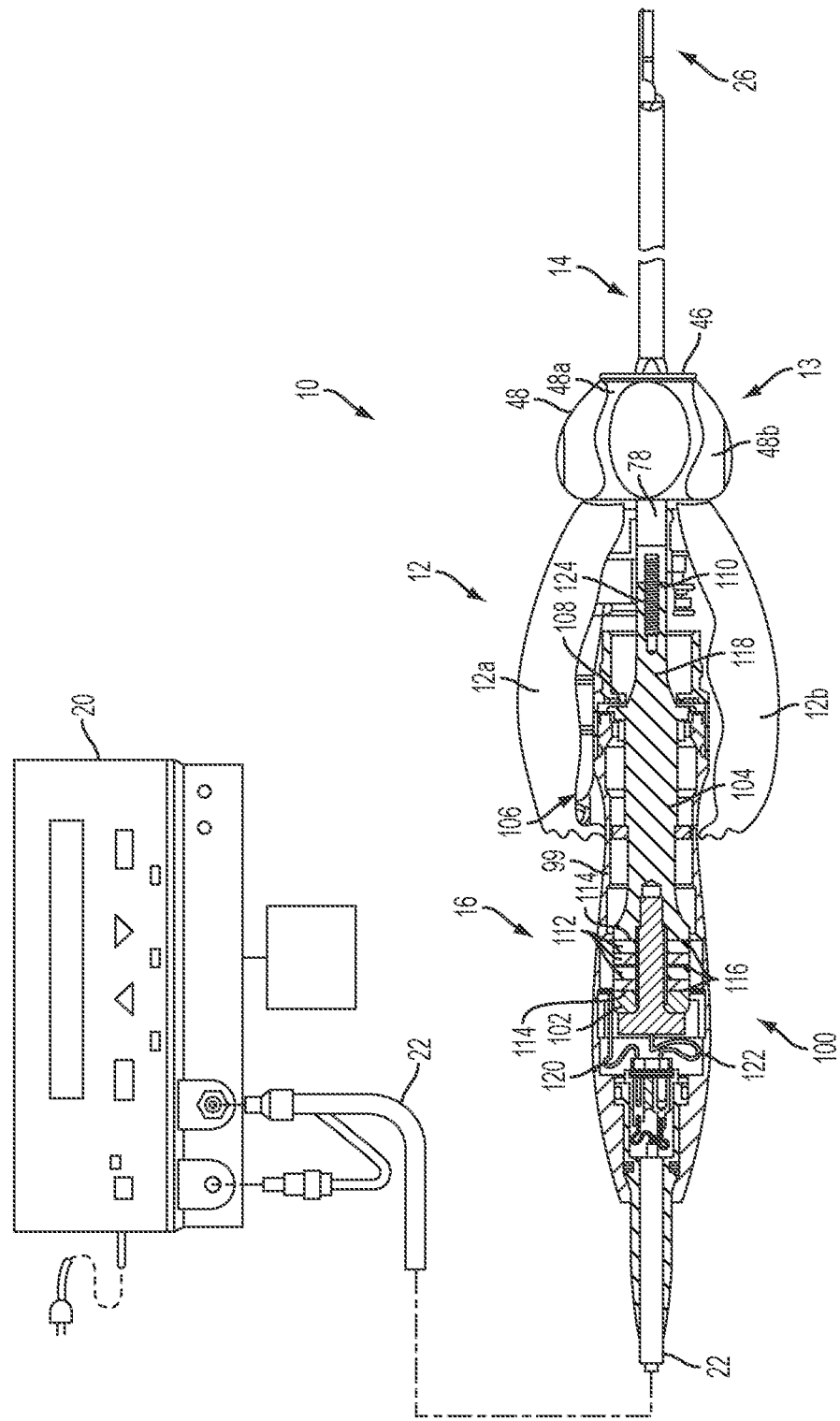
FIG. 8 illustrates a top view of one embodiment of a surgical system including a surgical instrument and an ultrasonic generator.

FIG. 8 illustrates one example embodiment of an ultrasonic surgical instrument 10. In the illustrated embodiment, a cross-sectional view of the ultrasonic transducer 16 is shown within a partial cutaway view of the handle assembly 12. One example embodiment of the ultrasonic surgical instrument 10 comprises the ultrasonic signal generator 20 coupled to the ultrasonic transducer 16, comprising a hand piece housing 99, and an ultrasonically actuatable single or multiple element end effector assembly 26. As previously discussed, the end effector assembly 26 comprises the ultrasonically actuatable blade 66 and the clamp arm 64. The ultrasonic transducer 16, which is known as a "Langevin stack", generally includes a transduction portion 100, a first resonator portion or end-bell 102, and a second resonator portion or fore-bell 104, and ancillary components. The total construction of these components is a resonator. The ultrasonic transducer 16 is preferably an integral number of one-half system wavelengths ($n\lambda/2$; where "n" is any positive integer; e.g., n=1, 2, 3 . . . ) in length as will be described in more detail later. An acoustic assembly 106 includes the ultrasonic transducer 16, a nose cone 108, a velocity transformer 118, and a surface 110.

In one example embodiment, the distal end of the end-bell 102 is connected to the proximal end of the transduction portion 100, and the proximal end of the fore-bell 104 is connected to the distal end of the transduction portion 100. The fore-bell 104 and the end-bell 102 have a length determined by a number of variables, including the thickness of the transduction portion 100, the density and modulus of elasticity of the material used to manufacture the end-bell 102 and the fore-bell 22, and the resonant frequency of the ultrasonic transducer 16. The fore-bell 104 may be tapered inwardly from its proximal end to its distal end to amplify the ultrasonic vibration amplitude as the velocity transformer 118, or alternately may have no amplification. A suitable vibrational frequency range may be about 20 Hz to 32 kHz and a well-suited vibrational frequency range may be about 30-10 kHz. A suitable operational vibrational frequency may be approximately 55.5 kHz, for example.

In one example embodiment, the piezoelectric elements 112 may be fabricated from any suitable material, such as, for example, lead zirconate-titanate, lead meta-niobate, lead titanate, barium titanate, or other piezoelectric ceramic material. Each of positive electrodes 114, negative electrodes 116, and the piezoelectric elements 112 has a bore extending through the center. The positive and negative electrodes 114 and 116 are electrically coupled to wires 120 and 122, respectively. The wires 120 and 122 are encased within the cable 22 and electrically connectable to the ultrasonic signal generator 20.

The ultrasonic transducer 16 of the acoustic assembly 106 converts the electrical signal from the ultrasonic signal generator 20 into mechanical energy that results in primarily a standing acoustic wave of longitudinal vibratory motion of the ultrasonic transducer 16 and the blade 66 portion of the end effector assembly 26 at ultrasonic frequencies. In another embodiment, the vibratory motion of the ultrasonic transducer may act in a different direction. For example, the vibratory motion may comprise a local longitudinal component of a more complicated motion of the tip of the elongated shaft assembly 14. A suitable generator is available as model number GEN11, from Ethicon Endo-Surgery, Inc., Cincinnati, Ohio. When the acoustic assembly 106 is energized, a vibratory motion standing wave is generated through the acoustic assembly 106. The ultrasonic surgical instrument 10 is designed to operate at a resonance such that an acoustic standing wave pattern of predetermined amplitude is produced. The amplitude of the vibratory motion at any point along the acoustic assembly 106 depends upon the location along the acoustic assembly 106 at which the vibratory motion is measured. A minimum or zero crossing in the vibratory motion standing wave is generally referred to as a node (i.e., where motion is minimal), and a local absolute value maximum or peak in the standing wave is generally referred to as an anti-node (e.g., where local motion is maximal). The distance between an anti-node and its nearest node is one-quarter wavelength ($\lambda/4$).

The wires 120 and 122 transmit an electrical signal from the ultrasonic signal generator 20 to the positive electrodes 114 and the negative electrodes 116. The piezoelectric elements 112 are energized by the electrical signal supplied from the ultrasonic signal generator 20 in response to an actuator 224, such as a foot switch, for example, to produce an acoustic standing wave in the acoustic assembly 106. The electrical signal causes disturbances in the piezoelectric elements 112 in the form of repeated small displacements resulting in large alternating compression and tension forces within the material. The repeated small displacements cause the piezoelectric elements 112 to expand and contract in a continuous manner along the axis of the voltage gradient, producing longitudinal waves of ultrasonic energy. The ultrasonic energy is transmitted through the acoustic assembly 106 to the blade 66 portion of the end effector assembly 26 via a transmission component or an ultrasonic transmission waveguide portion 78 of the elongated shaft assembly 14.

In one example embodiment, in order for the acoustic assembly 106 to deliver energy to the blade 66 portion of the end effector assembly 26, all components of the acoustic assembly 106 must be acoustically coupled to the blade 66. The distal end of the ultrasonic transducer 16 may be acoustically coupled at the surface 110 to the proximal end of the ultrasonic transmission waveguide 78 by a threaded connection such as a stud 124.

In one example embodiment, the components of the acoustic assembly 106 are preferably acoustically tuned such that the length of any assembly is an integral number of one-half wavelengths ($n\lambda/2$), where the wavelength $\lambda$ is the wavelength of a pre-selected or operating longitudinal vibration drive frequency $f_d$ of the acoustic assembly 106. It is also contemplated that the acoustic assembly 106 may incorporate any suitable arrangement of acoustic elements.

In one example embodiment, the blade 66 may have a length substantially equal to an integral multiple of one-half system wavelengths ($n\lambda/2$). A distal end of the blade 66 may be disposed near an antinode in order to provide the maximum longitudinal excursion of the distal end. When the transducer assembly is energized, the distal end of the blade 66 may be configured to move in the range of, for example, approximately 10 to 500 microns peak-to-peak, and preferably in the range of about 30 to 64 microns at a predetermined vibrational frequency of 55 kHz, for example.

In one example embodiment, the blade 66 may be coupled to the ultrasonic transmission waveguide 78. The blade 66 and the ultrasonic transmission waveguide 78 as illustrated are formed as a single unit construction from a material suitable for transmission of ultrasonic energy. Examples of such materials include Ti6Al4V (an alloy of Titanium including Aluminum and Vanadium), Aluminum, Stainless Steel, or other suitable materials. Alternately, the blade 66 may be separable (and of differing composition) from the ultrasonic transmission waveguide 78, and coupled by, for example, a stud, weld, glue, quick connect, or other suitable known methods. The length of the ultrasonic transmission waveguide 78 may be substantially equal to an integral number of one-half wavelengths ($n\lambda/2$), for example. The ultrasonic transmission waveguide 78 may be preferably fabricated from a solid core shaft constructed out of material suitable to propagate ultrasonic energy efficiently, such as the titanium alloy discussed above (i.e., Ti6Al4V) or any suitable aluminum alloy, or other alloys, for example.

In one example embodiment, the ultrasonic transmission waveguide 78 comprises a longitudinally projecting attachment post at a proximal end to couple to the surface 110 of the ultrasonic transmission waveguide 78 by a threaded connection such as the stud 124. The ultrasonic transmission waveguide 78 may include a plurality of stabilizing silicone rings or compliant supports 82 (FIG. 5) positioned at a plurality of nodes. The silicone rings 82 dampen undesirable vibration and isolate the ultrasonic energy from an outer protective sheath 80 (FIG. 5) assuring the flow of ultrasonic energy in a longitudinal direction to the distal end of the blade 66 with maximum efficiency.

Figure 9:
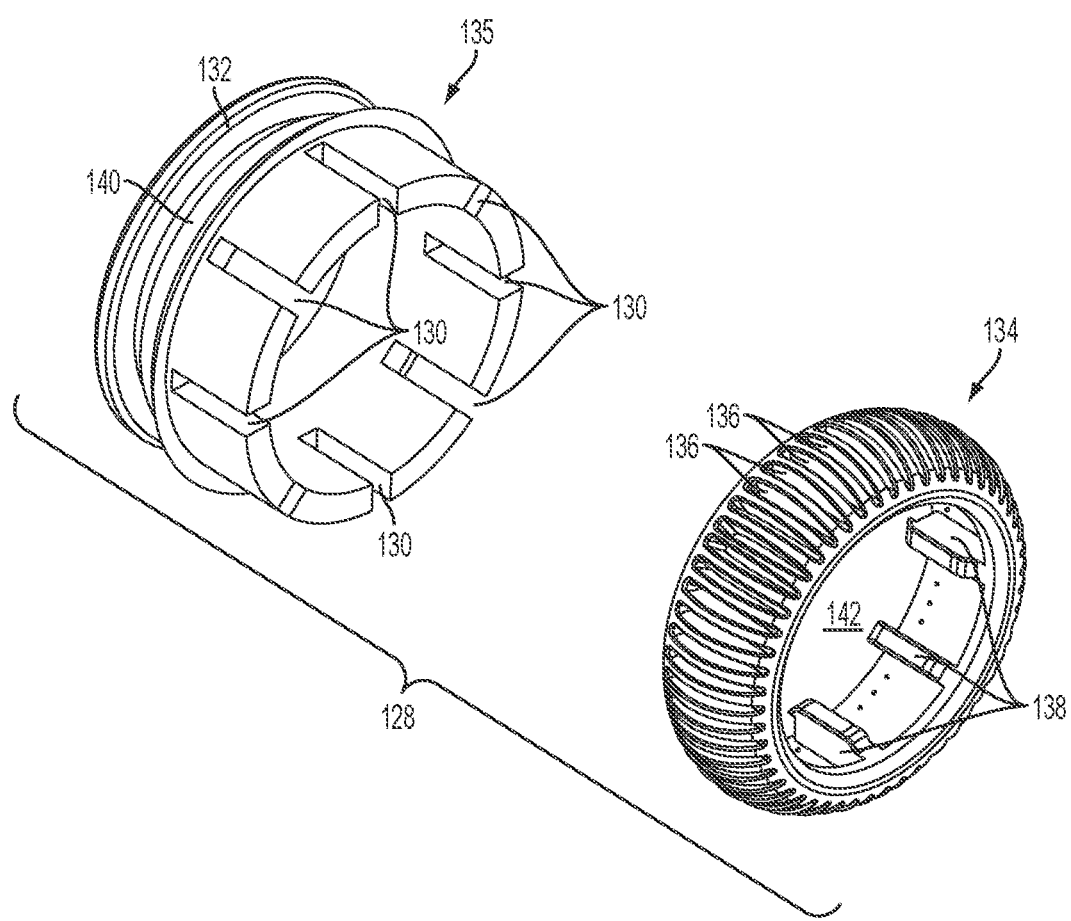
FIG. 9 illustrates one embodiment of a rotation assembly included in one example embodiment of the surgical instrument of FIG. 1.

FIG. 9 illustrates one example embodiment of the proximal rotation assembly 128. In the illustrated embodiment, the proximal rotation assembly 128 comprises the proximal rotation knob 134 inserted over the cylindrical hub 135. The proximal rotation knob 134 comprises a plurality of radial projections 138 that are received in corresponding slots 130 formed on a proximal end of the cylindrical hub 135. The proximal rotation knob 134 defines an opening 142 to receive the distal end of the ultrasonic transducer 16. The radial projections 138 are formed of a soft polymeric material and define a diameter that is undersized relative to the outside diameter of the ultrasonic transducer 16 to create a friction interference fit when the distal end of the ultrasonic transducer 16. The polymeric radial projections 138 protrude radially into the opening 142 to form "gripper" ribs that firmly grip the exterior housing of the ultrasonic transducer 16. Therefore, the proximal rotation knob 134 securely grips the ultrasonic transducer 16.

The distal end of the cylindrical hub 135 comprises a circumferential lip 132 and a circumferential bearing surface 140. The circumferential lip engages a groove formed in the housing 12 and the circumferential bearing surface 140 engages the housing 12. Thus, the cylindrical hub 135 is mechanically retained within the two housing portions (not shown) of the housing 12. The circumferential lip 132 of the cylindrical hub 135 is located or "trapped" between the first and second housing portions 12a, 12b and is free to rotate in place within the groove. The circumferential bearing surface 140 bears against interior portions of the housing to assist proper rotation. Thus, the cylindrical hub 135 is free to rotate in place within the housing. The user engages the flutes 136 formed on the proximal rotation knob 134 with either the finger or the thumb to rotate the cylindrical hub 135 within the housing 12.

In one example embodiment, the cylindrical hub 135 may be formed of a durable plastic such as polycarbonate. In one example embodiment, the cylindrical hub 135 may be formed of a siliconized polycarbonate material. In one example embodiment, the proximal rotation knob 134 may be formed of pliable, resilient, flexible polymeric materials including Versaflex® TPE alloys made by GLS Corporation, for example. The proximal rotation knob 134 may be formed of elastomeric materials, thermoplastic rubber known as Santoprene®, other thermoplastic vulcanizates (TPVs), or elastomers, for example. The embodiments, however, are not limited in this context.

Figure 10:
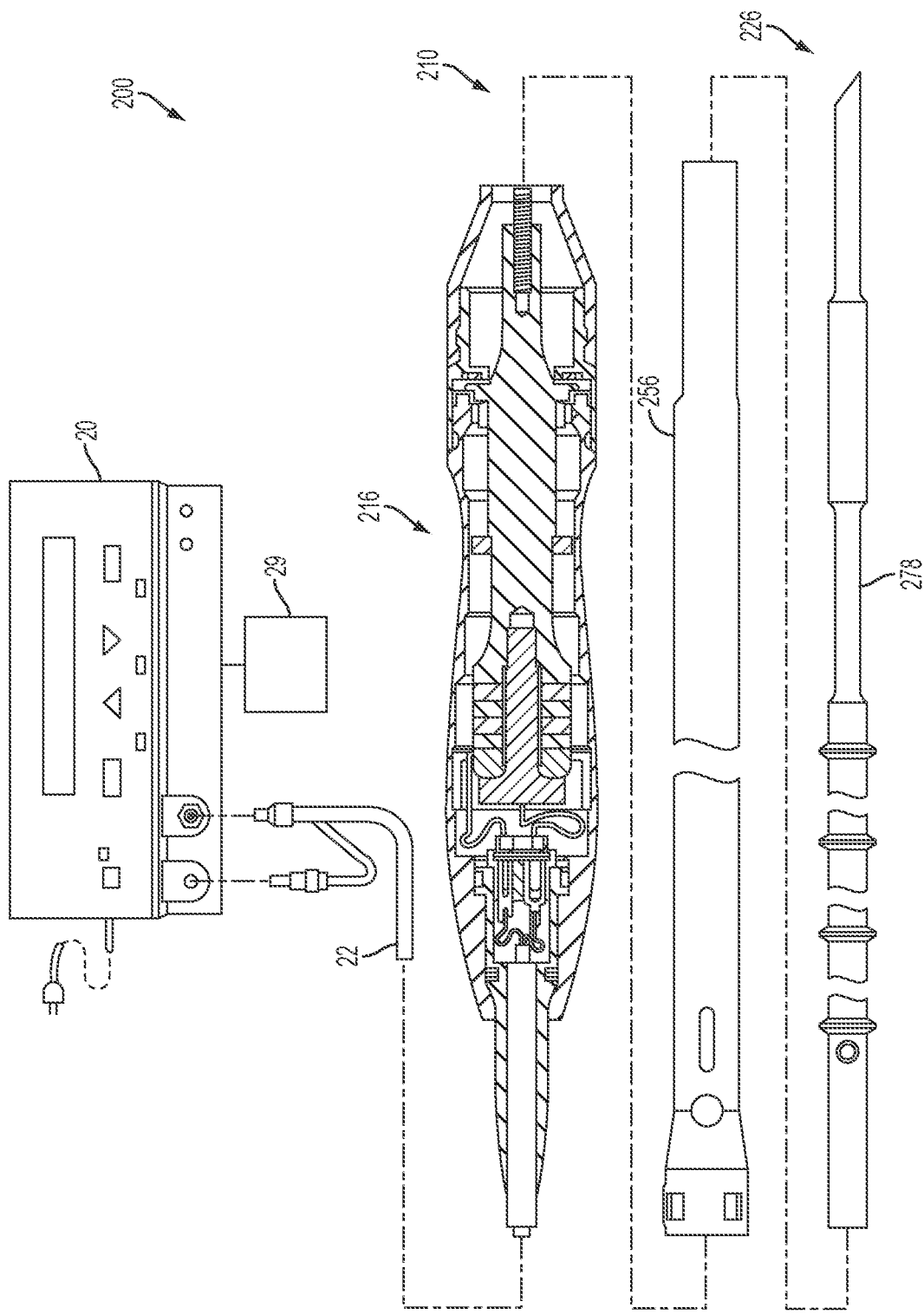
FIG. 10 illustrates one embodiment of a surgical system including a surgical instrument having a single element end effector.

FIG. 10 illustrates one example embodiment of a surgical system 200 including a surgical instrument 210 having single element end effector 278. The system 200 may include a transducer assembly 216 coupled to the end effector 278 and a sheath 256 positioned around the proximal portions of the end effector 278 as shown. The transducer assembly 216 and end effector 278 may operate in a manner similar to that of the transducer assembly 16 and end effector 18 described above to produce ultrasonic energy that may be transmitted to tissue via blade 226.

Figure 11:
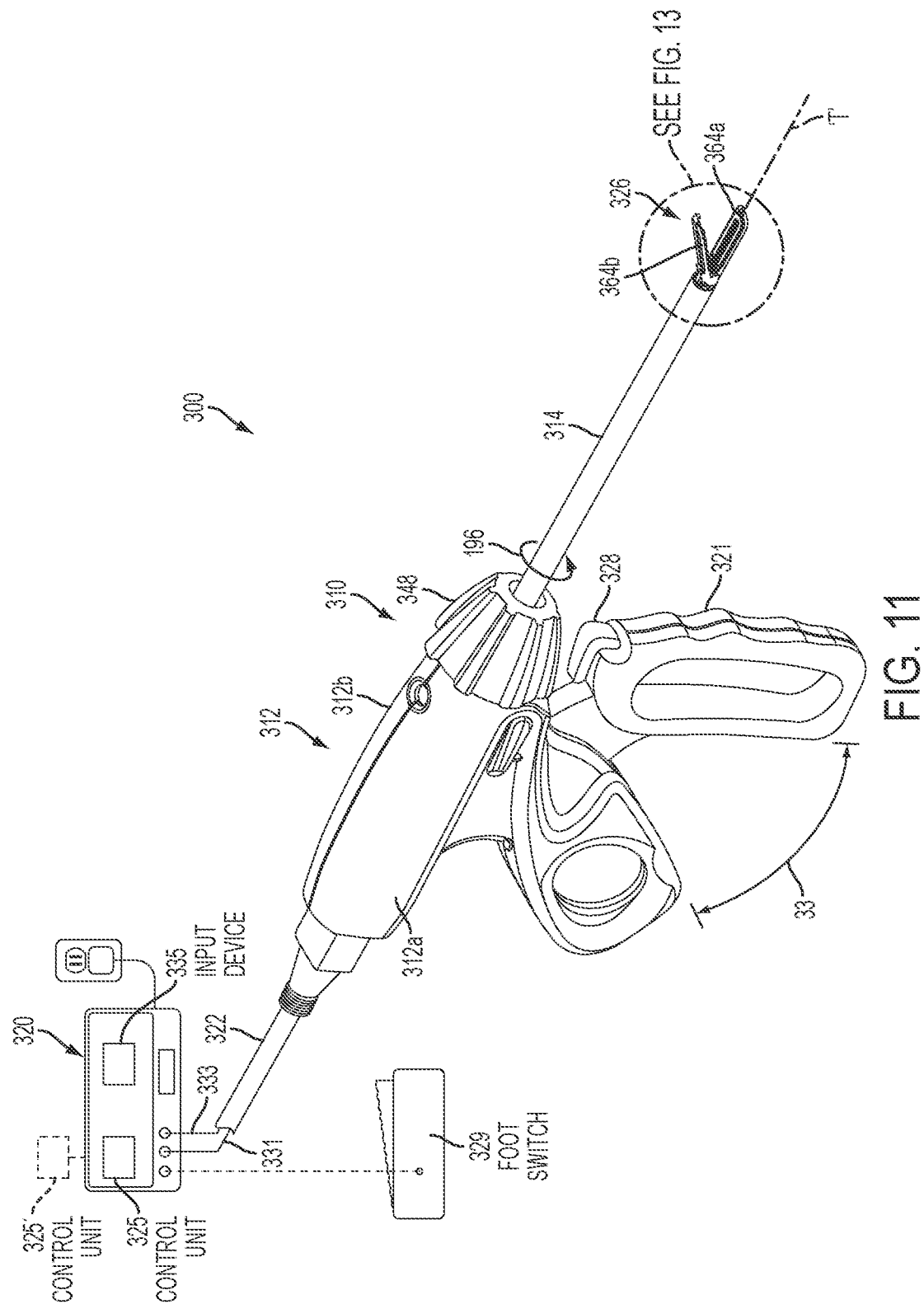
FIG. 11 is a perspective view of one embodiment of an electrical energy surgical instrument.

FIGS. 11-18C illustrate various embodiments of surgical instruments that utilize therapeutic and/or sub-therapeutic electrical energy to treat and/or destroy tissue or provide feedback to the generators (e.g., electrosurgical instruments). The embodiments of FIGS. 11-18C are adapted for use in a manual or hand-operated manner, although electrosurgical instruments may be utilized in robotic applications as well. FIG. 11 is a perspective view of one example embodiment of a surgical instrument system 300 comprising an electrical energy surgical instrument 310. The electrosurgical instrument 310 may comprise a proximal handle 312, a distal working end or end effector 326 and an introducer or elongated shaft 314 disposed in-between.

The electrosurgical system 300 can be configured to supply energy, such as electrical energy, ultrasonic energy, heat energy, or any combination thereof, to the tissue of a patient either independently or simultaneously as described, for example, in connection with FIG. 1, for example. In one example embodiment, the electrosurgical system 300 includes a generator 320 in electrical communication with the electrosurgical instrument 310. The generator 320 is connected to electrosurgical instrument 310 via a suitable transmission medium such as a cable 322. In one example embodiment, the generator 320 is coupled to a controller, such as a control unit 325, for example. In various embodiments, the control unit 325 may be formed integrally with the generator 320 or may be provided as a separate circuit module or device electrically coupled to the generator 320 (shown in phantom as 325' to illustrate this option). Although in the presently disclosed embodiment, the generator 320 is shown separate from the electrosurgical instrument 310, in one example embodiment, the generator 320 (and/or the control unit 325) may be formed integrally with the electrosurgical instrument 310 to form a unitary electrosurgical system 300, where a battery located within the electrosurgical instrument 310 is the energy source and a circuit coupled to the battery produces the suitable electrical energy, ultrasonic energy, or heat energy. One such example is described herein below in connection with FIGS. 17-18C.

The generator 320 may comprise an input device 335 located on a front panel of the generator 320 console. The input device 335 may comprise any suitable device that generates signals suitable for programming the operation of the generator 320, such as a keyboard, or input port, for example. In one example embodiment, various electrodes in the first jaw 364A and the second jaw 364B may be coupled to the generator 320. The cable 322 may comprise multiple electrical conductors for the application of electrical energy to positive (+) and negative (−) electrodes of the electrosurgical instrument 310. The control unit 325 may be used to activate the generator 320, which may serve as an electrical source. In various embodiments, the generator 320 may comprise an RF source, an ultrasonic source, a direct current source, and/or any other suitable type of electrical energy source, for example, which may be activated independently or simultaneously.

In various embodiments, the electrosurgical system 300 may comprise at least one supply conductor 331 and at least one return conductor 333, wherein current can be supplied to electrosurgical instrument 300 via the supply conductor 331 and wherein the current can flow back to the generator 320 via the return conductor 333. In various embodiments, the supply conductor 331 and the return conductor 333 may comprise insulated wires and/or any other suitable type of conductor. In certain embodiments, as described below, the supply conductor 331 and the return conductor 333 may be contained within and/or may comprise the cable 322 extending between, or at least partially between, the generator 320 and the end effector 326 of the electrosurgical instrument 310. In any event, the generator 320 can be configured to apply a sufficient voltage differential between the supply conductor 331 and the return conductor 333 such that sufficient current can be supplied to the end effector 110.

Figure 12:
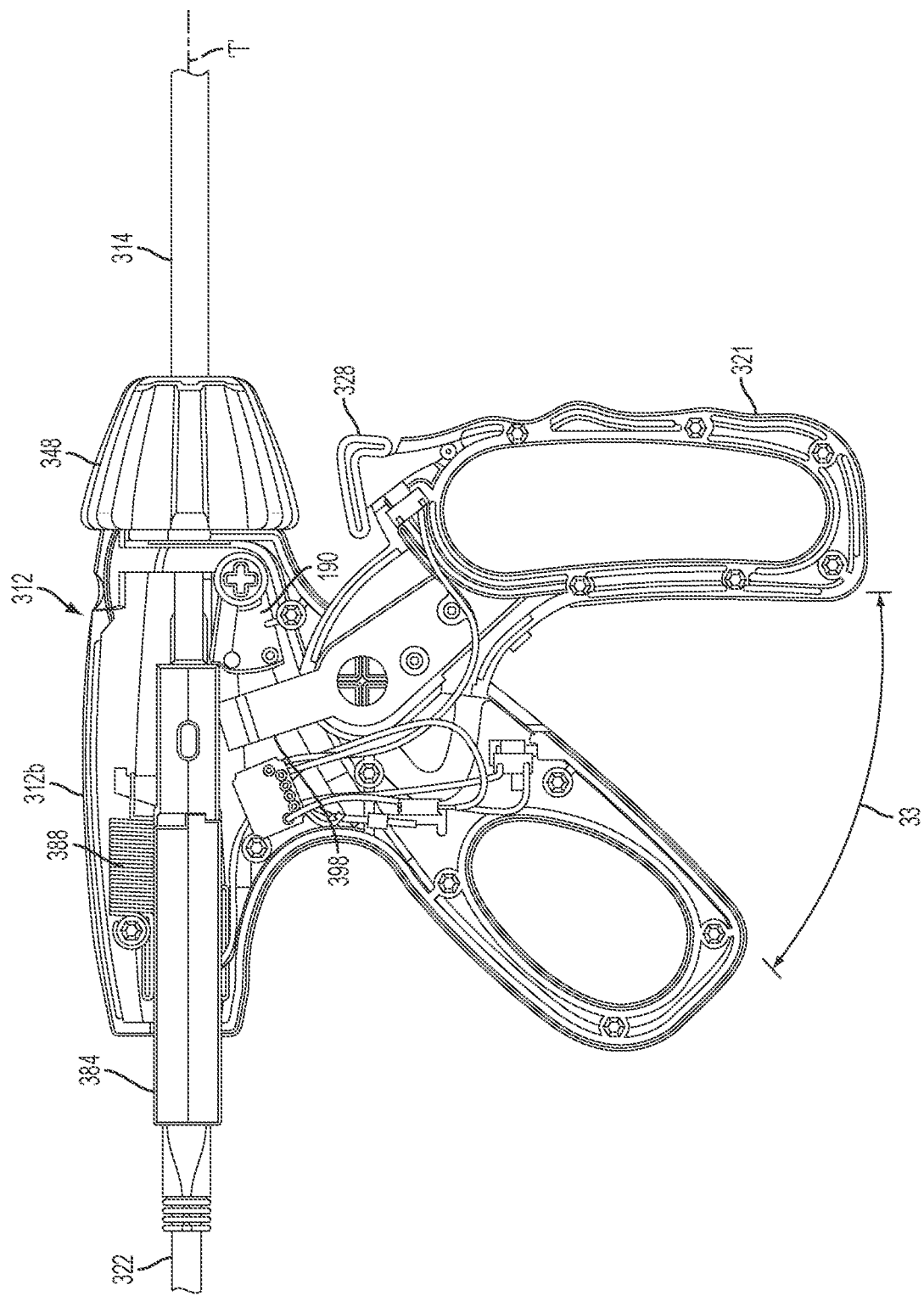
FIG. 12 is a side view of a handle of one embodiment of the surgical instrument of FIG. 11 with a half of a handle body removed to illustrate some of the components therein.

FIG. 12 is a side view of one example embodiment of the handle 312 of the surgical instrument 310. In FIG. 12, the handle 312 is shown with half of a first handle body 312A (see FIG. 11) removed to illustrate various components within second handle body 312B. The handle 312 may comprise a lever arm 321 (e.g., a trigger) which may be pulled along a path 33. The lever arm 321 may be coupled to an axially moveable member 378 (FIGS. 13-16) disposed within elongated shaft 314 by a shuttle 384 operably engaged to an extension 398 of lever arm 321. The shuttle 384 may further be connected to a biasing device, such as a spring 388, which may also be connected to the second handle body 312B, to bias the shuttle 384 and thus the axially moveable member 378 in a proximal direction, thereby urging the jaws 364A and 364B to an open position as seen in FIG. 11. Also, referring to FIGS. 11-12, a locking member 190 (see FIG. 12) may be moved by a locking switch 328 (see FIG. 11) between a locked position, where the shuttle 384 is substantially prevented from moving distally as illustrated, and an unlocked position, where the shuttle 384 may be allowed to freely move in the distal direction, toward the elongated shaft 314. In some embodiments, the locking switch 328 may be implemented as a button. The handle 312 can be any type of pistol-grip or other type of handle known in the art that is configured to carry actuator levers, triggers or sliders for actuating the first jaw 364A and the second jaw 364B. The elongated shaft 314 may have a cylindrical or rectangular cross-section, for example, and can comprise a thin-wall tubular sleeve that extends from handle 312. The elongated shaft 314 may include a bore extending therethrough for carrying actuator mechanisms, for example, the axially moveable member 378, for actuating the jaws and for carrying electrical leads for delivery of electrical energy to electrosurgical components of the end effector 326.

The end effector 326 may be adapted for capturing and transecting tissue and for the contemporaneously welding the captured tissue with controlled application of energy (e.g., RF energy). The first jaw 364A and the second jaw 364B may close to thereby capture or engage tissue about a longitudinal axis "T" defined by the axially moveable member 378. The first jaw 364A and second jaw 364B may also apply compression to the tissue. In some embodiments, the elongated shaft 314, along with first jaw 364A and second jaw 364B, can be rotated a full 360° degrees, as shown by arrow 196 (see FIG. 11), relative to handle 312. For example, a rotation knob 348 may be rotatable about the longitudinal axis of the shaft 314 and may be coupled to the shaft 314 such that rotation of the knob 348 causes corresponding rotation of the shaft 314. The first jaw 364A and the second jaw 364B can remain openable and/or closeable while rotated.

Figure 13:
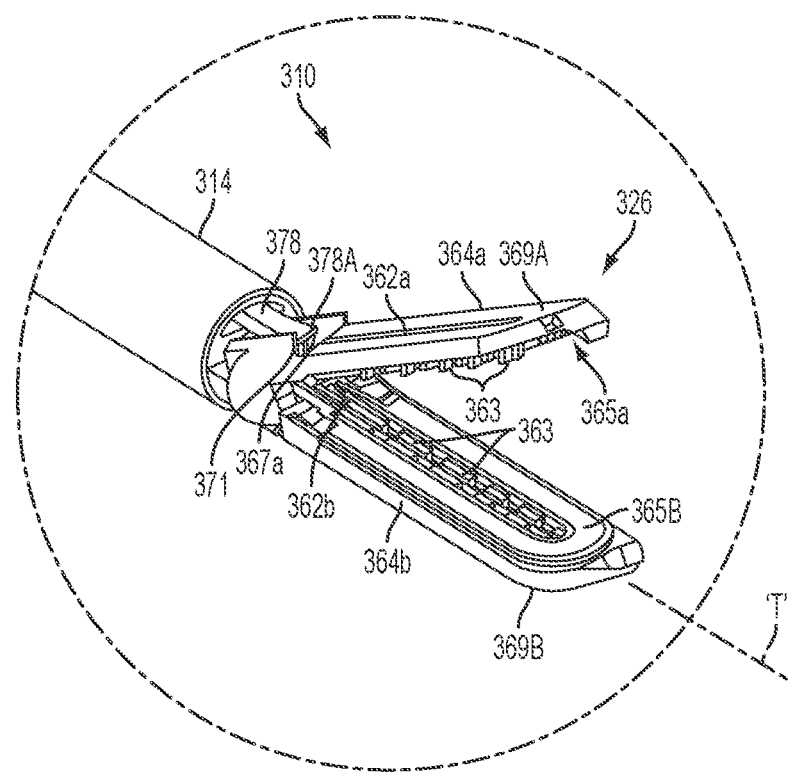
FIG. 13 illustrates a perspective view of one embodiment of the end effector of the surgical instrument of FIG. 11 with the jaws open and the distal end of an axially movable member in a retracted position.
Figure 14:
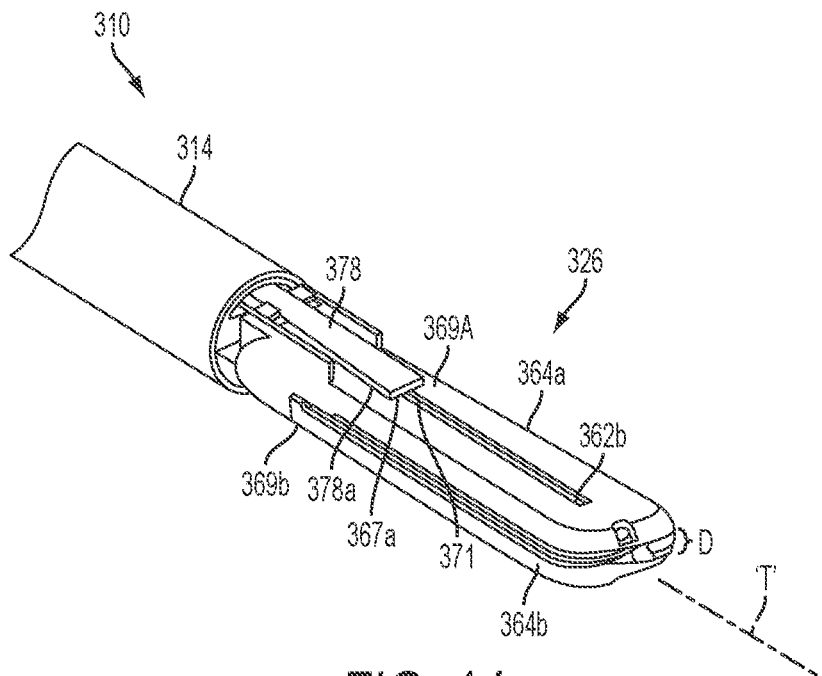
FIG. 14 illustrates a perspective view of one embodiment of the end effector of the surgical instrument of FIG. 11 with the jaws closed and the distal end of an axially movable member in a partially advanced position.

FIG. 13 shows a perspective view of one example embodiment of the end effector 326 with the jaws 364A, 364B open, while FIG. 14 shows a perspective view of one example embodiment of the end effector 326 with the jaws 364A, 364B closed. As noted above, the end effector 326 may comprise the upper first jaw 364A and the lower second jaw 364B, which may be straight or curved. The first jaw 364A and the second jaw 364B may each comprise an elongated slot or channel 362A and 362B, respectively, disposed outwardly along their respective middle portions. Further, the first jaw 364A and second jaw 364B may each have tissue-gripping elements, such as teeth 363, disposed on the inner portions of first jaw 364A and second jaw 364B. The first jaw 364A may comprise an upper first outward-facing surface 369A and an upper first energy delivery surface 365A. The second jaw 364B may comprise a lower second outward-facing surface 369B and a lower second energy delivery surface 365B. The first energy delivery surface 365A and the second energy delivery surface 365B may both extend in a "U" shape about the distal end of the end effector 326.

Figure 15:
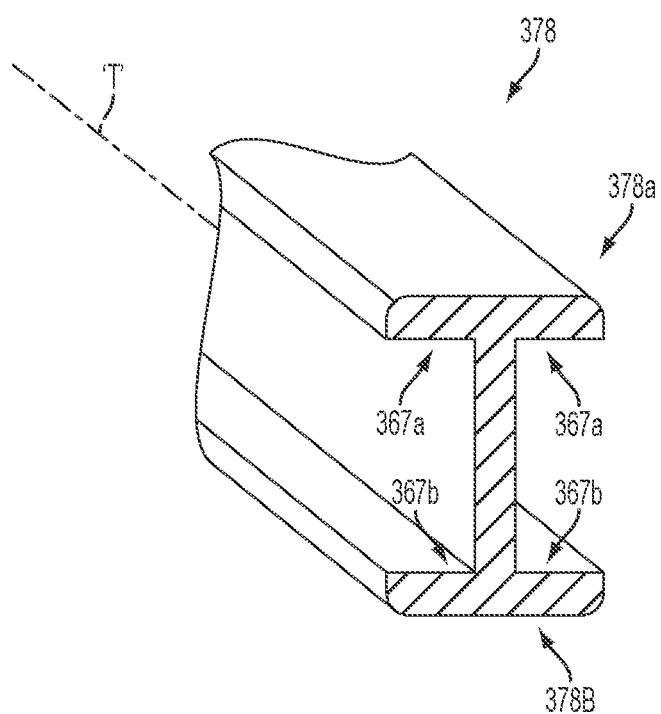
FIG. 15 illustrates a perspective view of one embodiment of the axially moveable member of the surgical instrument of FIG. 11.

The lever arm 321 of the handle 312 (FIG. 12) may be adapted to actuate the axially moveable member 378, which may also function as a jaw-closing mechanism. For example, the axially moveable member 378 may be urged distally as the lever arm 321 is pulled proximally along the path 33 via the shuttle 384, as shown in FIG. 12 and discussed above. FIG. 15 is a perspective view of one example embodiment of the axially moveable member 378 of the surgical instrument 310. The axially moveable member 378 may comprise one or several pieces, but in any event, may be movable or translatable with respect to the elongated shaft 314 and/or the jaws 364A, 364B. Also, in at least one example embodiment, the axially moveable member 378 may be made of 17-4 precipitation hardened stainless steel. The distal end of axially moveable member 378 may comprise a flanged "I"-beam configured to slide within the channels 362A and 362B in jaws 364A and 364B. The axially moveable member 378 may slide within the channels 362A, 362B to open and close the first jaw 364A and the second jaw 364B. The distal end of the axially moveable member 378 may also comprise an upper flange or "c"-shaped portion 378A and a lower flange or "c"-shaped portion 378B. The flanges 378A and 378B respectively define inner cam surfaces 367A and 367B for engaging outward facing surfaces of the first jaw 364A and the second jaw 364B. The opening-closing of jaws 364A and 364B can apply very high compressive forces on tissue using cam mechanisms which may include movable "I-beam" axially moveable member 378 and the outward facing surfaces 369A, 369B of jaws 364A, 364B.

More specifically, referring now to FIGS. 13-15, collectively, the inner cam surfaces 367A and 367B of the distal end of axially moveable member 378 may be adapted to slidably engage the first outward-facing surface 369A and the second outward-facing surface 369B of the first jaw 364A and the second jaw 364B, respectively. The channel 362A within first jaw 364A and the channel 362B within the second jaw 364B may be sized and configured to accommodate the movement of the axially moveable member 378, which may comprise a tissue-cutting element 371, for example, comprising a sharp distal edge. FIG. 14, for example, shows the distal end of the axially moveable member 378 advanced at least partially through channels 362A and 362B (FIG. 13). The advancement of the axially moveable member 378 may close the end effector 326 from the open configuration shown in FIG. 13. In the closed position shown by FIG. 14, the upper first jaw 364A and lower second jaw 364B define a gap or dimension D between the first energy delivery surface 365A and second energy delivery surface 365B of first jaw 364A and second jaw 364B, respectively. In various embodiments, dimension D can equal from about 0.0005" to about 0.040", for example, and in some embodiments, between about 0.001" to about 0.010", for example. Also, the edges of the first energy delivery surface 365A and the second energy delivery surface 365B may be rounded to prevent the dissection of tissue.

Figure 16:
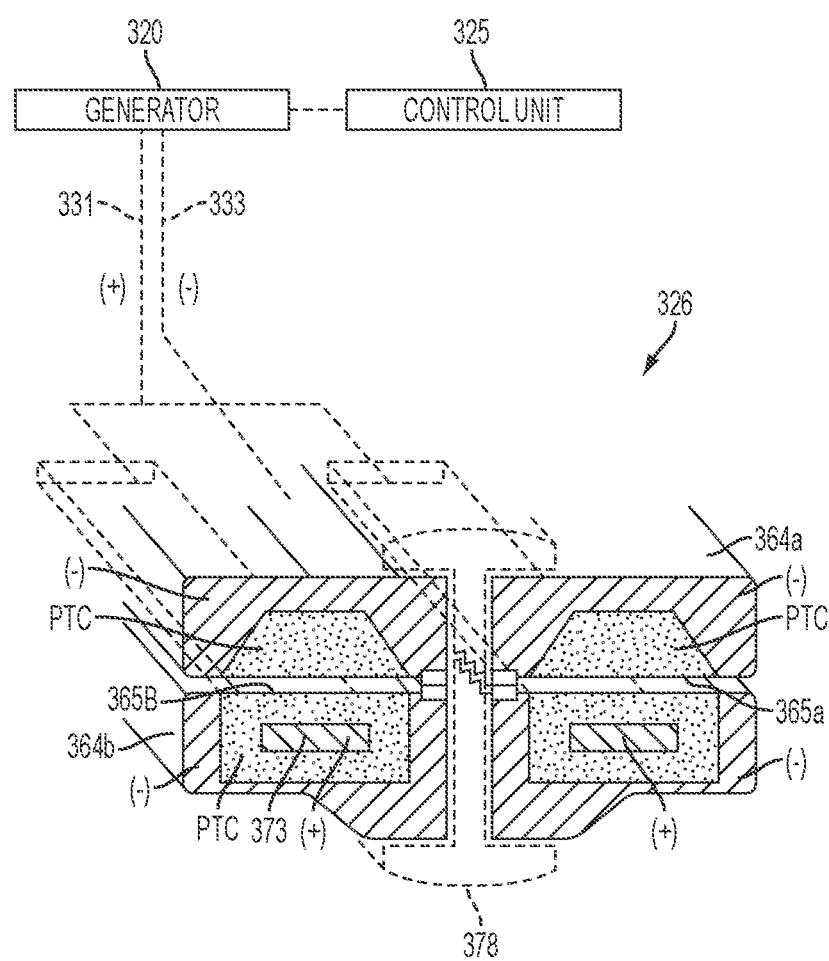
FIG. 16 illustrates a section view of one embodiment of the end effector of the surgical instrument of FIG. 11.

FIG. 16 is a section view of one example embodiment of the end effector 326 of the surgical instrument 310. The engagement, or tissue-contacting, surface 365B of the lower jaw 364B is adapted to deliver energy to tissue, at least in part, through a conductive-resistive matrix, such as a variable resistive positive temperature coefficient (PTC) body, as discussed in more detail below. At least one of the upper and lower jaws 364A, 364B may carry at least one electrode 373 configured to deliver the energy from the generator 320 to the captured tissue. The engagement, or tissue-contacting, surface 365A of upper jaw 364A may carry a similar conductive-resistive matrix (i.e., a PTC material), or in some embodiments the surface may be a conductive electrode or an insulative layer, for example. Alternatively, the engagement surfaces of the jaws can carry any of the energy delivery components disclosed in U.S. Pat. No. 6,773,409, filed Oct. 22, 2001, entitled ELECTROSURGICAL JAW STRUCTURE FOR CONTROLLED ENERGY DELIVERY, the entire disclosure of which is incorporated herein by reference.

The first energy delivery surface 365A and the second energy delivery surface 365B may each be in electrical communication with the generator 320. The first energy delivery surface 365A and the second energy delivery surface 365B may be configured to contact tissue and deliver electrosurgical energy to captured tissue which are adapted to seal or weld the tissue. The control unit 325 regulates the electrical energy delivered by electrical generator 320 which in turn delivers electrosurgical energy to the first energy delivery surface 365A and the second energy delivery surface 365B. The energy delivery may be initiated by an activation button 328 (FIG. 12) operably engaged with the lever arm 321 and in electrical communication with the generator 320 via cable 322. In one example embodiment, the electrosurgical instrument 310 may be energized by the generator 320 by way of a foot switch 329 (FIG. 11). When actuated, the foot switch 329 triggers the generator 320 to deliver electrical energy to the end effector 326, for example. The control unit 325 may regulate the power generated by the generator 320 during activation. Although the foot switch 329 may be suitable in many circumstances, other suitable types of switches can be used.

As mentioned above, the electrosurgical energy delivered by electrical generator 320 and regulated, or otherwise controlled, by the control unit 325 may comprise radio frequency (RF) energy, or other suitable forms of electrical energy. Further, the opposing first and second energy delivery surfaces 365A and 365B may carry variable resistive positive temperature coefficient (PTC) bodies that are in electrical communication with the generator 320 and the control unit 325. Additional details regarding electrosurgical end effectors, jaw closing mechanisms, and electrosurgical energy-delivery surfaces are described in the following U.S. patents and published patent applications: U.S. Pat. Nos. 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,312; and U.S. Pat. App. Pub. Nos. 2010/0036370 and 2009/0076506, all of which are incorporated herein in their entirety by reference and made a part of this specification.

In one example embodiment, the generator 320 may be implemented as an electrosurgery unit (ESU) capable of supplying power sufficient to perform bipolar electrosurgery using radio frequency (RF) energy. In one example embodiment, the ESU can be a bipolar ERBE ICC 350 sold by ERBE USA, Inc. of Marietta, Georgia. In some embodiments, such as for bipolar electrosurgery applications, a surgical instrument having an active electrode and a return electrode can be utilized, wherein the active electrode and the return electrode can be positioned against, adjacent to and/or in electrical communication with, the tissue to be treated such that current can flow from the active electrode, through the positive temperature coefficient (PTC) bodies and to the return electrode through the tissue. Thus, in various embodiments, the electrosurgical system 300 may comprise a supply path and a return path, wherein the captured tissue being treated completes, or closes, the circuit. In one example embodiment, the generator 320 may be a monopolar RF ESU and the electrosurgical instrument 310 may comprise a monopolar end effector 326 in which one or more active electrodes are integrated. For such a system, the generator 320 may require a return pad in intimate contact with the patient at a location remote from the operative site and/or other suitable return path. The return pad may be connected via a cable to the generator 320. In other embodiments, the operator 20 may provide sub-therapeutic RF energy levels for purposes of evaluating tissue conditions and providing feedback in the electrosurgical system 300. Such feedback may be employed to control the therapeutic RF energy output of the electrosurgical instrument 310.

During operation of electrosurgical instrument 300, the user generally grasps tissue, supplies energy to the captured tissue to form a weld or a seal (e.g., by actuating button 328 and/or pedal 216), and then drives a tissue-cutting element 371 at the distal end of the axially moveable member 378 through the captured tissue. According to various embodiments, the translation of the axial movement of the axially moveable member 378 may be paced, or otherwise controlled, to aid in driving the axially moveable member 378 at a suitable rate of travel. By controlling the rate of the travel, the likelihood that the captured tissue has been properly and functionally sealed prior to transection with the cutting element 371 is increased.

Figure 17:
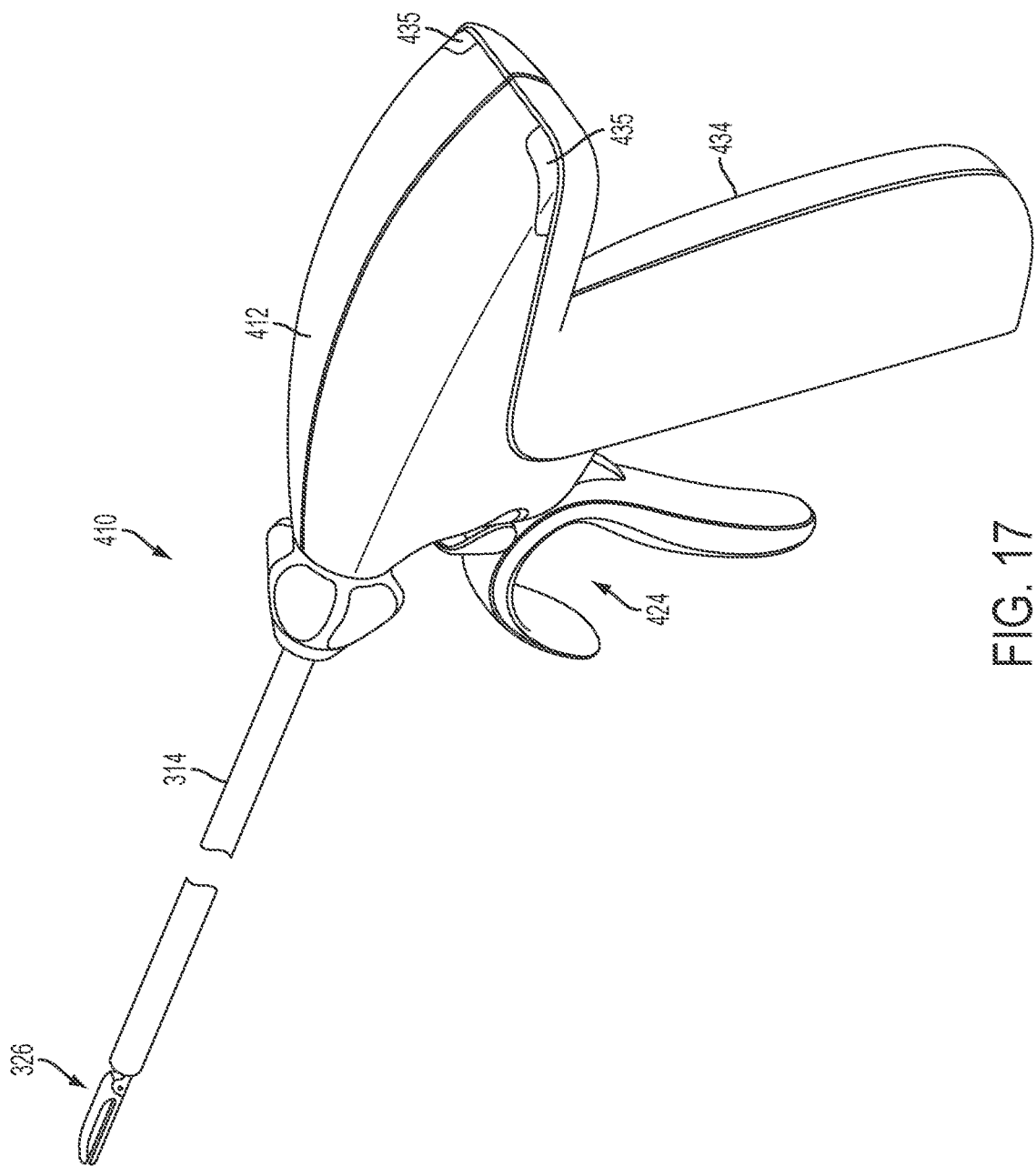
FIG. 17 illustrates a section a perspective view of one embodiment of a cordless electrical energy surgical instrument.

FIG. 17 is a perspective view of one example embodiment of a surgical instrument system comprising a cordless electrical energy surgical instrument 410. The electrosurgical system is similar to the electrosurgical system 300. The electrosurgical system can be configured to supply energy, such as electrical energy, ultrasonic energy, heat energy, or any combination thereof, to the tissue of a patient either independently or simultaneously as described in connection with FIGS. 1 and 11, for example. The electrosurgical instrument may utilize the end effector 326 and elongated shaft 314 described herein in conjunction with a cordless proximal handle 412. In one example embodiment, the handle 412 includes a generator circuit 420 (see FIG. 18). The generator circuit 420 performs a function substantially similar to that of generator 320. In one example embodiment, the generator circuit 420 is coupled to a controller, such as a control circuit. In the illustrated embodiment, the control circuit is integrated into the generator circuit 420. In other embodiments, the control circuit may be separate from the generator circuit 420.

In one example embodiment, various electrodes in the end effector 326 (including jaws 364A, 364B thereof) may be coupled to the generator circuit 420. The control circuit may be used to activate the generator 420, which may serve as an electrical source. In various embodiments, the generator 420 may comprise an RF source, an ultrasonic source, a direct current source, and/or any other suitable type of electrical energy source, for example. In one example embodiment, a button 328 may be provided to activate the generator circuit 420 to provide energy to the end effectors 326, 326.

FIG. 18A is a side view of one example embodiment of the handle 412 of the cordless surgical instrument 410. In FIG. 18, the handle 412 is shown with half of a first handle body removed to illustrate various components within second handle body 434. The handle 412 may comprise a lever arm 424 (e.g., a trigger) which may be pulled along a path 33 around a pivot point. The lever arm 424 may be coupled to an axially moveable member 478 disposed within elongated shaft 314 by a shuttle operably engaged to an extension of lever arm 424. In one example embodiment, the lever arm 424 defines a shepherd's hook shape comprising a distal member 424a and a proximal member 424b.

In one example embodiment, the cordless electrosurgical instrument comprises a battery 437. The battery 437 provides electrical energy to the generator circuit 420. The battery 437 may be any battery suitable for driving the generator circuit 420 at the desired energy levels. In one example embodiment, the battery 437 is a 100 mAh, triple-cell Lithium Ion Polymer battery. The battery may be fully charged prior to use in a surgical procedure, and may hold a voltage of about 12.6V. The battery 437 may have two fuses fitted to the cordless electrosurgical instrument 410, arranged in line with each battery terminal. In one example embodiment, a charging port 439 is provided to connect the battery 437 to a DC current source (not shown).

Figure 18B:
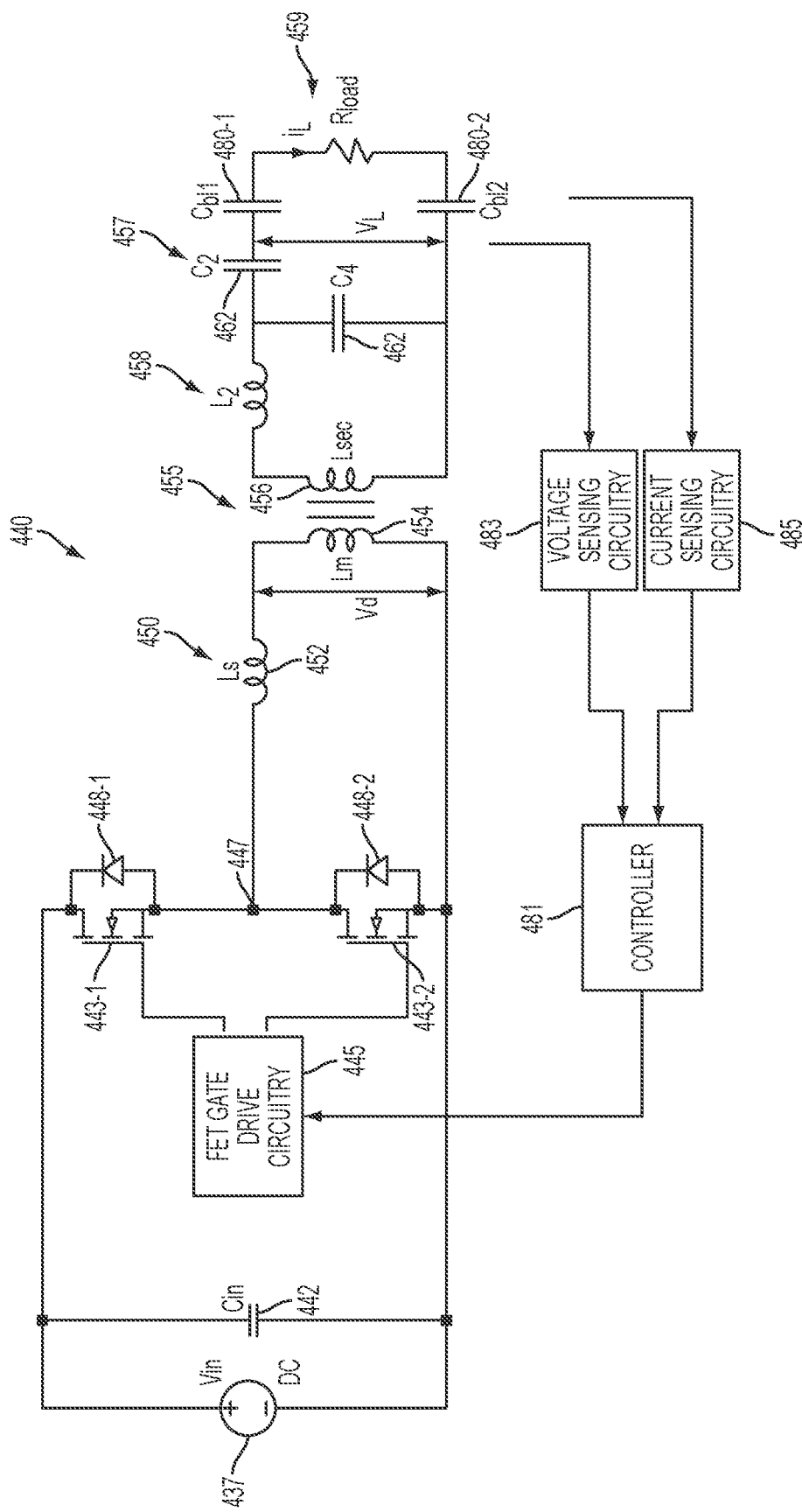
FIG. 18B illustrates an RF drive and control circuit, according to one embodiment.

The generator circuit 420 may be configured in any suitable manner. In some embodiments, the generator circuit comprises an RF drive and control circuit 440. FIG. 18B illustrates an RF drive and control circuit 440, according to one embodiment. FIG. 18B is a part schematic part block diagram illustrating the RF drive and control circuitry 440 used in this embodiment to generate and control the RF electrical energy supplied to the end effector 326. As will be explained in more detail below, in this embodiment, the drive circuitry 440 is a resonant mode RF amplifier comprising a parallel resonant network on the RF amplifier output and the control circuitry operates to control the operating frequency of the drive signal so that it is maintained at the resonant frequency of the drive circuit, which in turn controls the amount of power supplied to the end effector 326. The way that this is achieved will become apparent from the following description.

As shown in FIG. 18B, the RF drive and control circuit 440 comprises the above described battery 437 are arranged to supply, in this example, about 0V and about 12V rails. An input capacitor ($C_{in}$) 442 is connected between the 0V and the 12V for providing a low source impedance. A pair of FET switches 443-1 and 443-2 (both of which are N-channel in this embodiment to reduce power losses) is connected in series between the 0V rail and the 12V rail. FET gate drive circuitry 445 is provided that generates two drive signals— one for driving each of the two FETs 443. The FET gate drive circuitry 445 generates drive signals that causes the upper FET (443-1) to be on when the lower FET (443-2) is off and vice versa. This causes the node 447 to be alternately connected to the 12V rail (when the FET 443-1 is switched on) and the 0V rail (when the FET 443-2 is switched on). FIG. 18B also shows the internal parasitic diodes 448-1 and 448-2 of the corresponding FETs 443, which conduct during any periods that the FETs 443 are open.

As shown in FIG. 18B, the node 447 is connected to an inductor-inductor resonant circuit 450 formed by inductor $L_s$ 452 and inductor $L_m$ 454. The FET gate driving circuitry 445 is arranged to generate drive signals at a drive frequency ($f_d$) that opens and crosses the FET switches 443 at the resonant frequency of the parallel resonant circuit 450. As a result of the resonant characteristic of the resonant circuit 450, the square wave voltage at node 447 will cause a substantially sinusoidal current at the drive frequency ($f_d$) to flow within the resonant circuit 450. As illustrated in FIG. 18B, the inductor $L_m$ 454 is the primary of a transformer 455, the secondary of which is formed by inductor $L_{sec}$ 456. The inductor $L_{sec}$ 456 of the transformer 455 secondary is connected to an inductor-capacitor-capacitor parallel resonant circuit 457 formed by inductor $L_2$ 458, capacitor $C_4$ 460, and capacitor $C_2$ 462. The transformer 455 up-converts the drive voltage ($V_d$) across the inductor $L_m$ 454 to the voltage that is applied to the output parallel resonant circuit 457. The load voltage ($V_L$) is output by the parallel resonant circuit 457 and is applied to the load (represented by the load resistance $R_{load}$ 459 in FIG. 18B) corresponding to the impedance of the forceps' jaws and any tissue or vessel gripped by the end effector 326. As shown in FIG. 18B, a pair of DC blocking capacitors $C_{b1}$ 480-1 and 480-2 is provided to prevent any DC signal being applied to the load 459.

In one embodiment, the transformer 455 may be implemented with a Core Diameter (mm), Wire Diameter (mm), and Gap between secondary windings in accordance with the following specifications:

Core Diameter, D (mm)

$$D=19.9\times10-3$$

Wire diameter, W (mm) for 22 AWG wire $$W=7.366\times10-4$$

Gap between secondary windings, in gap=0.125

$$G=gap/25.4$$

In this embodiment, the amount of electrical power supplied to the end effector 326 is controlled by varying the frequency of the switching signals used to switch the FETs 443. This works because the resonant circuit 450 acts as a frequency dependent (loss less) attenuator. The closer the drive signal is to the resonant frequency of the resonant circuit 450, the less the drive signal is attenuated. Similarly, as the frequency of the drive signal is moved away from the resonant frequency of the circuit 450, the more the drive signal is attenuated and so the power supplied to the load reduces. In this embodiment, the frequency of the switching signals generated by the FET gate drive circuitry 445 is controlled by a controller 481 based on a desired power to be delivered to the load 459 and measurements of the load voltage ($V_L$) and of the load current ($I_L$) obtained by conventional voltage sensing circuitry 483 and current sensing circuitry 485. The way that the controller 481 operates will be described in more detail below.

In one embodiment, the voltage sensing circuitry 483 and the current sensing circuitry 485 may be implemented with high bandwidth, high speed rail-to-rail amplifiers (e.g., LMH6643 by National Semiconductor). Such amplifiers, however, consume a relatively high current when they are operational. Accordingly, a power save circuit may be provided to reduce the supply voltage of the amplifiers when they are not being used in the voltage sensing circuitry 483 and the current sensing circuitry 485. In one-embodiment, a step-down regulator (e.g., LT3502 by Linear Technologies) may be employed by the power save circuit to reduce the supply voltage of the rail-to-rail amplifiers and thus extend the life of the battery 437.

Figure 18C:
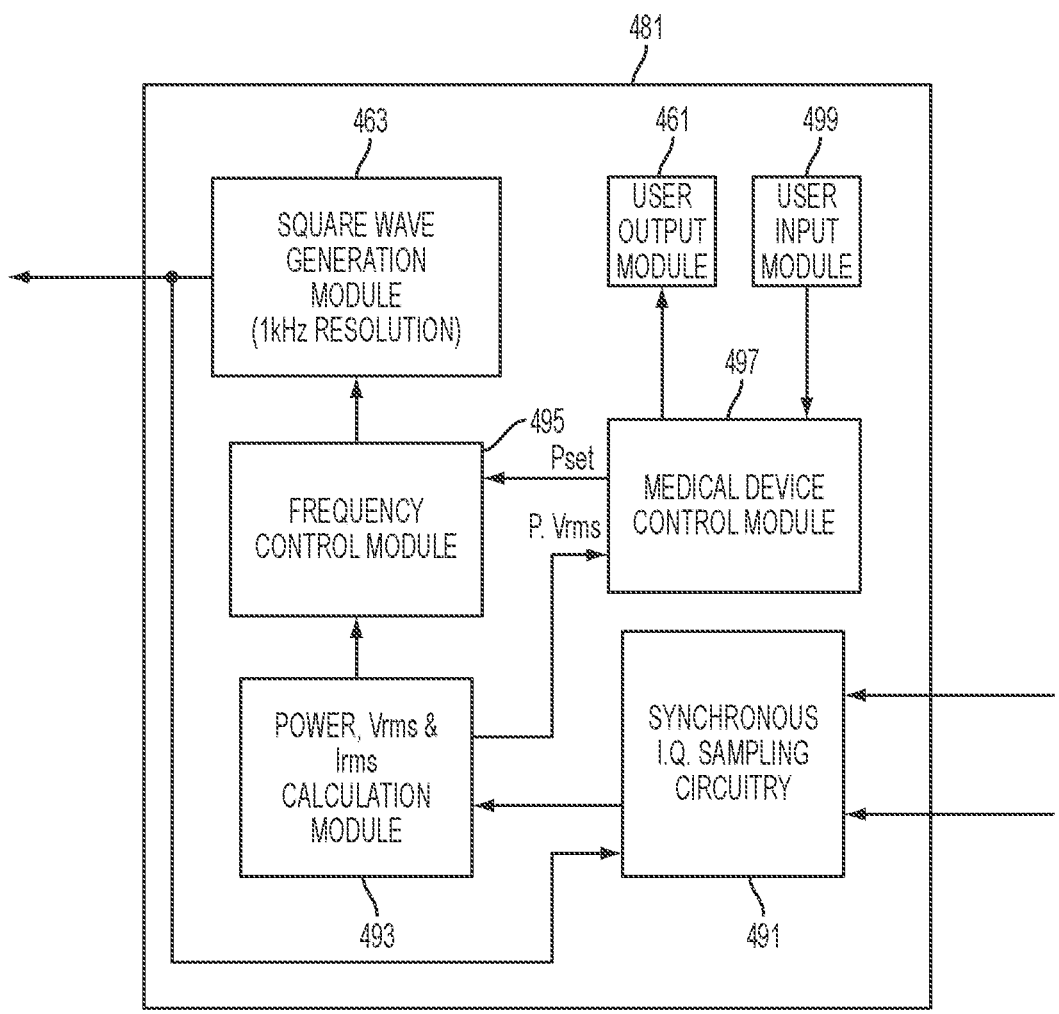
FIG. 18C illustrates the main components of the controller, according to one embodiment.

FIG. 18C illustrates the main components of the controller 481, according to one embodiment. In the embodiment illustrated in FIG. 18C, the controller 481 is a microprocessor based controller and so most of the components illustrated in FIG. 16 are software based components. Nevertheless, a hardware based controller 481 may be used instead. As shown, the controller 481 includes synchronous I,Q sampling circuitry 491 that receives the sensed voltage and current signals from the sensing circuitry 483 and 485 and obtains corresponding samples which are passed to a power, $V_{rms}$ and $I_{rms}$ calculation module 493. The calculation module 493 uses the received samples to calculate the RMS voltage and RMS current applied to the load 459 (FIG. 18B; end effector 326 and tissue/vessel gripped thereby) and from them the power that is presently being supplied to the load 459. The determined values are then passed to a frequency control module 495 and a medical device control module 497. The medical device control module 497 uses the values to determine the present impedance of the load 459 and based on this determined impedance and a pre-defined algorithm, determines what set point power ($P_{set}$) should be applied to the frequency control module 495. The medical device control module 497 is in turn controlled by signals received from a user input module 499 that receives inputs from the user (for example pressing buttons or activating the control levers 114, 110 on the handle 104) and also controls output devices (lights, a display, speaker or the like) on the handle 104 via a user output module 461.

The frequency control module 495 uses the values obtained from the calculation module 493 and the power set point ($P_{set}$) obtained from the medical device control module 497 and predefined system limits (to be explained below), to determine whether or not to increase or decrease the applied frequency. The result of this decision is then passed to a square wave generation module 463 which, in this embodiment, increments or decrements the frequency of a square wave signal that it generates by 1 kHz, depending on the received decision. As those skilled in the art will appreciate, in an alternative embodiment, the frequency control module 495 may determine not only whether to increase or decrease the frequency, but also the amount of frequency change required. In this case, the square wave generation module 463 would generate the corresponding square wave signal with the desired frequency shift. In this embodiment, the square wave signal generated by the square wave generation module 463 is output to the FET gate drive circuitry 445, which amplifies the signal and then applies it to the FET 443-1. The FET gate drive circuitry 445 also inverts the signal applied to the FET 443-1 and applies the inverted signal to the FET 443-2.

The electrosurgical instrument 410 may comprise additional features as discussed with respect to electrosurgical system 300. Those skilled in the art will recognize that electrosurgical instrument 410 may include a rotation knob 348, an elongated shaft 314, and an end effector 326. These elements function in a substantially similar manner to that discussed above with respect to the electrosurgical system 300. In one example embodiment, the cordless electrosurgical instrument 410 may include visual indicators 435. The visual indicators 435 may provide a visual indication signal to an operator. In one example embodiment, the visual indication signal may alert an operator that the device is on, or that the device is applying energy to the end effector. Those skilled in the art will recognize that the visual indicators 435 may be configured to provide information on multiple states of the device.

Over the years a variety of minimally invasive robotic (or "telesurgical") systems have been developed to increase surgical dexterity as well as to permit a surgeon to operate on a patient in an intuitive manner. Robotic surgical systems can be used with many different types of surgical instruments including, for example, ultrasonic or electrosurgical instruments, as described herein. Example robotic systems include those manufactured by Intuitive Surgical, Inc., of Sunnyvale, California, U.S.A. Such systems, as well as robotic systems from other manufacturers, are disclosed in the following U.S. patents which are each herein incorporated by reference in their respective entirety: U.S. Pat. No. 5,792,135, entitled "Articulated Surgical Instrument For Performing Minimally Invasive Surgery With Enhanced Dexterity and Sensitivity", U.S. Pat. No. 6,231,565, entitled "Robotic Arm DLUs For Performing Surgical Tasks", U.S. Pat. No. 6,783,524, entitled "Robotic Surgical Tool With Ultrasound Cauterizing and Cutting Instrument", U.S. Pat. No. 6,364,888, entitled "Alignment of Master and Slave In a Minimally Invasive Surgical Apparatus", U.S. Pat. No. 7,524,320, entitled "Mechanical Actuator Interface System For Robotic Surgical Tools", U.S. Pat. No. 7,691,098, entitled Platform Link Wrist Mechanism", U.S. Pat. No. 7,806,891, entitled "Repositioning and Reorientation of Master/Slave Relationship in Minimally Invasive Telesurgery", and U.S. Pat. No. 7,824,401, entitled "Surgical Tool With Writed Monopolar Electrosurgical End Effectors". Many of such systems, however, have in the past been unable to generate the magnitude of forces required to effectively cut and fasten tissue.

FIGS. 19-46A illustrate example embodiments of robotic surgical systems. In some embodiments, the disclosed robotic surgical systems may utilize the ultrasonic or electrosurgical instruments described herein. Those skilled in the art will appreciate that the illustrated robotic surgical systems are not limited to only those instruments described herein, and may utilize any compatible surgical instruments. Those skilled in the art will further appreciate that while various embodiments described herein may be used with the described robotic surgical systems, the disclosure is not so limited, and may be used with any compatible robotic surgical system.

Figure 19:
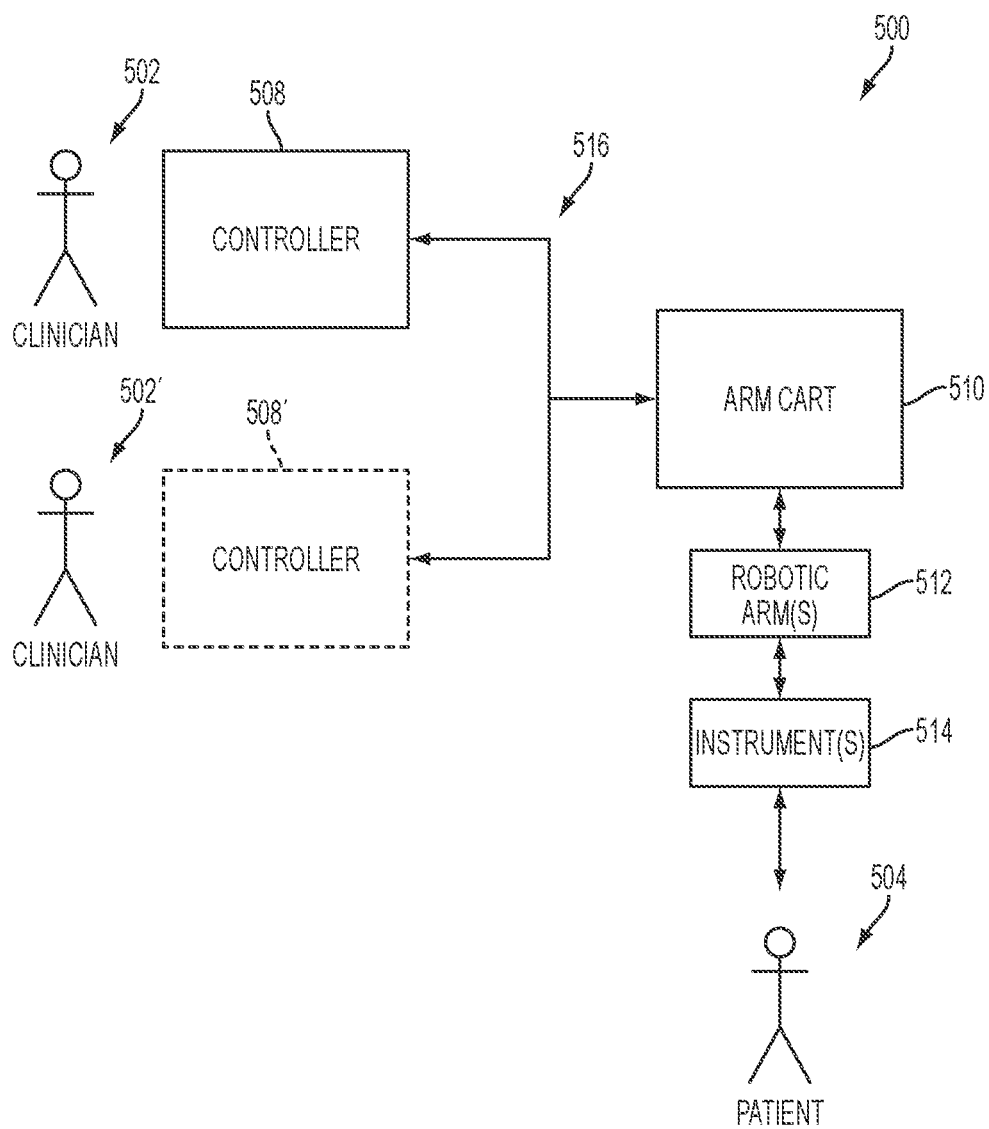
FIG. 19 illustrates a block diagram of one embodiment of a robotic surgical system.

FIGS. 19-25 illustrate the structure and operation of several example robotic surgical systems and components thereof. FIG. 19 shows a block diagram of an example robotic surgical system 500. The system 500 comprises at least one controller 508 and at least one arm cart 510. The arm cart 510 may be mechanically coupled to one or more robotic manipulators or arms, indicated by box 512. Each of the robotic arms 512 may comprise one or more surgical instruments 514 for performing various surgical tasks on a patient 504. Operation of the arm cart 510, including the arms 512 and instruments 514 may be directed by a clinician 502 from a controller 508. In some embodiments, a second controller 508', operated by a second clinician 502' may also direct operation of the arm cart 510 in conjunction with the first clinician 502'. For example, each of the clinicians 502, 502' may control different arms 512 of the cart or, in some cases, complete control of the arm cart 510 may be passed between the clinicians 502, 502'. In some embodiments, additional arm carts (not shown) may be utilized on the patient 504. These additional arm carts may be controlled by one or more of the controllers 508, 508'. The arm cart(s) 510 and controllers 508, 508' may be in communication with one another via a communications link 516, which may be any suitable type of wired or wireless communications link carrying any suitable type of signal (e.g., electrical, optical, infrared, etc.) according to any suitable communications protocol. Example implementations of robotic surgical systems, such as the system 500, are disclosed in U.S. Pat. No. 7,524,320 which has been herein incorporated by reference. Thus, various details of such devices will not be described in detail herein beyond that which may be necessary to understand various embodiments of the claimed device.

Figure 20:
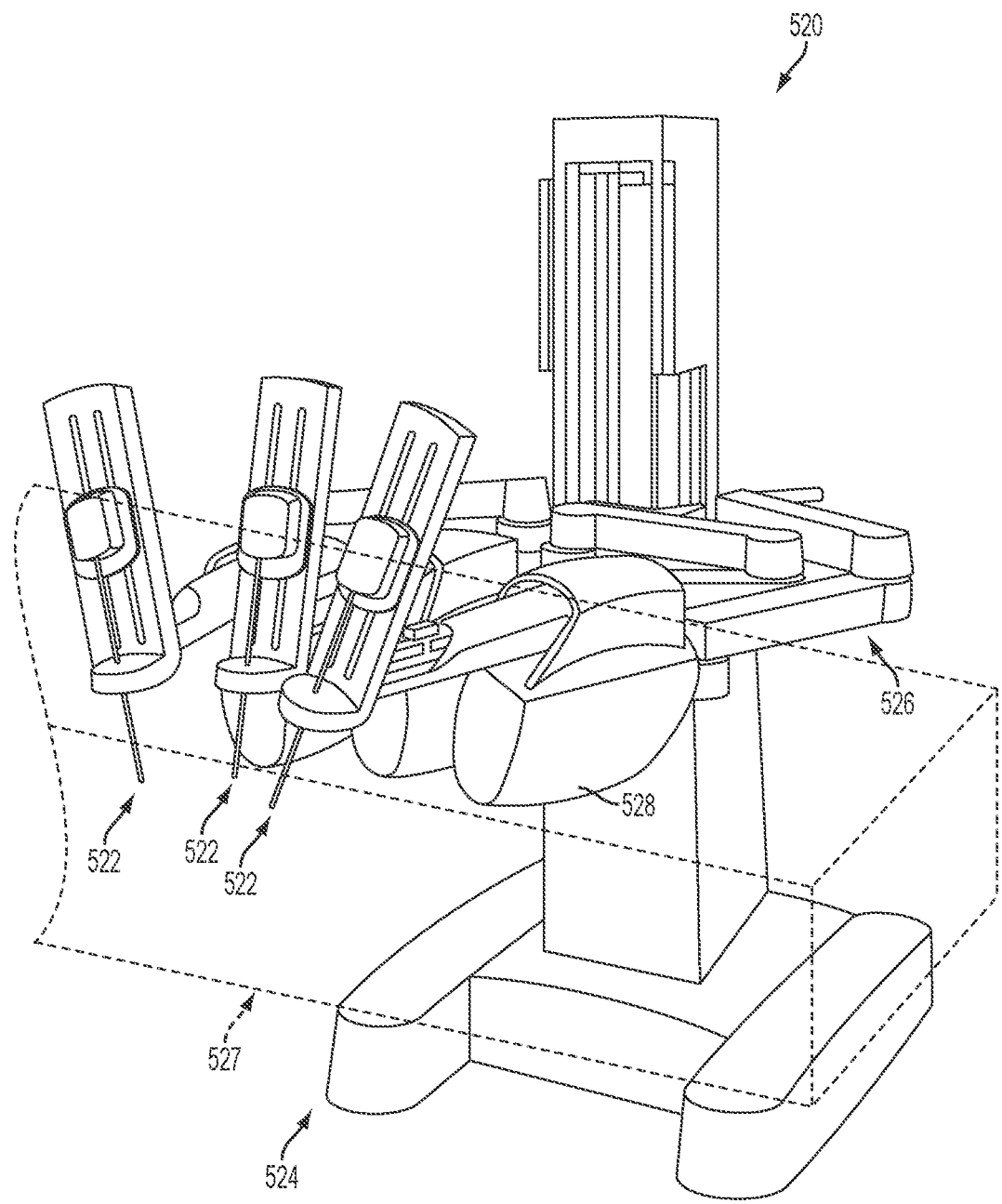
FIG. 20 illustrates one embodiment of a robotic arm cart.

FIG. 20 shows one example embodiment of a robotic arm cart 520. The robotic arm cart 520 is configured to actuate a plurality of surgical instruments or instruments, generally designated as 522 within a work envelope 527. Various robotic surgery systems and methods employing master controller and robotic arm cart arrangements are disclosed in U.S. Pat. No. 6,132,368, entitled "Multi-Component Telepresence System and Method", the full disclosure of which is incorporated herein by reference. In various forms, the robotic arm cart 520 includes a base 524 from which, in the illustrated embodiment, three surgical instruments 522 are supported. In various forms, the surgical instruments 522 are each supported by a series of manually articulatable linkages, generally referred to as set-up joints 526, and a robotic manipulator 528. These structures are herein illustrated with protective covers extending over much of the robotic linkage. These protective covers may be optional, and may be limited in size or entirely eliminated in some embodiments to minimize the inertia that is encountered by the servo mechanisms used to manipulate such devices, to limit the volume of moving components so as to avoid collisions, and to limit the overall weight of the cart 520. Cart 520 will generally have dimensions suitable for transporting the cart 520 between operating rooms. The cart 520 may be configured to typically fit through standard operating room doors and onto standard hospital elevators. In various forms, the cart 520 would preferably have a weight and include a wheel (or other transportation) system that allows the cart 520 to be positioned adjacent an operating table by a single attendant.

Figure 21:
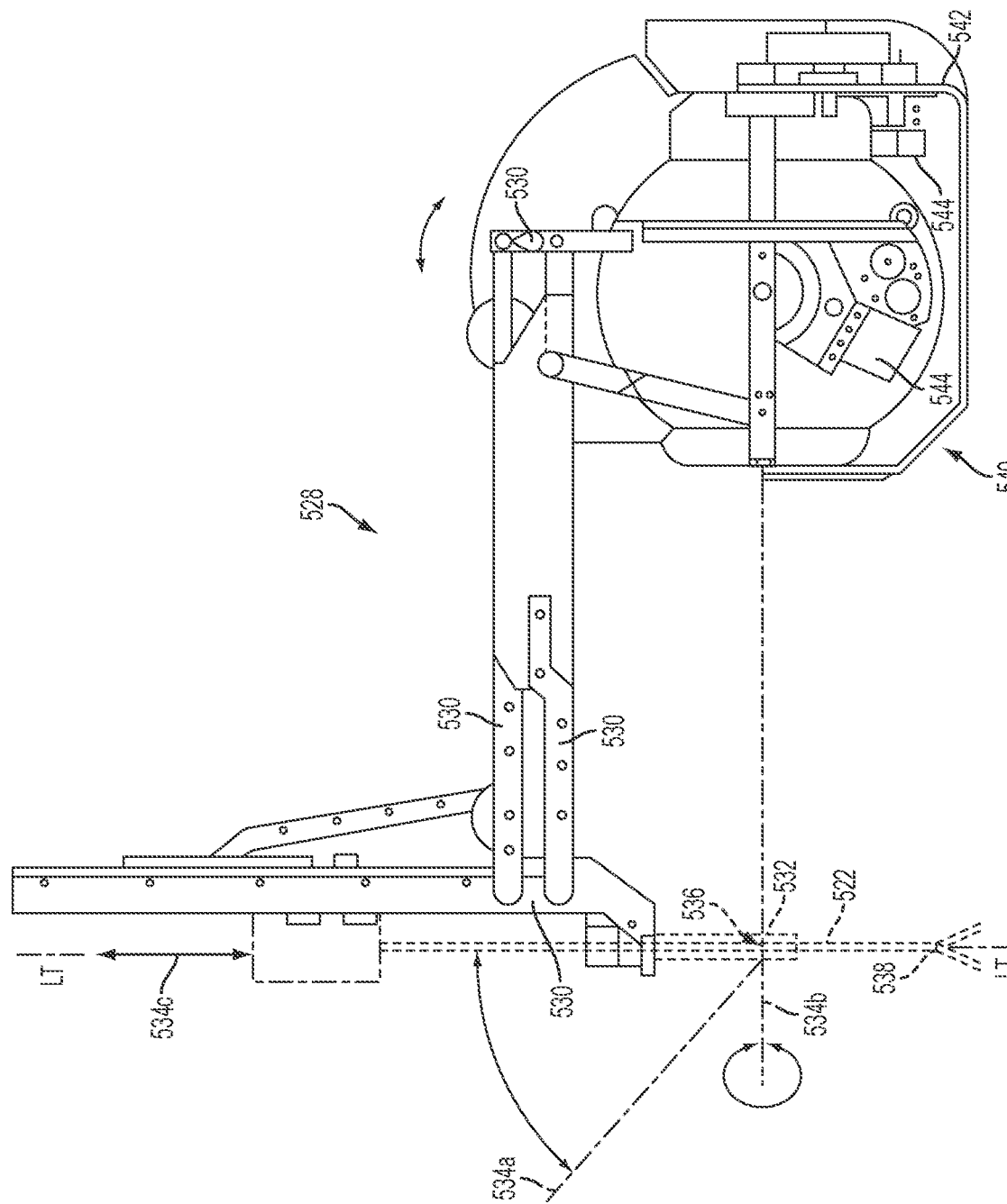
FIG. 21 illustrates one embodiment of the robotic manipulator of the robotic arm cart of FIG. 20.

FIG. 21 shows one example embodiment of the robotic manipulator 528 of the robotic arm cart 520. In the example shown in FIG. 21, the robotic manipulators 528 may include a linkage 530 that constrains movement of the surgical instrument 522. In various embodiments, linkage 530 includes rigid links coupled together by rotational joints in a parallelogram arrangement so that the surgical instrument 522 rotates around a point in space 532, as more fully described in issued U.S. Pat. No. 5,817,084, the full disclosure of which is herein incorporated by reference. The parallelogram arrangement constrains rotation to pivoting about an axis 534a, sometimes called the pitch axis. The links supporting the parallelogram linkage are pivotally mounted to set-up joints 526 (FIG. 20) so that the surgical instrument 522 further rotates about an axis 534b, sometimes called the yaw axis. The pitch and yaw axes 534a, 534b intersect at the remote center 536, which is aligned along a shaft 538 of the surgical instrument 522. The surgical instrument 522 may have further degrees of driven freedom as supported by manipulator 540, including sliding motion of the surgical instrument 522 along the longitudinal instrument axis "LT-LT". As the surgical instrument 522 slides along the instrument axis LT-LT relative to manipulator 540 (arrow 534c), remote center 536 remains fixed relative to base 542 of manipulator 540. Hence, the entire manipulator 540 is generally moved to re-position remote center 536. Linkage 530 of manipulator 540 is driven by a series of motors 544. These motors 544 actively move linkage 530 in response to commands from a processor of a control system. As will be discussed in further detail below, motors 544 are also employed to manipulate the surgical instrument 522.

Figure 22:
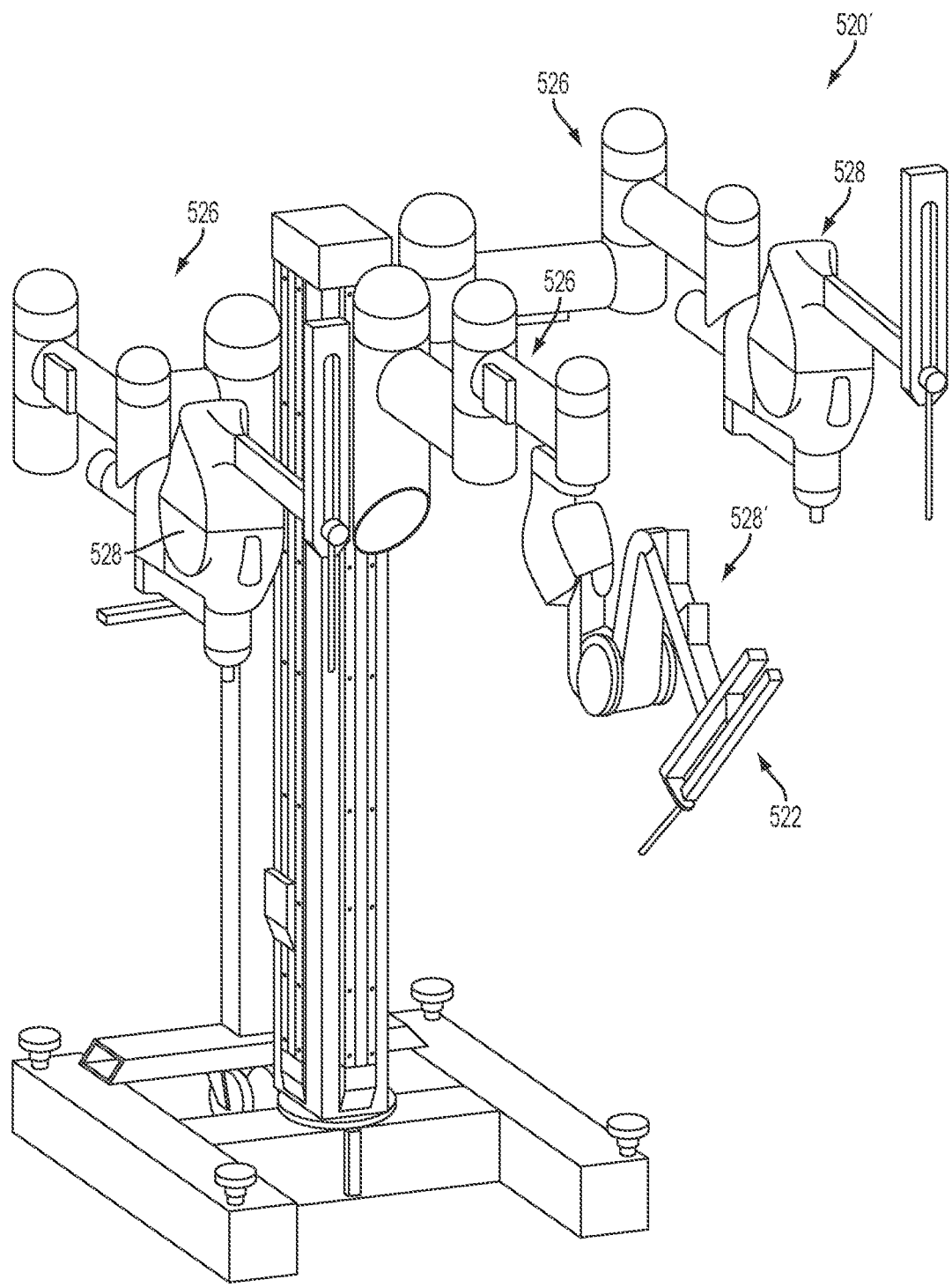
FIG. 22 illustrates one embodiment of a robotic arm cart having an alternative set-up joint structure.

FIG. 22 shows one example embodiment of a robotic arm cart 520' having an alternative set-up joint structure. In this example embodiment, a surgical instrument 522 is supported by an alternative manipulator structure 528' between two tissue manipulation instruments. Those of ordinary skill in the art will appreciate that various embodiments of the claimed device may incorporate a wide variety of alternative robotic structures, including those described in U.S. Pat. No. 5,878,193, the full disclosure of which is incorporated herein by reference. Additionally, while the data communication between a robotic component and the processor of the robotic surgical system is primarily described herein with reference to communication between the surgical instrument 522 and the controller, it should be understood that similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

Figure 23:
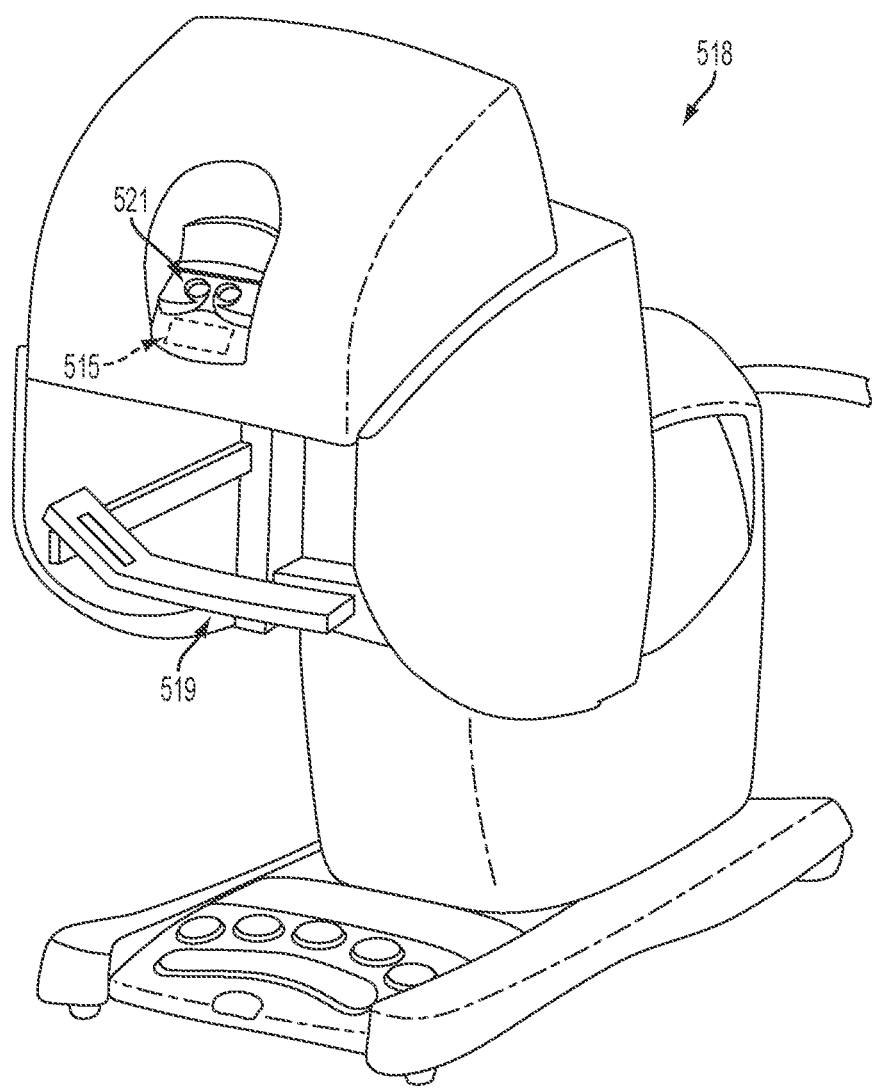
FIG. 23 illustrates one embodiment of a controller that may be used in conjunction with a robotic arm cart, such as the robotic arm carts of FIGS. 19-22.

FIG. 23 shows one example embodiment of a controller 518 that may be used in conjunction with a robotic arm cart, such as the robotic arm carts 520, 520' depicted in FIGS. 20-22. The controller 518 generally includes master controllers (generally represented as 519 in FIG. 23) which are grasped by the clinician and manipulated in space while the clinician views the procedure via a stereo display 521. A surgeon feed back meter 515 may be viewed via the display 521 and provide the surgeon with a visual indication of the amount of force being applied to the cutting instrument or dynamic clamping member. The master controllers 519 generally comprise manual input devices which preferably move with multiple degrees of freedom, and which often further have a handle or trigger for actuating instruments (for example, for closing grasping saws, applying an electrical potential to an electrode, or the like).

Figure 24:
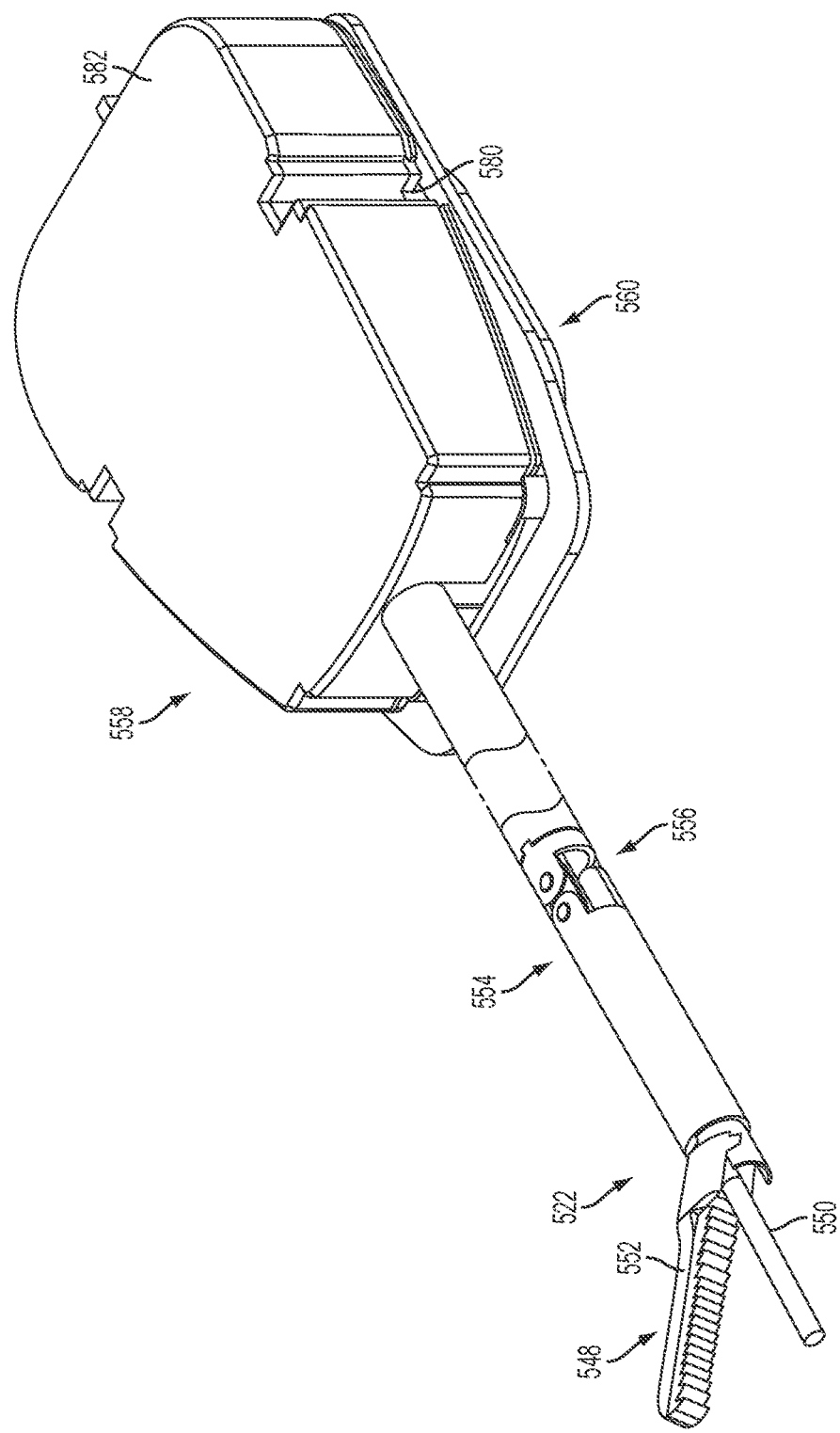
FIG. 24 illustrates one embodiment of an ultrasonic surgical instrument adapted for use with a robotic system.
Figure 25:
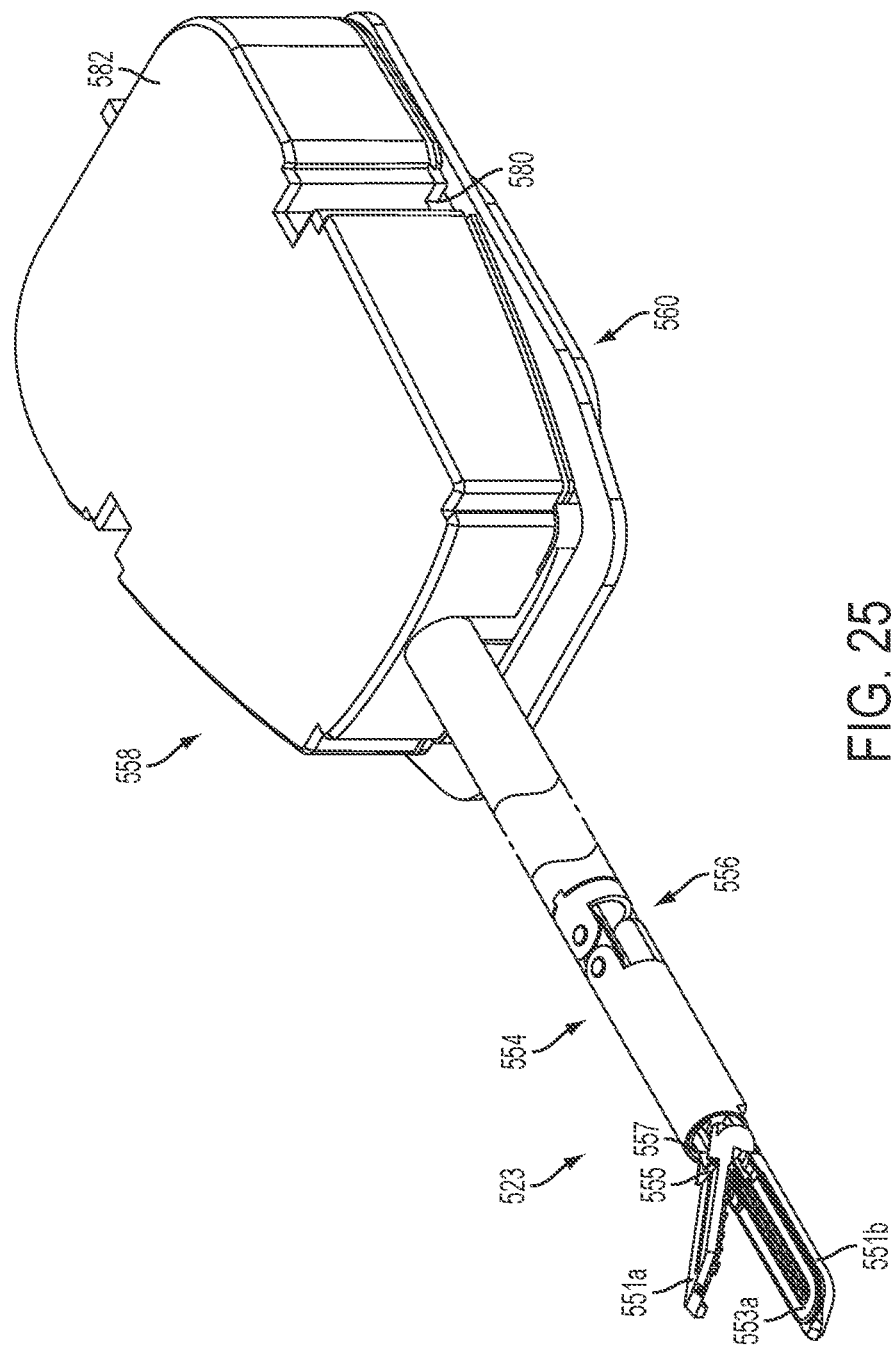
FIG. 25 illustrates one embodiment of an electrosurgical instrument adapted for use with a robotic system.
Figure 26:
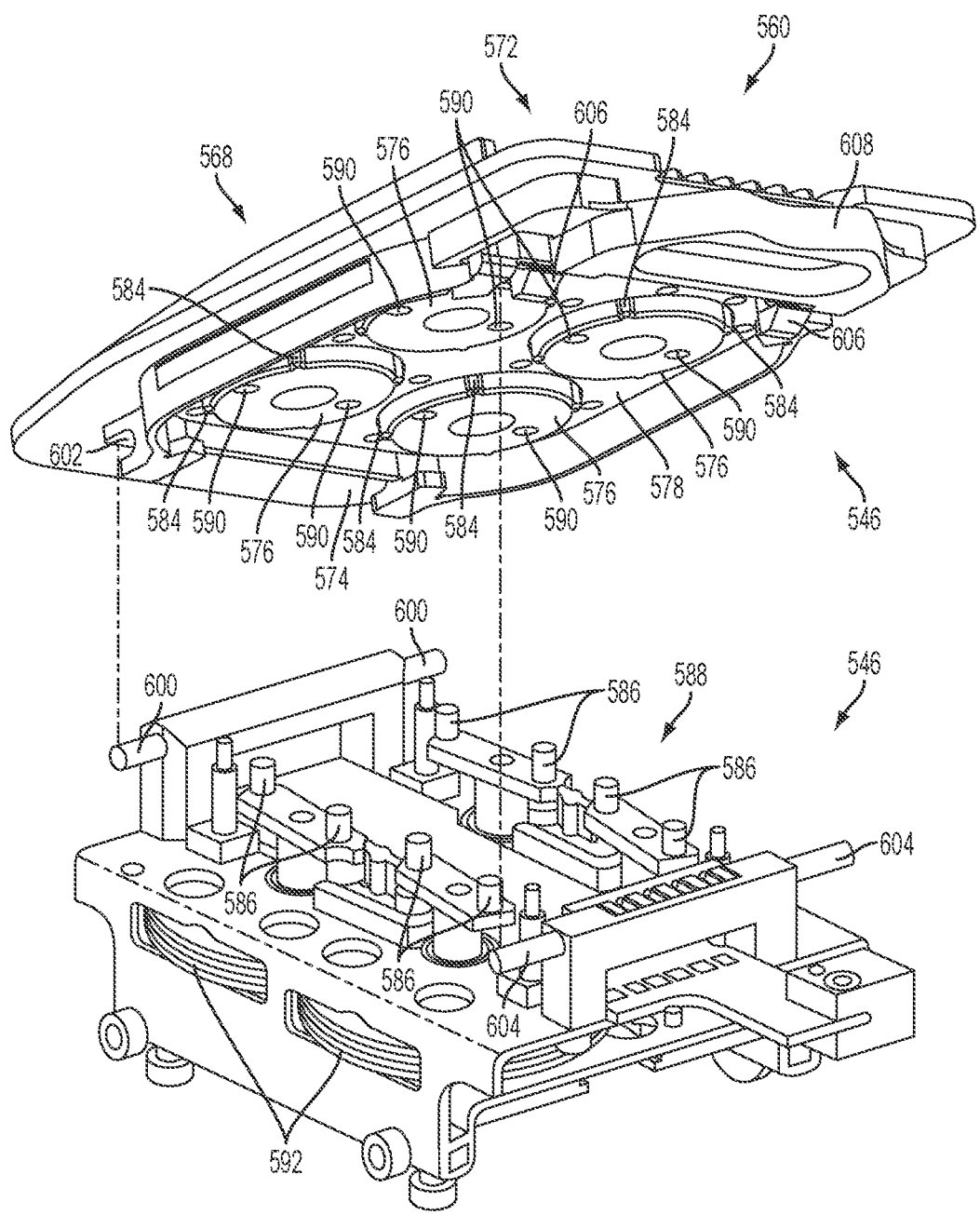
FIG. 26 illustrates one embodiment of an instrument drive assembly that may be coupled to a surgical manipulator to receive and control the surgical instrument shown in FIG. 24.

FIG. 24 shows one example embodiment of an ultrasonic surgical instrument 522 adapted for use with a robotic surgical system. For example, the surgical instrument 522 may be coupled to one of the surgical manipulators 528, 528' described hereinabove. As can be seen in FIG. 24, the surgical instrument 522 comprises a surgical end effector 548 that comprises an ultrasonic blade 550 and clamp arm 552, which may be coupled to an elongated shaft assembly 554 that, in some embodiments, may comprise an articulation joint 556. FIG. 25 shows another example embodiment having an electrosurgical instrument 523 in place of the ultrasonic surgical instrument 522. The surgical instrument 523 comprises a surgical end effector 548 that comprises closable jaws 551A, 551B having energy delivery surfaces 553A, 553B for engaging and providing electrical energy to tissue between the jaws 551A, 551B. A tissue cutting element or knife 555 may be positioned at the distal end of an axially movable member 557 that may extend through the elongated shaft assembly 554 to the instrument mounting portion 558. FIG. 26 shows one example embodiment of an instrument drive assembly 546 that may be coupled to one of the surgical manipulators 528, 528' to receive and control the surgical instruments 522, 523. The instrument drive assembly 546 may also be operatively coupled to the controller 518 to receive inputs from the clinician for controlling the instrument 522, 523. For example, actuation (e.g., opening and closing) of the clamp arm 552, actuation (e.g., opening and closing) of the jaws 551A, 551B, actuation of the ultrasonic blade 550, extension of the knife 555 and actuation of the energy delivery surfaces 553A, 553B, etc. may be controlled through the instrument drive assembly 546 based on inputs from the clinician provided through the controller 518. The surgical instrument 522 is operably coupled to the manipulator by an instrument mounting portion, generally designated as 558. The surgical instruments 522 further include an interface 560 which mechanically and electrically couples the instrument mounting portion 558 to the manipulator.

Figure 27:
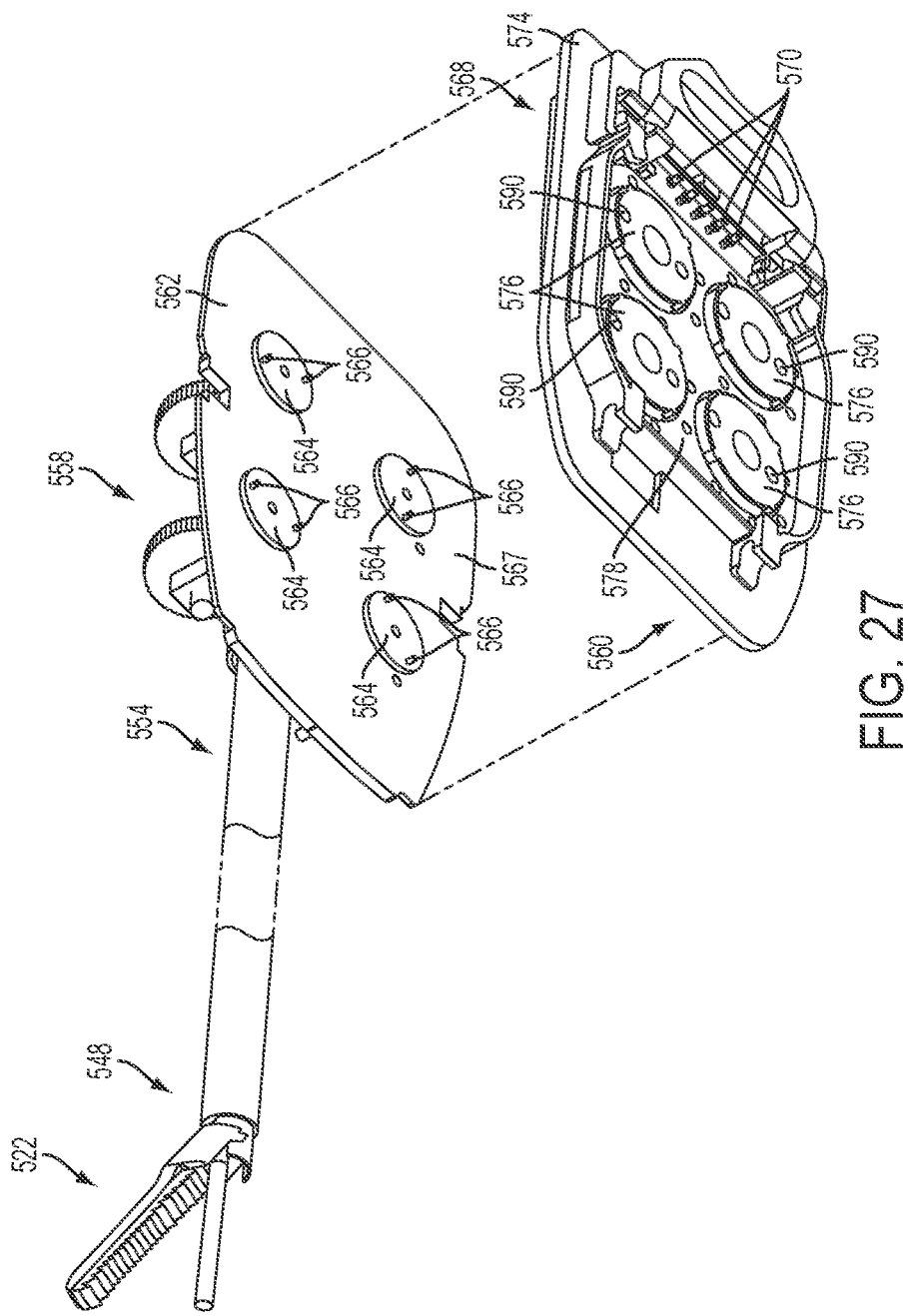
FIG. 27 illustrates another view of the instrument drive assembly embodiment of FIG. 26 including the surgical instrument of FIG. 24.
Figure 28:
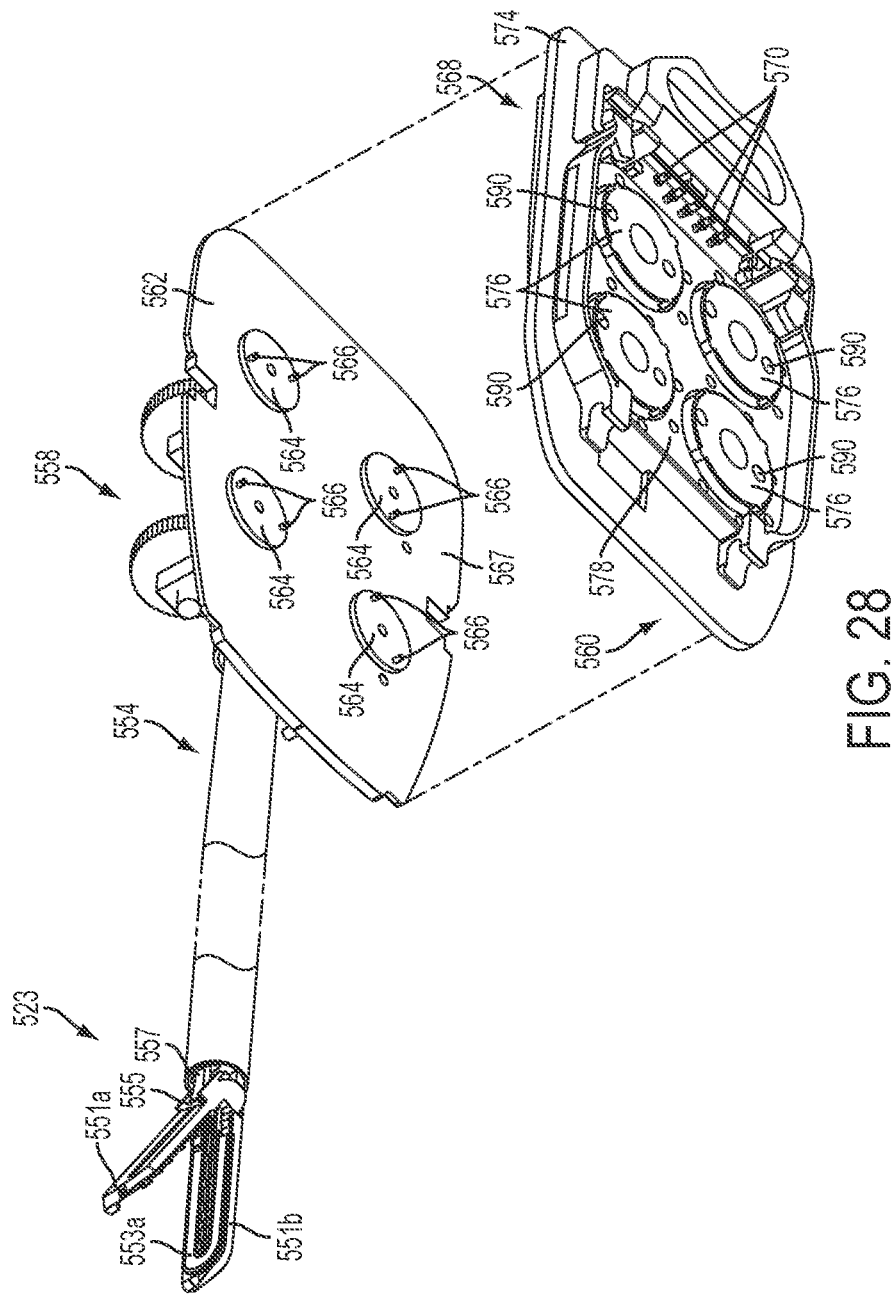
FIG. 28 illustrates another view of the instrument drive assembly of FIG. 26 including the electrosurgical instrument of FIG. 25.

FIG. 27 shows another view of the instrument drive assembly of FIG. 26 including the ultrasonic surgical instrument 522. FIG. 28 shows another view of the instrument drive assembly of FIG. 26 including the electrosurgical instrument 523. The instrument mounting portion 558 includes an instrument mounting plate 562 that operably supports a plurality of (four are shown in FIG. 26) rotatable body portions, driven discs or elements 564, that each include a pair of pins 566 that extend from a surface of the driven element 564. One pin 566 is closer to an axis of rotation of each driven elements 564 than the other pin 566 on the same driven element 564, which helps to ensure positive angular alignment of the driven element 564. The driven elements 564 and pints 566 may be positioned on an adapter side 567 of the instrument mounting plate 562.

Interface 560 also includes an adaptor portion 568 that is configured to mountingly engage the mounting plate 562 as will be further discussed below. The adaptor portion 568 may include an array of electrical connecting pins 570, which may be coupled to a memory structure by a circuit board within the instrument mounting portion 558. While interface 560 is described herein with reference to mechanical, electrical, and magnetic coupling elements, it should be understood that a wide variety of telemetry modalities might be used, including infrared, inductive coupling, or the like.

Figure 29:
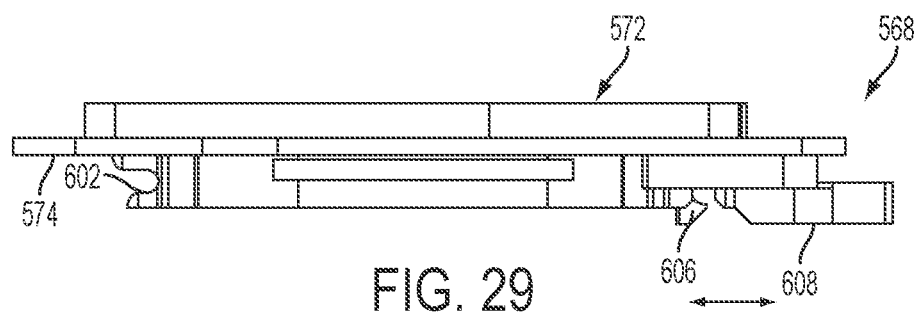
FIGS. 29-31 illustrate additional views of the adapter portion of the instrument drive assembly embodiment of FIG. 26.
Figure 30:
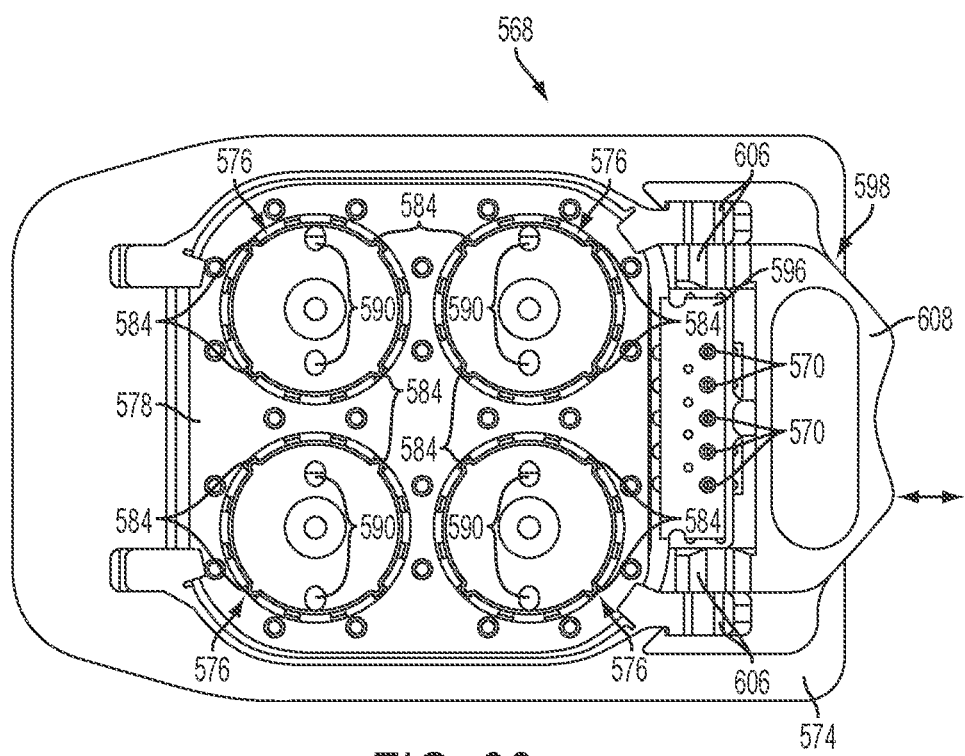
Figure 31:
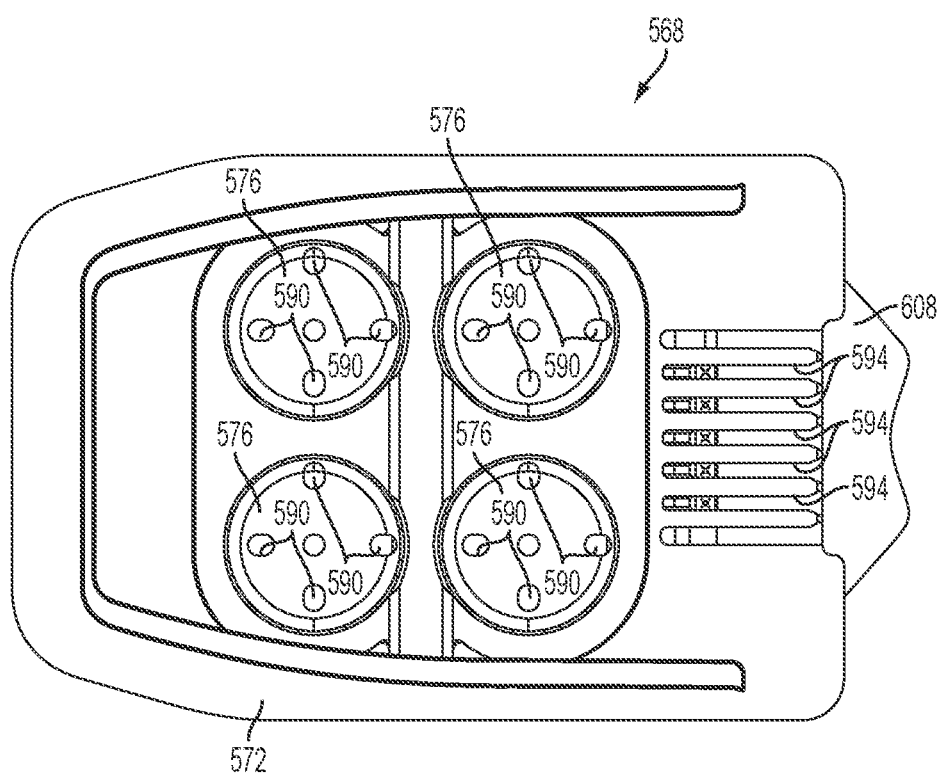

FIGS. 29-31 show additional views of the adapter portion 568 of the instrument drive assembly 546 of FIG. 26. The adapter portion 568 generally includes an instrument side 572 and a holder side 574 (FIG. 29). In various embodiments, a plurality of rotatable bodies 576 are mounted to a floating plate 578 which has a limited range of movement relative to the surrounding adaptor structure normal to the major surfaces of the adaptor 568. Axial movement of the floating plate 578 helps decouple the rotatable bodies 576 from the instrument mounting portion 558 when the levers 580 along the sides of the instrument mounting portion housing 582 are actuated (See FIGS. 24, 25) Other mechanisms/arrangements may be employed for releasably coupling the instrument mounting portion 558 to the adaptor 568. In at least one form, rotatable bodies 576 are resiliently mounted to floating plate 578 by resilient radial members which extend into a circumferential indentation about the rotatable bodies 576. The rotatable bodies 576 can move axially relative to plate 578 by deflection of these resilient structures. When disposed in a first axial position (toward instrument side 572) the rotatable bodies 576 are free to rotate without angular limitation. However, as the rotatable bodies 576 move axially toward instrument side 572, tabs 584 (extending radially from the rotatable bodies 576) laterally engage detents on the floating plates so as to limit angular rotation of the rotatable bodies 576 about their axes. This limited rotation can be used to help drivingly engage the rotatable bodies 576 with drive pins 586 of a corresponding instrument holder portion 588 of the robotic system, as the drive pins 586 will push the rotatable bodies 576 into the limited rotation position until the pins 586 are aligned with (and slide into) openings 590.

Openings 590 on the instrument side 572 and openings 590 on the holder side 574 of rotatable bodies 576 are configured to accurately align the driven elements 564 (FIGS. 27, 28) of the instrument mounting portion 558 with the drive elements 592 of the instrument holder 588. As described above regarding inner and outer pins 566 of driven elements 564, the openings 590 are at differing distances from the axis of rotation on their respective rotatable bodies 576 so as to ensure that the alignment is not 33 degrees from its intended position. Additionally, each of the openings 590 may be slightly radially elongated so as to fittingly receive the pins 566 in the circumferential orientation. This allows the pins 566 to slide radially within the openings 590 and accommodate some axial misalignment between the instrument 522, 523 and instrument holder 588, while minimizing any angular misalignment and backlash between the drive and driven elements. Openings 590 on the instrument side 572 may be offset by about 90 degrees from the openings 590 (shown in broken lines) on the holder side 574, as can be seen most clearly in FIG. 31.

Various embodiments may further include an array of electrical connector pins 570 located on holder side 574 of adaptor 568, and the instrument side 572 of the adaptor 568 may include slots 594 (FIG. 31) for receiving a pin array (not shown) from the instrument mounting portion 558. In addition to transmitting electrical signals between the surgical instrument 522, 523 and the instrument holder 588, at least some of these electrical connections may be coupled to an adaptor memory device 596 (FIG. 30) by a circuit board of the adaptor 568.

A detachable latch arrangement 598 may be employed to releasably affix the adaptor 568 to the instrument holder 588. As used herein, the term "instrument drive assembly" when used in the context of the robotic system, at least encompasses various embodiments of the adapter 568 and instrument holder 588 and which has been generally designated as 546 in FIG. 26. For example, as can be seen in FIG. 26, the instrument holder 588 may include a first latch pin arrangement 600 that is sized to be received in corresponding clevis slots 602 provided in the adaptor 568. In addition, the instrument holder 588 may further have second latch pins 604 that are sized to be retained in corresponding latch clevises 606 in the adaptor 568. See FIG. 30. In at least one form, a latch assembly 608 is movably supported on the adapter 568 and is biasable between a first latched position wherein the latch pins 600 are retained within their respective latch clevis 602 and an unlatched position wherein the second latch pins 604 may be into or removed from the latch clevises 606. A spring or springs (not shown) are employed to bias the latch assembly into the latched position. A lip on the instrument side 572 of adaptor 568 may slidably receive laterally extending tabs of instrument mounting housing 582.

As described the driven elements 564 may be aligned with the drive elements 592 of the instrument holder 588 such that rotational motion of the drive elements 592 causes corresponding rotational motion of the driven elements 564. The rotation of the drive elements 592 and driven elements 564 may be electronically controlled, for example, via the robotic arm 512, in response to instructions received from the clinician 502 via a controller 508. The instrument mounting portion 558 may translate rotation of the driven elements 564 into motion of the surgical instrument 522, 523.

Figure 32:
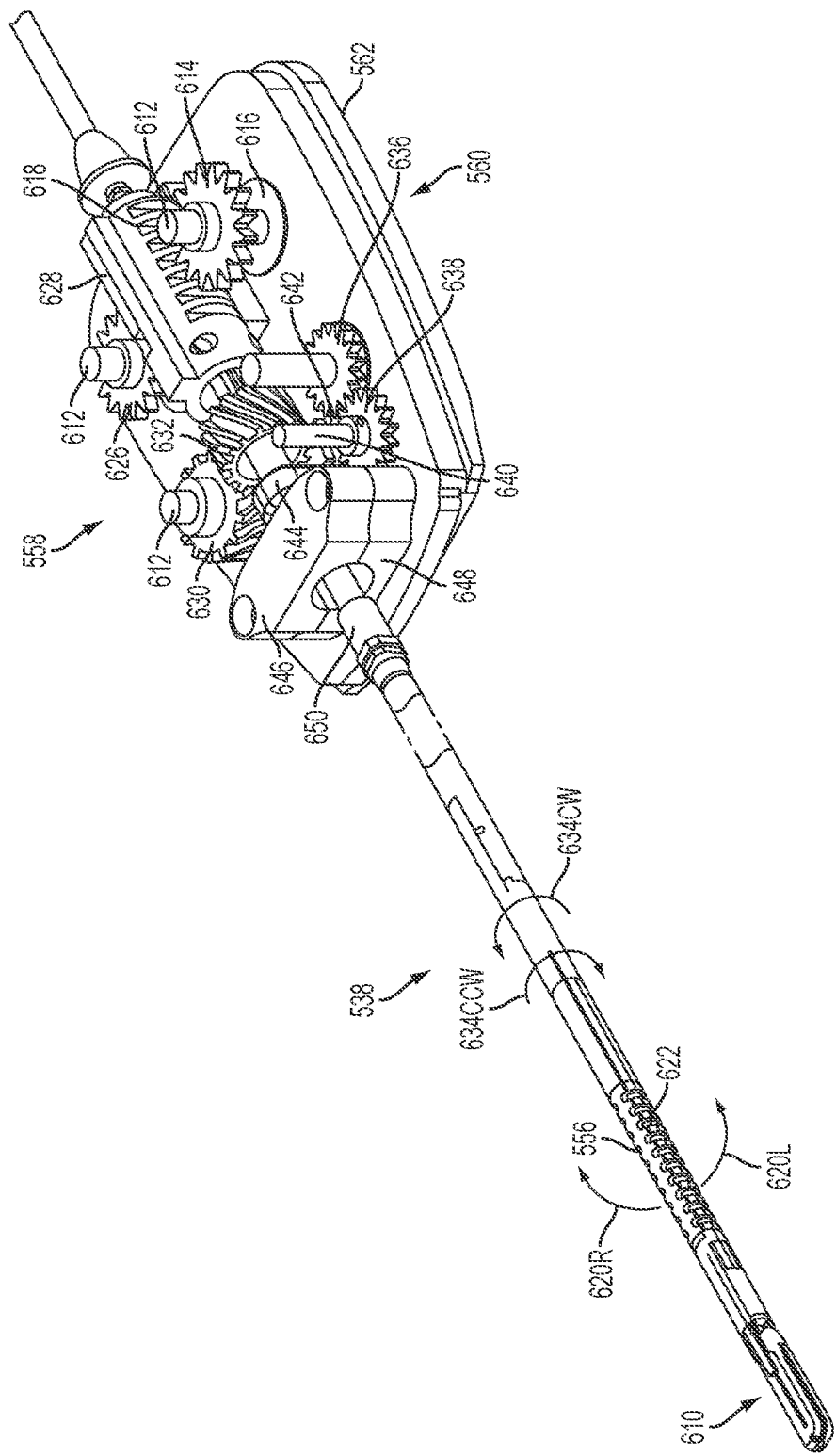
FIGS. 32-34 illustrate one embodiment of the instrument mounting portion of FIGS. 24-25 showing components for translating motion of the driven elements into motion of the surgical instrument.
Figure 33:
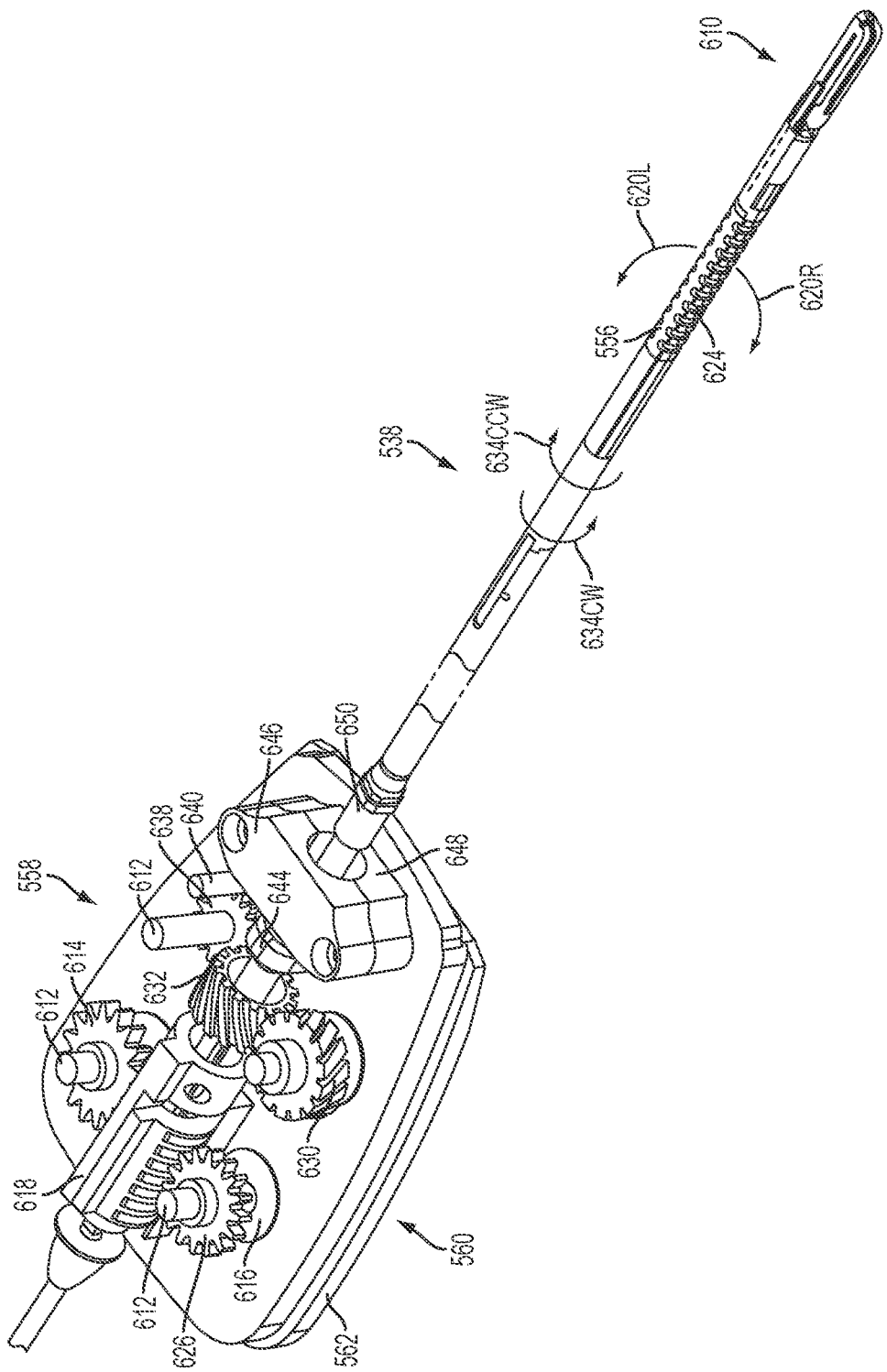
Figure 34:
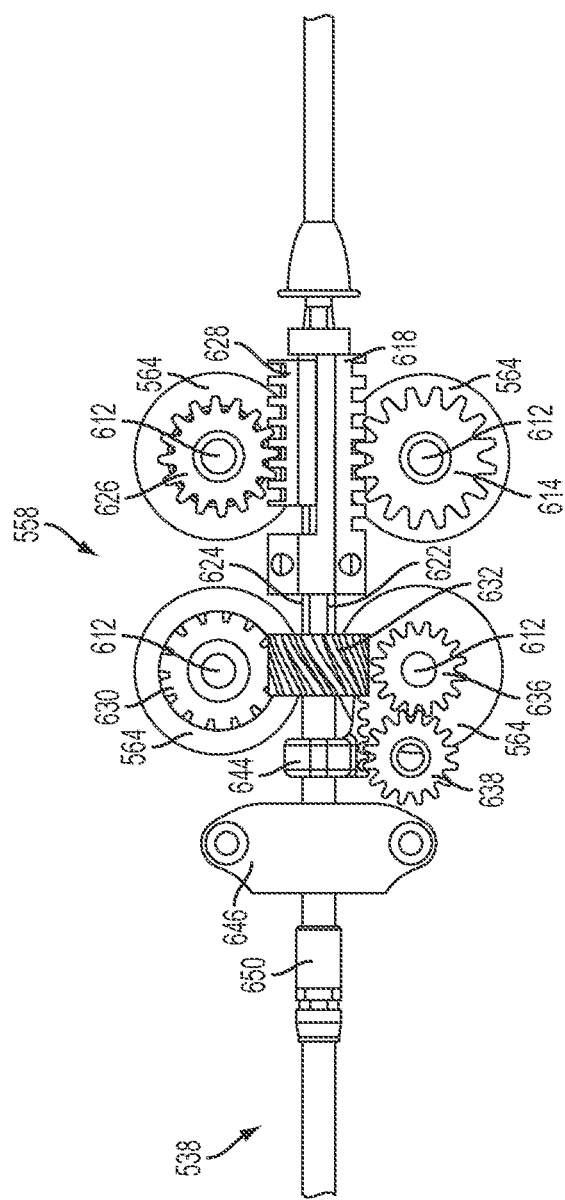

FIGS. 32-34 show one example embodiment of the instrument mounting portion 558 showing components for translating motion of the driven elements 564 into motion of the surgical instrument 522, 523. FIGS. 32-34 show the instrument mounting portion with a shaft 538 having a surgical end effector 610 at a distal end thereof. The end effector 610 may be any suitable type of end effector for performing a surgical task on a patient. For example, the end effector may be configured to provide RF and/or ultrasonic energy to tissue at a surgical site. The shaft 538 may be rotatably coupled to the instrument mounting portion 558 and secured by a top shaft holder 646 and a bottom shaft holder 648 at a coupler 650 of the shaft 538.

In one example embodiment, the instrument mounting portion 558 comprises a mechanism for translating rotation of the various driven elements 564 into rotation of the shaft 538, differential translation of members along the axis of the shaft (e.g., for articulation), and reciprocating translation of one or more members along the axis of the shaft 538 (e.g., for extending and retracting tissue cutting elements such as 555, overtubes and/or other components). In one example embodiment, the rotatable bodies 612 (e.g., rotatable spools) are coupled to the driven elements 564. The rotatable bodies 612 may be formed integrally with the driven elements 564. In some embodiments, the rotatable bodies 612 may be formed separately from the driven elements 564 provided that the rotatable bodies 612 and the driven elements 564 are fixedly coupled such that driving the driven elements 564 causes rotation of the rotatable bodies 612. Each of the rotatable bodies 612 is coupled to a gear train or gear mechanism to provide shaft articulation and rotation and clamp jaw open/close and knife actuation.

In one example embodiment, the instrument mounting portion 558 comprises a mechanism for causing differential translation of two or more members along the axis of the shaft 538. In the example provided in FIGS. 32-34, this motion is used to manipulate articulation joint 556. In the illustrated embodiment, for example, the instrument mounting portion 558 comprises a rack and pinion gearing mechanism to provide the differential translation and thus the shaft articulation functionality. In one example embodiment, the rack and pinion gearing mechanism comprises a first pinion gear 614 coupled to a rotatable body 612 such that rotation of the corresponding driven element 564 causes the first pinion gear 614 to rotate. A bearing 616 is coupled to the rotatable body 612 and is provided between the driven element 564 and the first pinion gear 614. The first pinion gear 614 is meshed to a first rack gear 618 to convert the rotational motion of the first pinion gear 614 into linear motion of the first rack gear 618 to control the articulation of the articulation section 556 of the shaft assembly 538 in a left direction 620L. The first rack gear 618 is attached to a first articulation band 622 (FIG. 32) such that linear motion of the first rack gear 618 in a distal direction causes the articulation section 556 of the shaft assembly 538 to articulate in the left direction 620L. A second pinion gear 626 is coupled to another rotatable body 612 such that rotation of the corresponding driven element 564 causes the second pinion gear 626 to rotate. A bearing 616 is coupled to the rotatable body 612 and is provided between the driven element 564 and the second pinion gear 626. The second pinion gear 626 is meshed to a second rack gear 628 to convert the rotational motion of the second pinion gear 626 into linear motion of the second rack gear 628 to control the articulation of the articulation section 556 in a right direction 620R. The second rack gear 628 is attached to a second articulation band 624 (FIG. 33) such that linear motion of the second rack gear 628 in a distal direction causes the articulation section 556 of the shaft assembly 538 to articulate in the right direction 620R. Additional bearings may be provided between the rotatable bodies and the corresponding gears. Any suitable bearings may be provided to support and stabilize the mounting and reduce rotary friction of shaft and gears, for example.

In one example embodiment, the instrument mounting portion 558 further comprises a mechanism for translating rotation of the driven elements 564 into rotational motion about the axis of the shaft 538. For example, the rotational motion may be rotation of the shaft 538 itself. In the illustrated embodiment, a first spiral worm gear 630 coupled to a rotatable body 612 and a second spiral worm gear 632 coupled to the shaft assembly 538. A bearing 616 (FIG. 17) is coupled to a rotatable body 612 and is provided between a driven element 564 and the first spiral worm gear 630. The first spiral worm gear 630 is meshed to the second spiral worm gear 632, which may be coupled to the shaft assembly 538 and/or to another component of the instrument 522, 523 for which longitudinal rotation is desired. Rotation may be caused in a clockwise (CW) and counter-clockwise (CCW) direction based on the rotational direction of the first and second spiral worm gears 630, 632. Accordingly, rotation of the first spiral worm gear 630 about a first axis is converted to rotation of the second spiral worm gear 632 about a second axis, which is orthogonal to the first axis. As shown in FIGS. 32-33, for example, a CW rotation of the second spiral worm gear 632 results in a CW rotation of the shaft assembly 538 in the direction indicated by 634CW. A CCW rotation of the second spiral worm gear 632 results in a CCW rotation of the shaft assembly 538 in the direction indicated by 634CCW. Additional bearings may be provided between the rotatable bodies and the corresponding gears. Any suitable bearings may be provided to support and stabilize the mounting and reduce rotary friction of shaft and gears, for example.

In one example embodiment, the instrument mounting portion 558 comprises a mechanism for generating reciprocating translation of one or more members along the axis of the shaft 538. Such translation may be used, for example to drive a tissue cutting element, such as 555, drive an overtube for closure and/or articulation of the end effector 610, etc. In the illustrated embodiment, for example, a rack and pinion gearing mechanism may provide the reciprocating translation. A first gear 636 is coupled to a rotatable body 612 such that rotation of the corresponding driven element 564 causes the first gear 636 to rotate in a first direction. A second gear 638 is free to rotate about a post 640 formed in the instrument mounting plate 562. The first gear 636 is meshed to the second gear 638 such that the second gear 638 rotates in a direction that is opposite of the first gear 636. In one example embodiment, the second gear 638 is a pinion gear meshed to a rack gear 642, which moves in a liner direction. The rack gear 642 is coupled to a translating block 644, which may translate distally and proximally with the rack gear 642. The translation block 644 may be coupled to any suitable component of the shaft assembly 538 and/or the end effector 610 so as to provide reciprocating longitudinal motion. For example, the translation block 644 may be mechanically coupled to the tissue cutting element 555 of the RF surgical device 523. In some embodiments, the translation block 644 may be coupled to an overtube, or other component of the end effector 610 or shaft 538.

Figure 35:
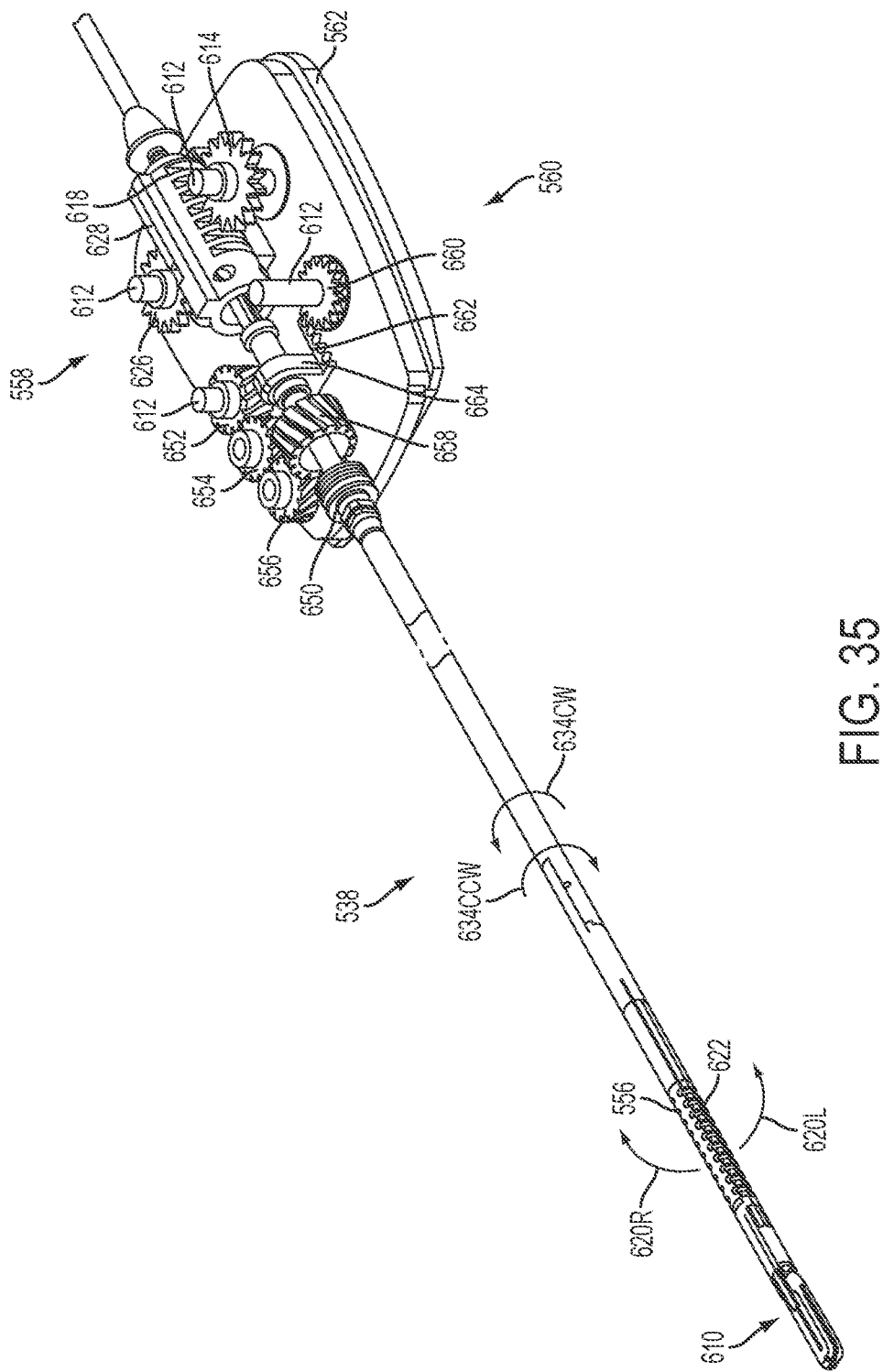
FIGS. 35-37 illustrate an alternate embodiment of the instrument mounting portion of FIGS. 24-25 showing an alternate example mechanism for translating rotation of the driven elements into rotational motion about the axis of the shaft and an alternate example mechanism for generating reciprocating translation of one or more members along the axis of the shaft 538.
Figure 36:
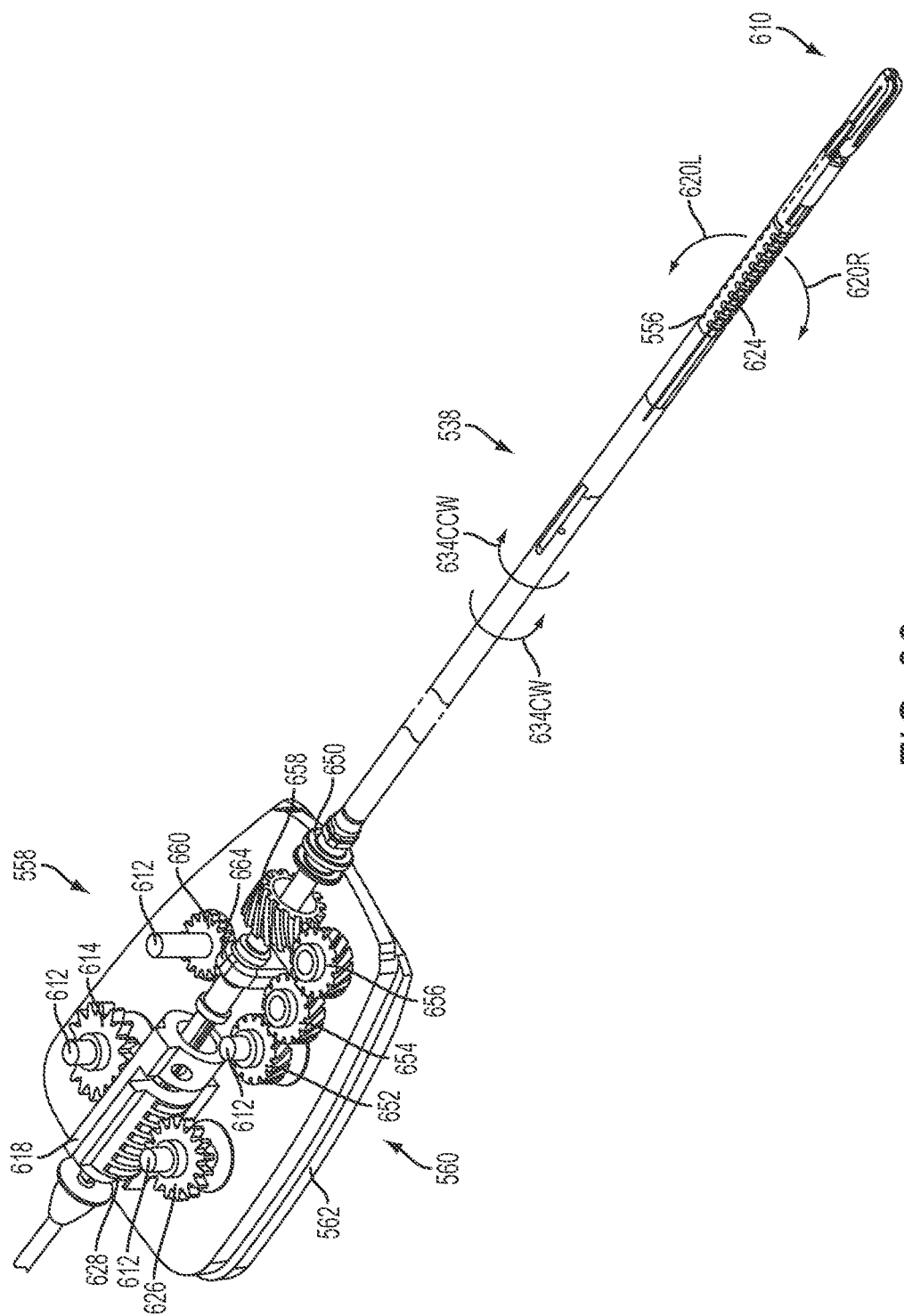
Figure 37:
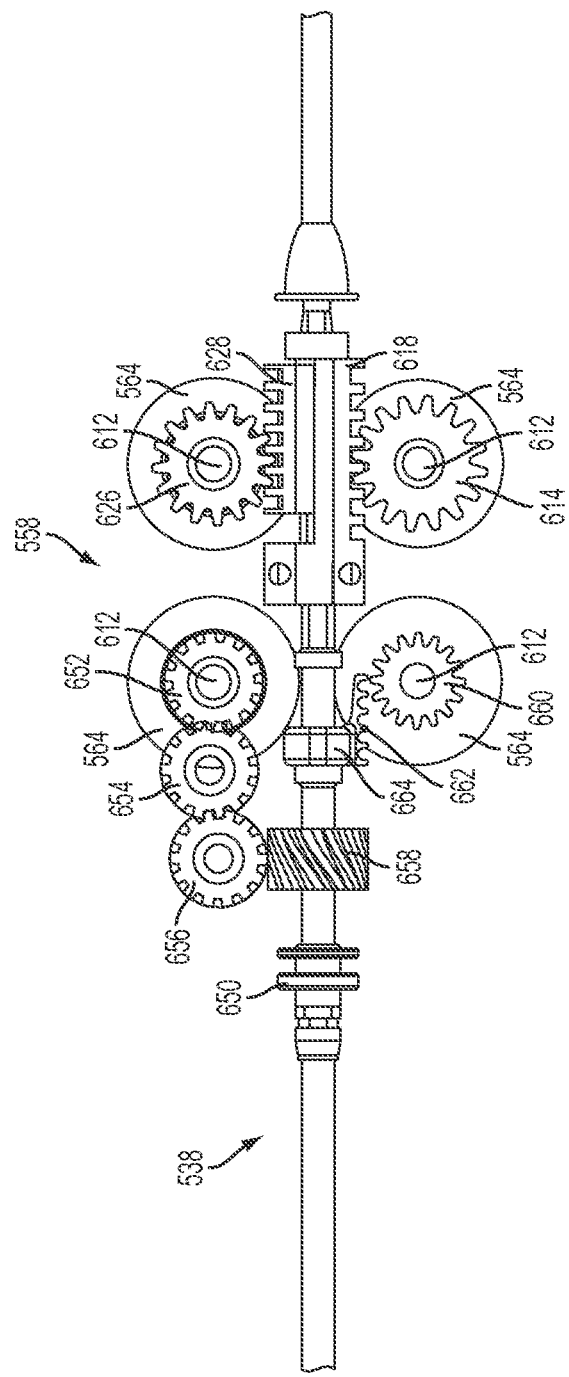

FIGS. 35-37 illustrate an alternate embodiment of the instrument mounting portion 558 showing an alternate example mechanism for translating rotation of the driven elements 564 into rotational motion about the axis of the shaft 538 and an alternate example mechanism for generating reciprocating translation of one or more members along the axis of the shaft 538. Referring now to the alternate rotational mechanism, a first spiral worm gear 652 is coupled to a second spiral worm gear 654, which is coupled to a third spiral worm gear 656. Such an arrangement may be provided for various reasons including maintaining compatibility with existing robotic systems 500 and/or where space may be limited. The first spiral worm gear 652 is coupled to a rotatable body 612. The third spiral worm gear 656 is meshed with a fourth spiral worm gear 658 coupled to the shaft assembly 538. A bearing 760 is coupled to a rotatable body 612 and is provided between a driven element 564 and the first spiral worm gear 738. Another bearing 760 is coupled to a rotatable body 612 and is provided between a driven element 564 and the third spiral worm gear 652. The third spiral worm gear 652 is meshed to the fourth spiral worm gear 658, which may be coupled to the shaft assembly 538 and/or to another component of the instrument 522, 523 for which longitudinal rotation is desired. Rotation may be caused in a CW and a CCW direction based on the rotational direction of the spiral worm gears 656, 658. Accordingly, rotation of the third spiral worm gear 656 about a first axis is converted to rotation of the fourth spiral worm gear 658 about a second axis, which is orthogonal to the first axis. As shown in FIGS. 36 and 37, for example, the fourth spiral worm gear 658 is coupled to the shaft 538, and a CW rotation of the fourth spiral worm gear 658 results in a CW rotation of the shaft assembly 538 in the direction indicated by 634CW. A CCW rotation of the fourth spiral worm gear 658 results in a CCW rotation of the shaft assembly 538 in the direction indicated by 634CCW. Additional bearings may be provided between the rotatable bodies and the corresponding gears. Any suitable bearings may be provided to support and stabilize the mounting and reduce rotary friction of shaft and gears, for example.

Referring now to the alternate example mechanism for generating reciprocating translation of one or more members along the axis of the shaft 538, the instrument mounting portion 558 comprises a rack and pinion gearing mechanism to provide reciprocating translation along the axis of the shaft 538 (e.g., translation of a tissue cutting element 555 of the RF surgical device 523). In one example embodiment, a third pinion gear 660 is coupled to a rotatable body 612 such that rotation of the corresponding driven element 564 causes the third pinion gear 660 to rotate in a first direction. The third pinion gear 660 is meshed to a rack gear 662, which moves in a linear direction. The rack gear 662 is coupled to a translating block 664. The translating block 664 may be coupled to a component of the device 522, 523, such as, for example, the tissue cutting element 555 of the RF surgical device and/or an overtube or other component which is desired to be translated longitudinally.

Figure 38:
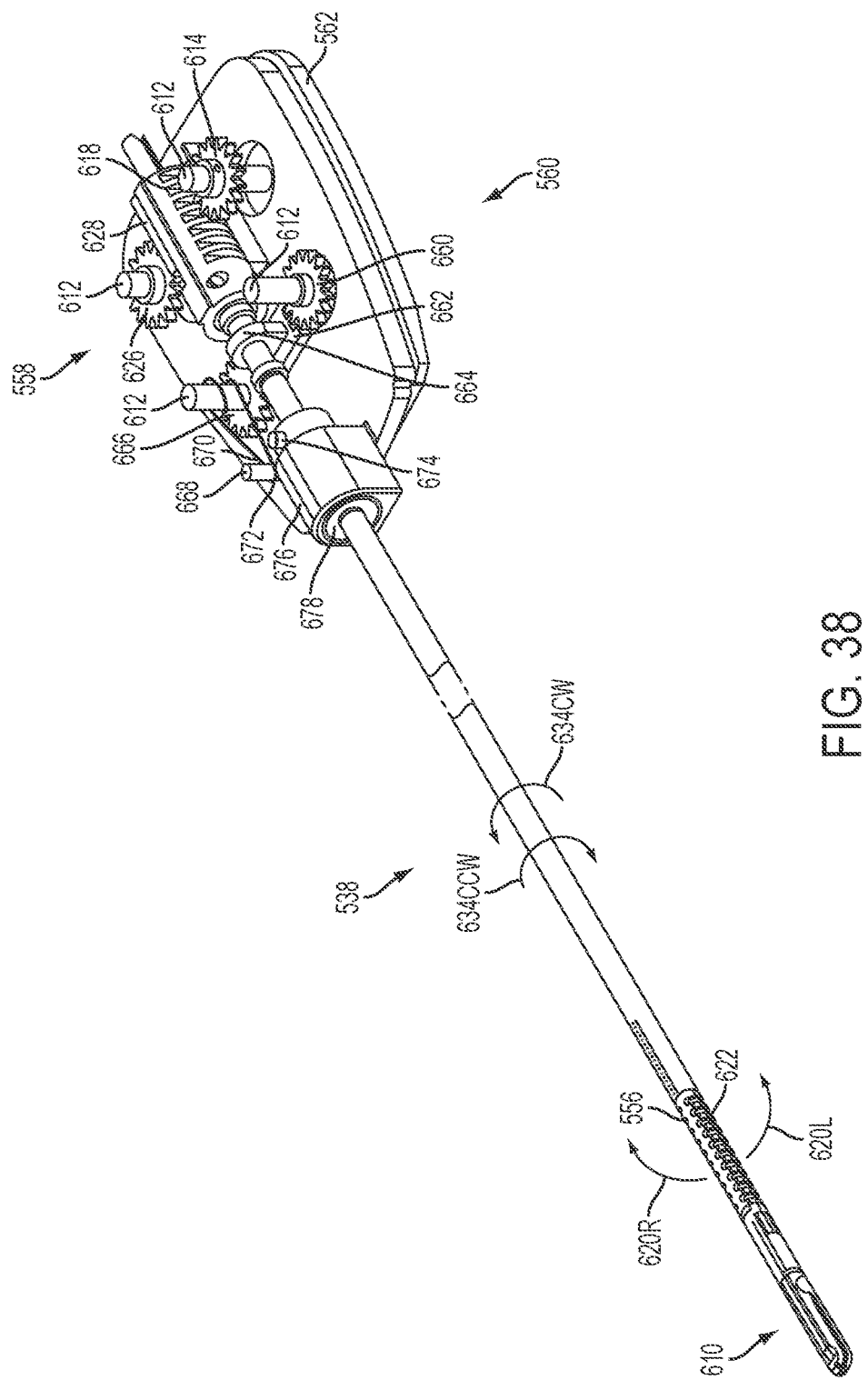
Figure 39:
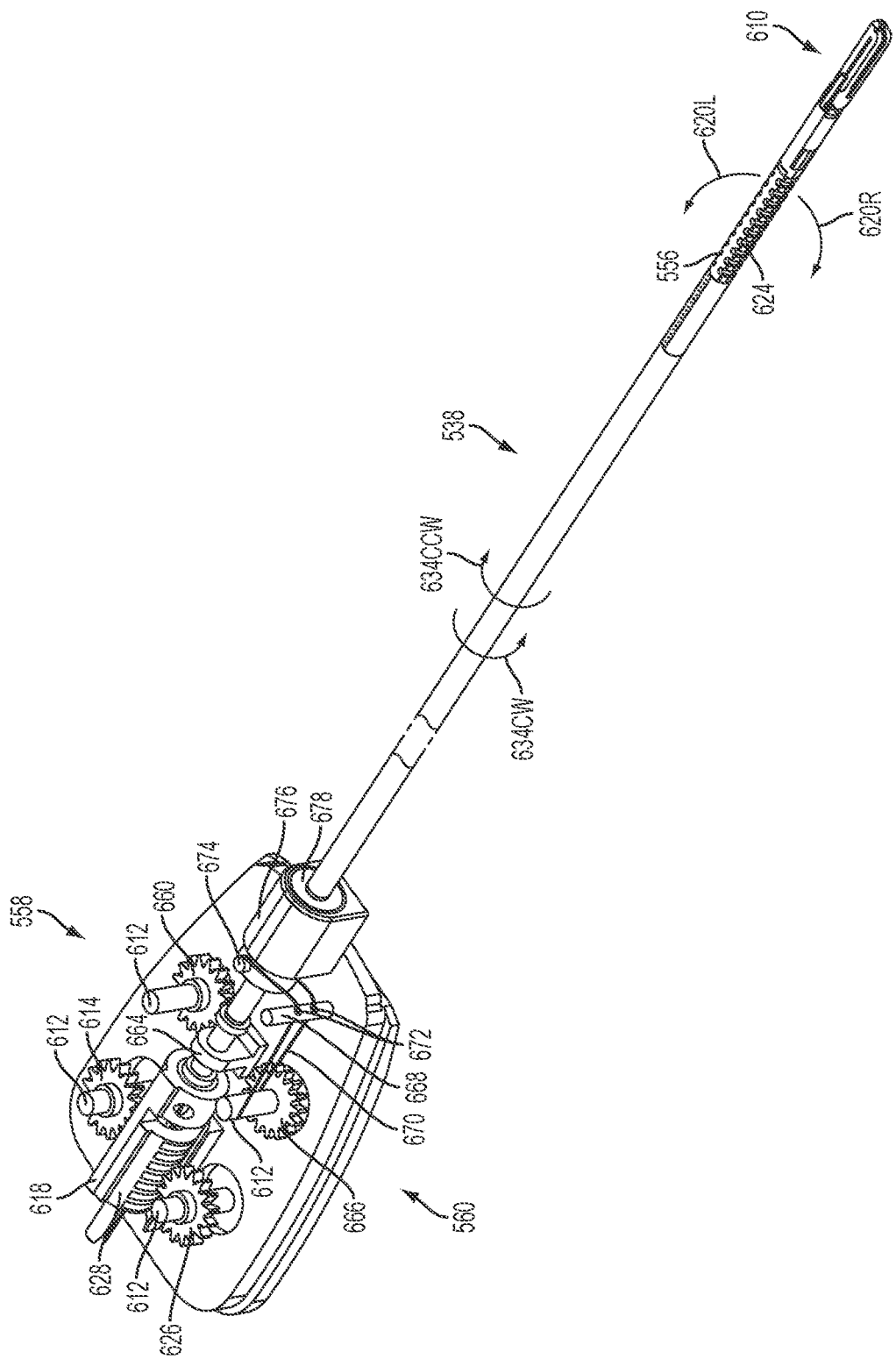
Figure 40:
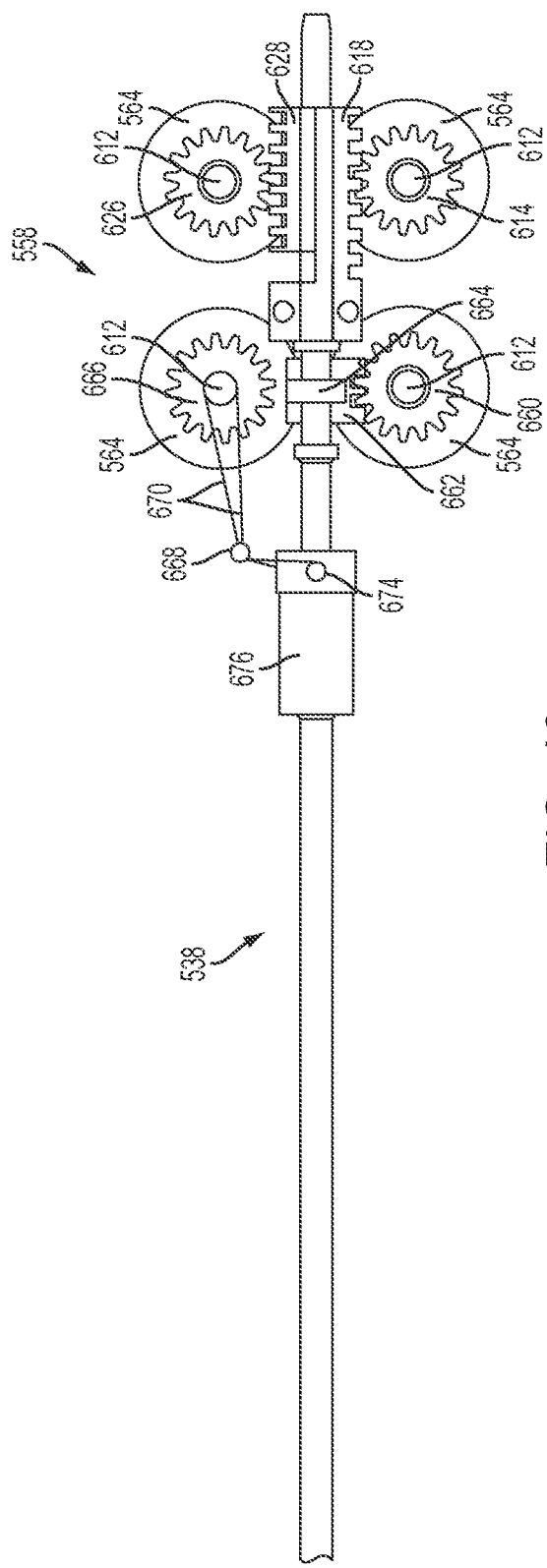
Figure 43:
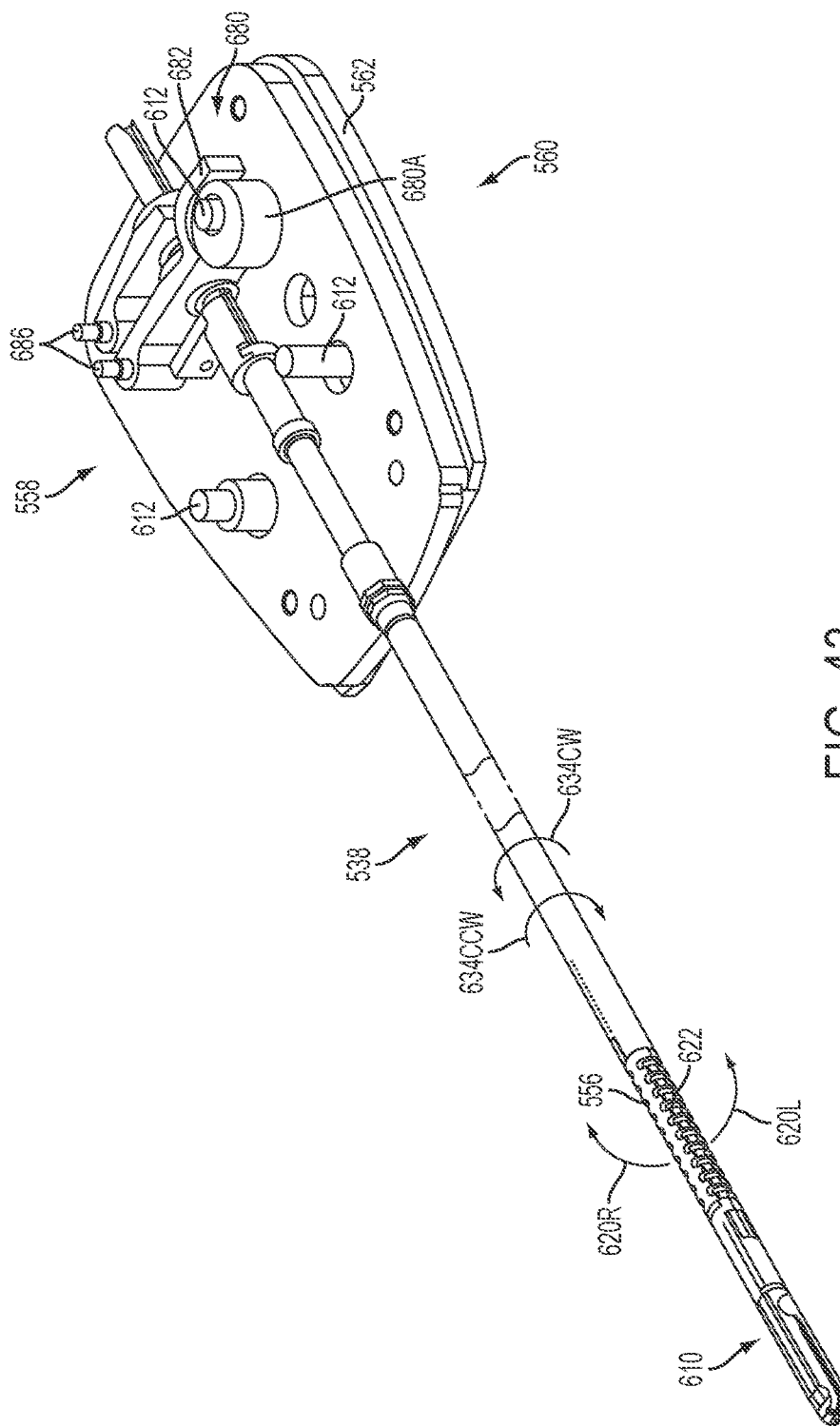
Figure 44:
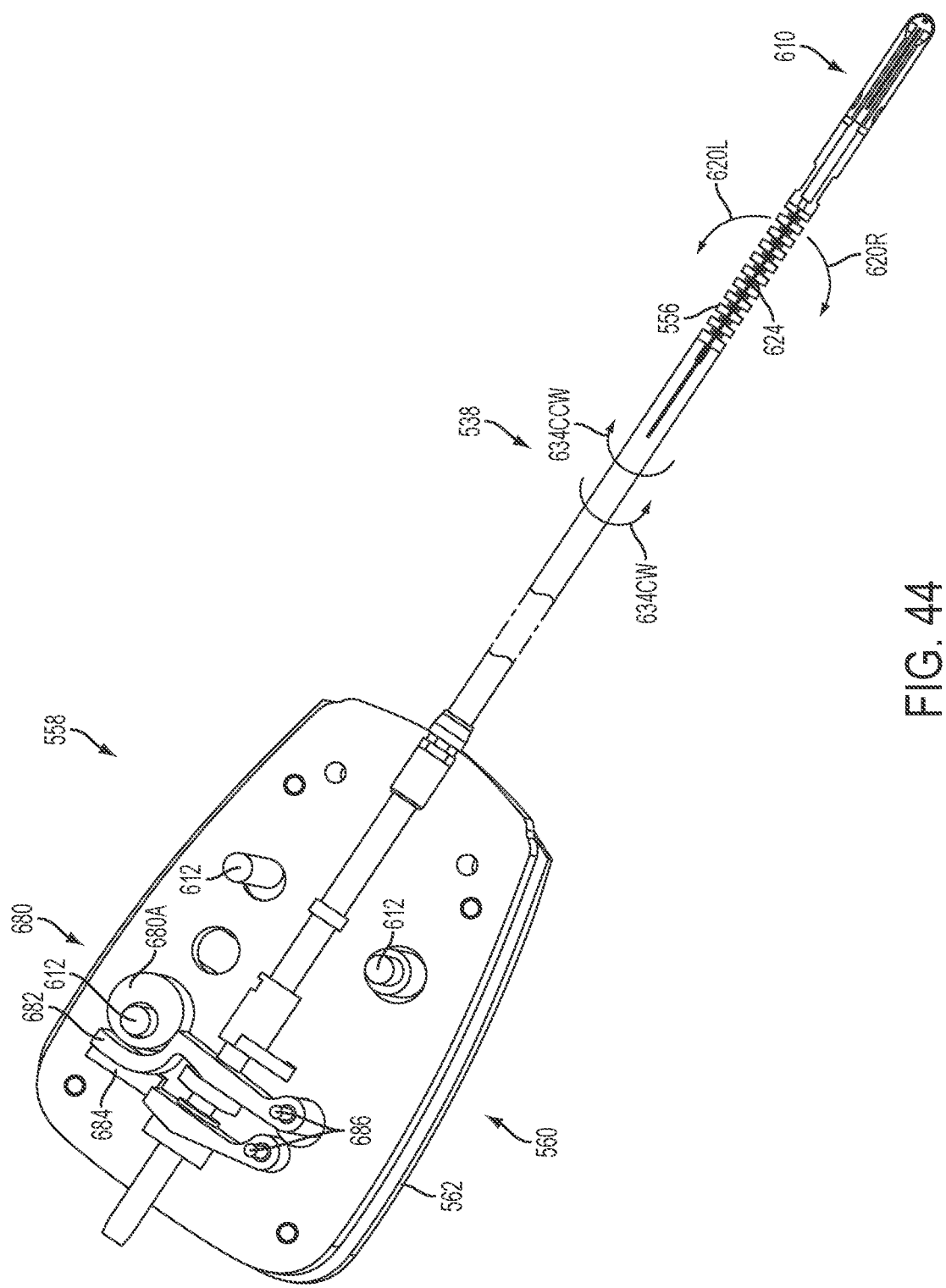
Figure 45:
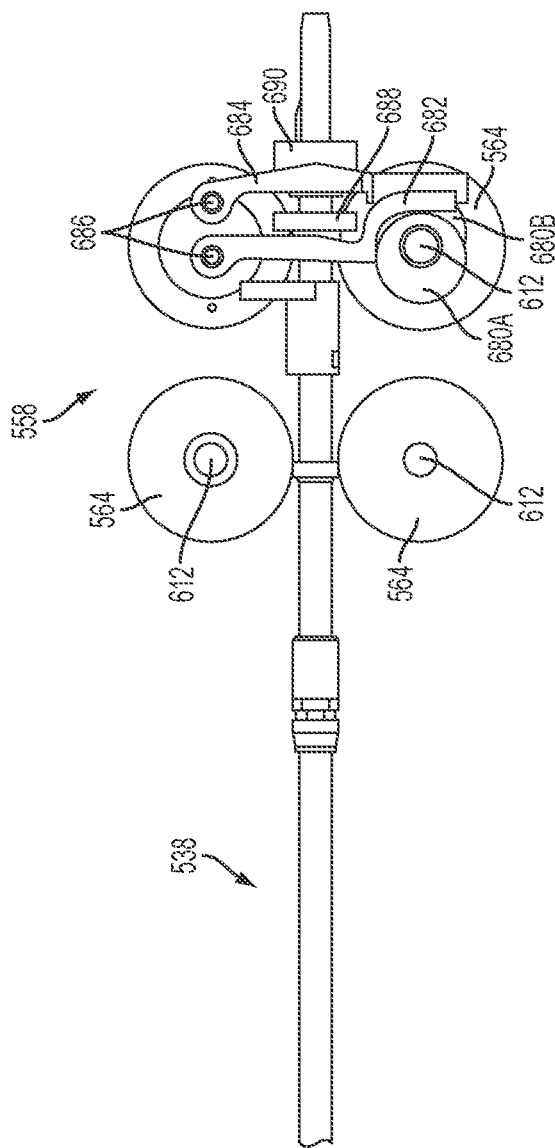

FIGS. 38-42 illustrate an alternate embodiment of the instrument mounting portion 558 showing another alternate example mechanism for translating rotation of the driven elements 564 into rotational motion about the axis of the shaft 538. In FIGS. 38-42, the shaft 538 is coupled to the remainder of the mounting portion 558 via a coupler 676 and a bushing 678. A first gear 666 coupled to a rotatable body 612, a fixed post 668 comprising first and second openings 672, first and second rotatable pins 674 coupled to the shaft assembly, and a cable 670 (or rope). The cable is wrapped around the rotatable body 612. One end of the cable 670 is located through a top opening 672 of the fixed post 668 and fixedly coupled to a top rotatable pin 674. Another end of the cable 670 is located through a bottom opening 672 of the fixed post 668 and fixedly coupled to a bottom rotating pin 674. Such an arrangement is provided for various reasons including maintaining compatibility with existing robotic systems 500 and/or where space may be limited. Accordingly, rotation of the rotatable body 612 causes the rotation about the shaft assembly 538 in a CW and a CCW direction based on the rotational direction of the rotatable body 612 (e.g., rotation of the shaft 538 itself). Accordingly, rotation of the rotatable body 612 about a first axis is converted to rotation of the shaft assembly 538 about a second axis, which is orthogonal to the first axis. As shown in FIGS. 38-39, for example, a CW rotation of the rotatable body 612 results in a CW rotation of the shaft assembly 538 in the direction indicated by 634CW. A CCW rotation of the rotatable body 612 results in a CCW rotation of the shaft assembly 538 in the direction indicated by 634CCW. Additional bearings may be provided between the rotatable bodies and the corresponding gears. Any suitable bearings may be provided to support and stabilize the mounting and reduce rotary friction of shaft and gears, for example.

Figure 46A:
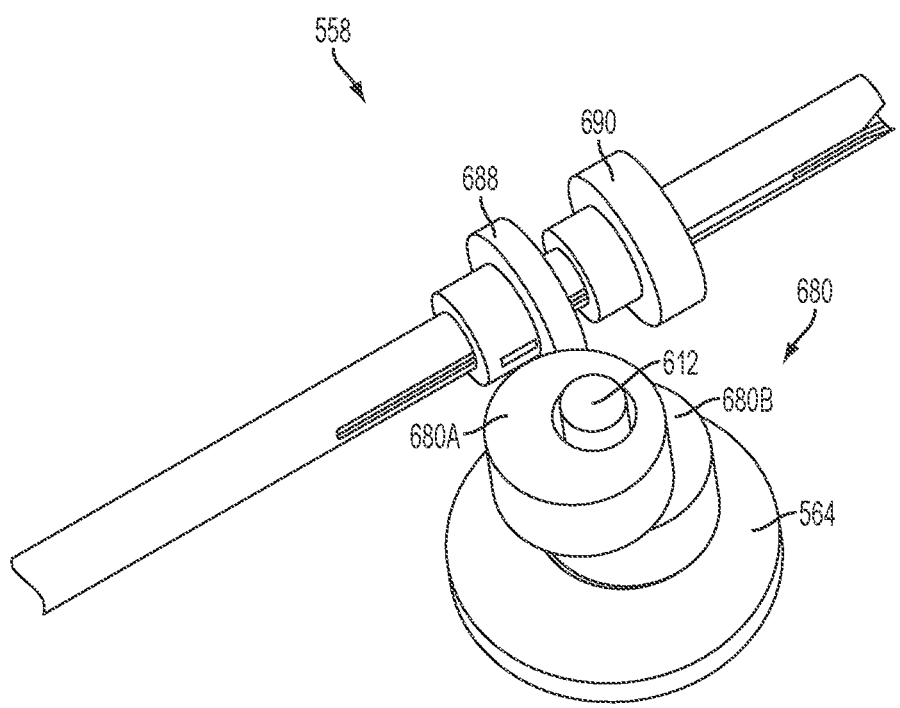

FIGS. 43-46A illustrate an alternate embodiment of the instrument mounting portion 558 showing an alternate example mechanism for differential translation of members along the axis of the shaft 538 (e.g., for articulation). For example, as illustrated in FIGS. 43-46A, the instrument mounting portion 558 comprises a double cam mechanism 680 to provide the shaft articulation functionality. In one example embodiment, the double cam mechanism 680 comprises first and second cam portions 680A, 680B. First and second follower arms 682, 684 are pivotally coupled to corresponding pivot spools 686. As the rotatable body 612 coupled to the double cam mechanism 680 rotates, the first cam portion 680A acts on the first follower arm 682 and the second cam portion 680B acts on the second follower arm 684. As the cam mechanism 680 rotates the follower arms 682, 684 pivot about the pivot spools 686. The first follower arm 682 may be attached to a first member that is to be differentially translated (e.g., the first articulation band 622). The second follower arm 684 is attached to a second member that is to be differentially translated (e.g., the second articulation band 624). As the top cam portion 680A acts on the first follower arm 682, the first and second members are differentially translated. In the example embodiment where the first and second members are the respective articulation bands 622 and 624, the shaft assembly 538 articulates in a left direction 620L. As the bottom cam portion 680B acts of the second follower arm 684, the shaft assembly 538 articulates in a right direction 620R. In some example embodiments, two separate bushings 688, 690 are mounted beneath the respective first and second follower arms 682, 684 to allow the rotation of the shaft without affecting the articulating positions of the first and second follower arms 682, 684. For articulation motion, these bushings reciprocate with the first and second follower arms 682, 684 without affecting the rotary position of the jaw 902. FIG. 46 shows the bushings 688, 690 and the dual cam assembly 680, including the first and second cam portions 680B, 680B, with the first and second follower arms 682, 684 removed to provide a more detailed and clearer view.

Figure 46B:
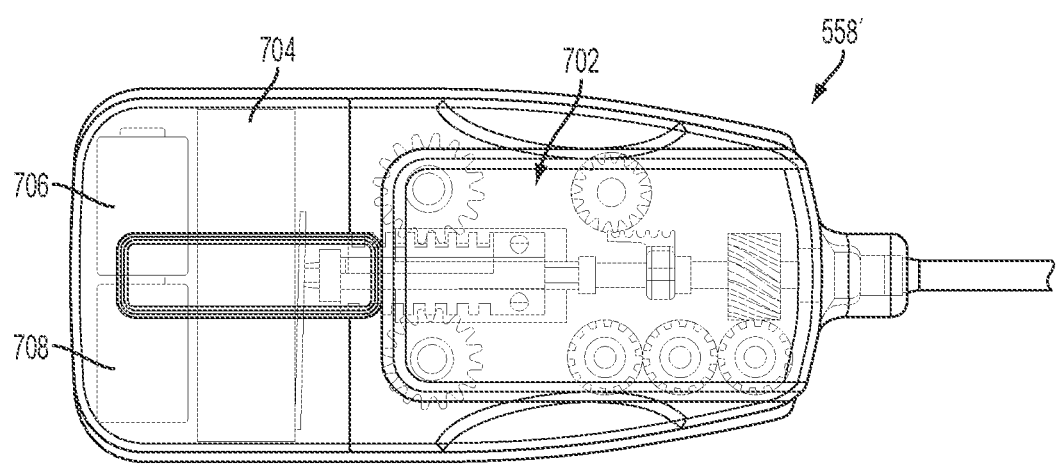
FIGS. 46B-46C illustrate one embodiment of a tool mounting portion comprising internal power and energy sources.
Figure 46C:
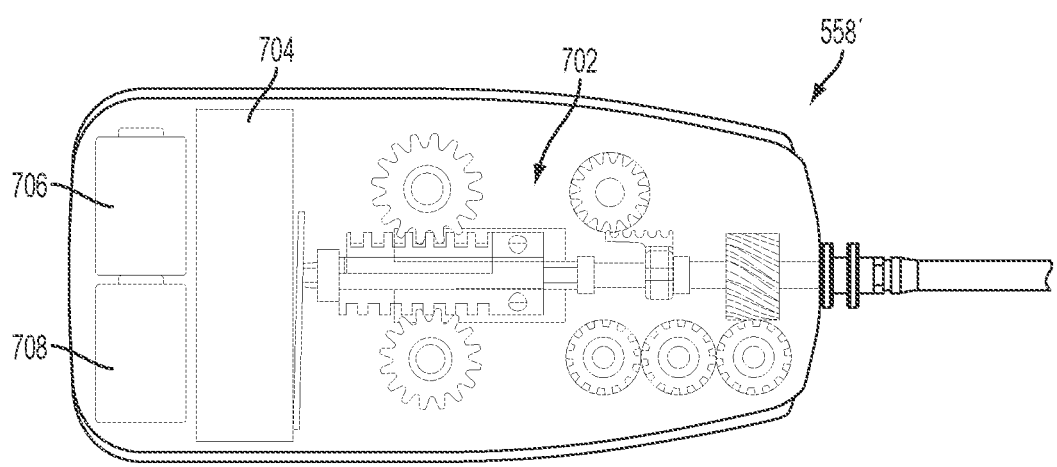

In various embodiments, the instrument mounting portion 558 may additionally comprise internal energy sources for driving electronics and provided desired ultrasonic and/or RF frequency signals to surgical tools. FIGS. 46B-46C illustrate one embodiment of a tool mounting portion 558' comprising internal power and energy sources. For example, surgical instruments (e.g., instruments 522, 523) mounted utilizing the tool mounting portion 558' need not be wired to an external generator or other power source. Instead, the functionality of the various generators 20, 320 described herein may be implemented on board the mounting portion 558.

As illustrated in FIGS. 46B-46C, the instrument mounting portion 558' may comprise a distal portion 702. The distal portion 702 may comprise various mechanisms for coupling rotation of drive elements 592 to end effectors of the various surgical instruments 522, 523, for example, as described herein above. Proximal of the distal portion 702, the instrument mounting portion 558' comprises an internal direct current (DC) energy source and an internal drive and control circuit 704. In the illustrated embodiment, the energy source comprises a first and second battery 706, 708. In other respects, the tool mounting portion 558' is similar to the various embodiments of the tool mounting portion 558 described herein above.

The control circuit 704 may operate in a manner similar to that described above with respect to generators 20, 320. For example, when an ultrasonic instrument 522 is utilized, the control circuit 704 may provide an ultrasonic drive signal in a manner similar to that described above with respect to generator 20. Also, for example, when an RF instrument 523 or ultrasonic instrument 522 capable of providing a therapeutic or non-therapeutic RF signal is used, the control circuit 704 may provide an RF drive signal, for example, as described herein above with respect to the module 23 of generator 20 and/or the generator 300. In some embodiments, the control circuit 704 may be configured in a manner similar to that of the control circuit 440 described herein above with respect to FIGS. 18B-18C.

Figure 47:
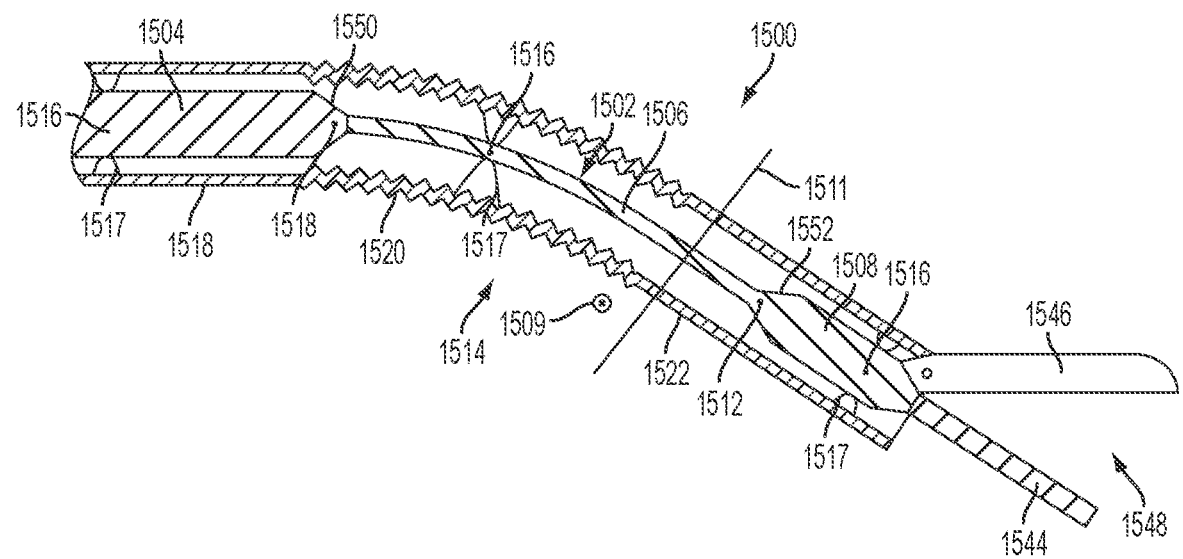
FIG. 47 illustrates a schematic cross-sectional view of a portion of one example embodiment of an ultrasonic medical instrument comprising first, second and third waveguide portions, where the second waveguide portion is substantially ½ of a resonant-longitudinal-wavelength long.

Various embodiments described herein comprise an articulatable shaft. When using an articulatable shaft, components running through the shaft from the end effector must be flexible, so as to flex when the shaft articulates. In various embodiments, this can be accomplished by utilizing waveguides that have flexible portions. For example, FIG. 47 illustrates a schematic cross-sectional view of a portion of one example embodiment of an ultrasonic medical instrument 1500 comprising first, second and third waveguide portions. In FIG. 47, the hand piece and the sheath-articulation control knobs, etc. of the ultrasonic medical instrument 1500 are omitted for clarity. In the example embodiment shown in FIG. 47, the ultrasonic medical instrument 1500 comprises a medical ultrasonic waveguide 1502 for transmitting ultrasonic energy from a transducer (not shown in FIG. 47) to an ultrasonic blade 1544. The medical ultrasonic waveguide 1502 has a length and includes first, second and third waveguide portions 1504, 1506 and 1508. The second waveguide portion 1506 is located lengthwise between the first and third waveguide portions 1504 and 1508; the first waveguide portion 1504 is located proximal the second waveguide portion 1506; and the third waveguide portion 1508 is located distal the second waveguide portion 1506. The first and third waveguide portions 1504 and 1508 each have a larger transverse area and the second waveguide portion 1506 has a smaller transverse area. The second waveguide portion 1506 is more bendable than either of the first and third waveguide portions 1504 and 1508. It is further noted that ultrasonic vibration can be any one, or any combination, of longitudinal, transverse, and torsional vibration. In some embodiments, the section 1506 may have a circular cross-section (e.g., a uniform cross-sectional radius).

Figure 47A:
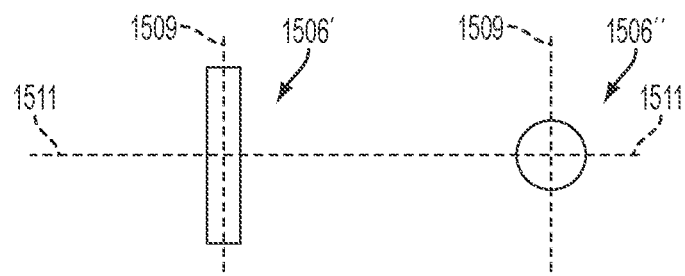
FIG. 47A illustrates cross sections for two example embodiments of the second waveguide portion of FIG. 47.

In some embodiments the second bendable waveguide portion 1506 may not have a uniform cross-sectional radius. For example, FIG. 47A illustrates cross sections for two example embodiments of the waveguide portion 1506. The waveguide portion 1506' is illustrated in relation to two axes 1509, 1511, also shown in FIG. 47. In various embodiments, the waveguide portion 1506' may have a cross sectional length along axis 1511 that is less than its cross sectional dimension along axis 1509. In some embodiments, the cross sectional length along the axis 1509 may be equal to the cross sectional length of the other waveguide portions 1504, 1506. The waveguide portion 1506' may be bendable along the axis 1509. Referring now to waveguide portion 1506", its cross sectional lengths along the axis 1509, 1511 may be the same, providing the waveguide portion 1506" with a greater range of directions for bending.

In some example embodiments, the medical ultrasonic waveguide 1502 is a monolithic (e.g., the blade portion 1544 is integral to the waveguide 1502). Also, in some example embodiments, the medical ultrasonic waveguide 1502 includes first and second longitudinal vibration antinodes 1510 and 1512. The first waveguide portion 1504 may transition to the second waveguide portion 1506 proximate the first longitudinal vibration antinode 1510; and the second waveguide portion 1506 may transition to the third waveguide portion 1508 proximate the second longitudinal vibration antinode 1512. In some example embodiments, as illustrated by FIG. 47, the second waveguide portion 1506 is substantially % of a resonant-longitudinal-wavelength long.

In one example application of the embodiment of FIG. 47, the ultrasonic medical instrument 1500 also includes a user-actuated articulated sheath 1514 which surrounds the medical ultrasonic waveguide 1502. In various example embodiments, the medical ultrasonic waveguide 1502 includes three (meaning at least three) longitudinal vibration nodes 1516 located, one each, on the first, second and third waveguide portions 1504, 1506 and 1508. It is noted that one or more additional longitudinal vibration nodes may, or may not, be present between any one or two of the three longitudinal vibration nodes 1516. In one modification, the sheath 1514 contacts (e.g., directly contacts or indirectly contacts through at least one intervening member 1517 such as a silicone intervening member) the first, second and third waveguide portions 1504, 1506 and 1508 at a corresponding one of the three longitudinal vibration nodes 1516. In one example, the sheath 1514 includes a rigid first sheath portion 1518 contacting the first waveguide portion 1504 at the first longitudinal vibration node (the leftmost node 1516 of FIG. 47), a flexible second sheath portion 1520 contacting the second waveguide portion 1506 at the second longitudinal vibration node (the middle node 1516 of FIG. 47), and a rigid third sheath portion 1522 contacting the third waveguide portion 1508 at the third longitudinal vibration node (the rightmost node 1516 of FIG. 47). In some example embodiments, the sheath 1514 has only two articulation positions (e.g., straight and fully articulated). In other example embodiments, the sheath 1514 has a number of intermediate bent positions between a straight position and a fully articulated position depending on the number of energy efficient curves the waveguide 1502 can be formed to. In some example embodiments, such energy efficient curves minimize vibrational energy going into non-longitudinal vibrational modes.

Figure 48:
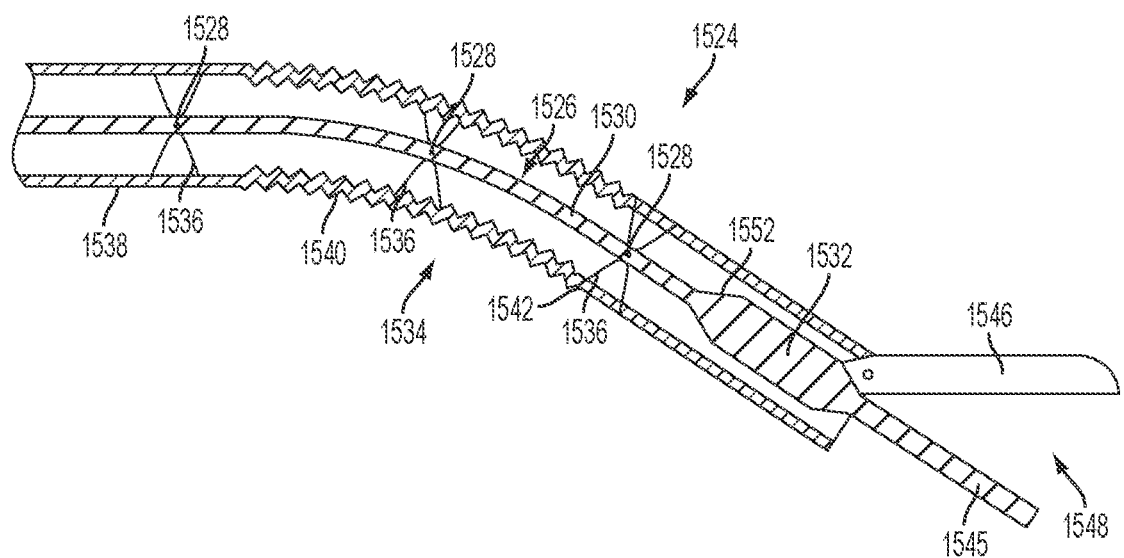
FIG. 48 illustrates a schematic cross-sectional view of a portion of one example embodiment of an ultrasonic medical instrument comprising first and second waveguide portions, where the first waveguide portion spans multiple ½ resonant longitudinal wavelengths.

FIG. 48 illustrates a schematic cross-sectional view of a portion of one example embodiment of an ultrasonic medical instrument 1524 comprising first and second waveguide portions 1530, 1532, where the first waveguide portion 1530 spans multiple % resonant longitudinal wavelengths. In the example embodiment show in FIG. 48, a medical ultrasonic waveguide 1526 includes at least two longitudinal vibration nodes 1528 located on the first waveguide portion 1530. In one variation, a sheath 1534 contacts (e.g., directly contacts or indirectly contacts through at least one intervening member 1536 such as a silicone intervening member) the first waveguide portion 1530 at the at-least-two longitudinal vibration nodes 1528. In some example embodiments, the sheath 1534 includes two rigid sheath portions 1538 and 1542 and one flexible sheath portion 1540, wherein the flexible sheath portion 1540 contacts the first waveguide portion 1530 at least one of the two longitudinal vibration nodes 1528, and wherein the flexible sheath portion 1540 is disposed between the two rigid sheath portions 1538 and 1542. In one example embodiment, the two rigid sheath portions 1538 and 1542 each contact the second waveguide portion 1532 at a corresponding one of the at-least-two longitudinal vibration nodes 1528.

Referring now to FIG. 47, the waveguide 1502 may comprise a blade portion 1544 adapted to contact and ultrasonically treat patient tissue. The blade portion 1544 may be disposed at a distal end of the waveguide 1502 (e.g., distal of the third blade portion 1508 of the blade 1502). In one example embodiment, the surgical instrument 1500 may also comprise a user-actuated clamp arm 1546 pivotally attached to the sheath 1514, 1534 proximate the blade portion 1544, wherein the clamp arm 1546 and the medical ultrasonic waveguide 1502 at least in part define an ultrasonic surgical shears 1548. The tissue pad and clamping arm control mechanism has been omitted from FIG. 47. Referring again to FIG. 48, the medical ultrasonic waveguide 1526 may also comprise a blade portion 1545, similar to the blade portion 1544, and disposed at a distal end of the first waveguide portion 1532. The blade portion 1545 may also be adapted to contact and ultrasonically treat patient tissue. The instrument 1524 of FIG. 48 may also comprise a clamp arm 1546, defining, with the blade portion 1545, an ultrasonic surgical shears 1548.

In various example embodiments, certain portions of the waveguides 1502, 1526 are substantially rigid. For example, first and third portions 1504 and 1508 of the waveguide 1502 may be substantially rigid. The first portion 1532 of the waveguide 1526 may be substantially rigid. Referring again to FIG. 47, the medical ultrasonic waveguide 1502 may include first and second neck portions 1550 and 1552 joining, respectively, the first and second waveguide portions 1504 and 1506 and the second and third waveguide portions 1506 and 1508. (A similar neck portion 1552 may join the first and second waveguide portions 1530, 1532 of the waveguide 1526.)

In one modification, the medical ultrasonic waveguide 1502 is substantially cylindrical from the first waveguide portion 1504 to the third waveguide portion 1508, wherein the first, second and third waveguide portions 1504, 1506 and 1508 each have a substantially constant diameter, and wherein the diameter of the second waveguide portion 1506 is smaller than the diameter of either of the first and third waveguide portions 1504 and 1508. In some example embodiments, the diameter of the second waveguide portion 1506 is between substantially one and two millimeters, and the diameter of the first and third waveguide portions is between substantially three and five millimeters. In one choice of materials, the medical ultrasonic waveguide 1502 consists essentially of a titanium alloy. In one modification, the medical ultrasonic waveguide 1502 includes first and second longitudinal vibration antinodes 1510 and 1512, and the first neck portion 1550 is disposed proximate the first longitudinal vibration antinode 1510 and the second neck portion 1552 is disposed proximate the second longitudinal vibration antinode 1512.

Figure 49:
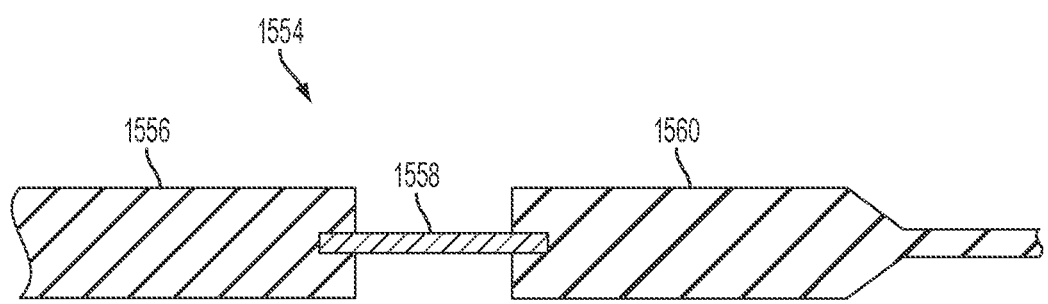
FIG. 49 illustrates a schematic cross-sectional view of one example embodiment of an ultrasonic waveguide for use with a medical instrument and comprising first and second waveguide portions, where a first waveguide portion is joined to a second waveguide portion by a dowel press fit.

FIG. 49 illustrates a schematic cross-sectional view of one example embodiment of an ultrasonic waveguide 1554 for use with a medical instrument and comprising first and second waveguide portions, where a first waveguide portion 1556 is joined to a second waveguide portion 1558 by a dowel press fit. In the example illustrated in FIG. 49, the second waveguide portion 1558 is also coupled to a third waveguide portion 1560 by a dowel press fit. In various example embodiments, the second waveguide portion 1558 consists essentially of titanium or nitinol. In the same or a different illustration, the length of the second waveguide portion 1558 is less than ½ wavelength (a wavelength being the length of a resonant-longitudinal-wavelength of the medical ultrasonic waveguide which depends essentially on the material of the waveguide and the frequency at which it is run) and in one example is less than ⅛ wave.

Figure 50:
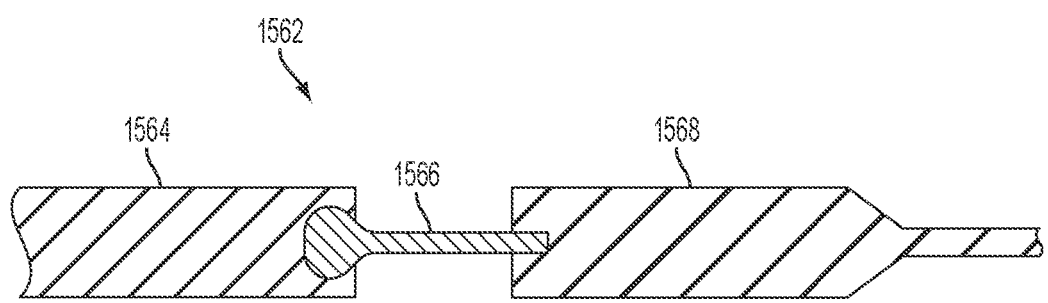
FIG. 50 illustrates a schematic cross-sectional view of one example embodiment of an ultrasonic waveguide for use with a medical instrument and comprising first and second waveguide portions, where the first waveguide portion is joined to the second waveguide portion by a ball-and-socket type attachment.

FIG. 50 illustrates a schematic cross-sectional view of one example embodiment of an ultrasonic waveguide 1564 for use with a medical instrument. Like the waveguide 1554, the waveguide 1564 is not a monolithic waveguide. The waveguide 1564 may comprise first and second waveguide portions 1564, 1566, where the first waveguide portion 1564 is joined to the second waveguide 1566 portion by a ball-and-socket type attachment. The second waveguide portion 1566 may also be joined to a third waveguide portion 1568 in any suitable manner. In the example of FIG. 50, the second waveguide portion 1566 is joined to the third waveguide portion 1568 via a dowel press fit. Other attachments between waveguide portions are left to those skilled in the art.

Figure 51:
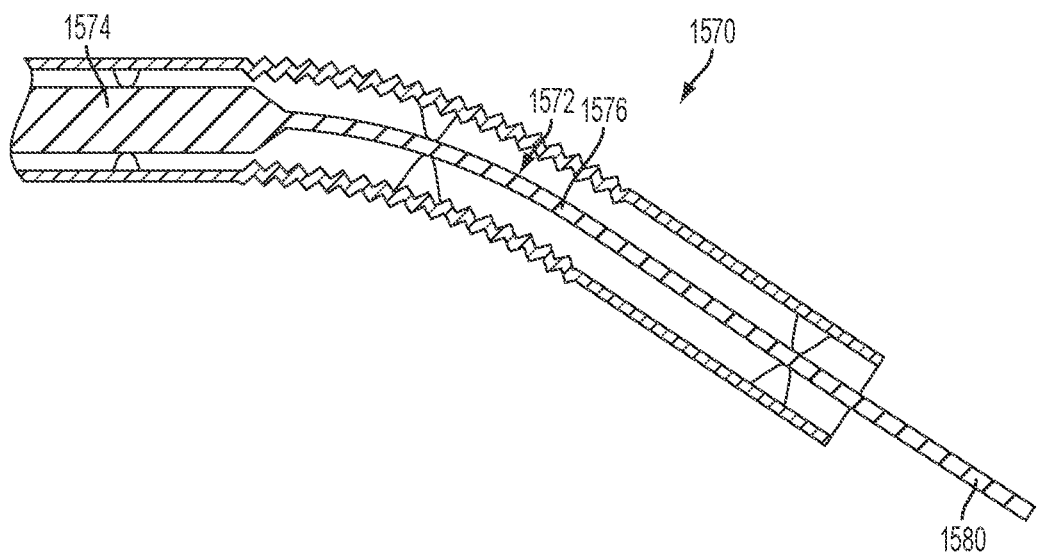
FIG. 51 illustrates a schematic cross-sectional view of a portion of another embodiment of an ultrasonic medical instrument comprising a medical ultrasonic waveguide having a length and including a proximal waveguide portion and a distal waveguide portion.

FIG. 51 illustrates a schematic cross-sectional view of a portion of another embodiment of an ultrasonic medical instrument 1570 comprising a medical ultrasonic waveguide 1572 having a length and including a proximal waveguide portion 1574 and a distal waveguide portion 1576. The proximal waveguide portion 1574 has a larger transverse area and the distal waveguide portion 1576 has a smaller transverse area. The distal waveguide portion 1576 bends more easily than does the proximal waveguide portion 1574. The distal waveguide portion 1576 includes a distal end portion 1580 adapted to contact and ultrasonically treat patient tissue. In various example embodiments, the additional ¼ wave needed to neck up and create the larger diameter end effector of the embodiment of FIG. 47 is eliminated making it possible to place the articulation joint closer to the distal end of the ultrasonic medical instrument 1570. The embodiments, applications, etc. shown in FIGS. 47-50 are equally applicable (without the presence of the third waveguide portion) to the embodiment of FIG. 51.

Figure 52:
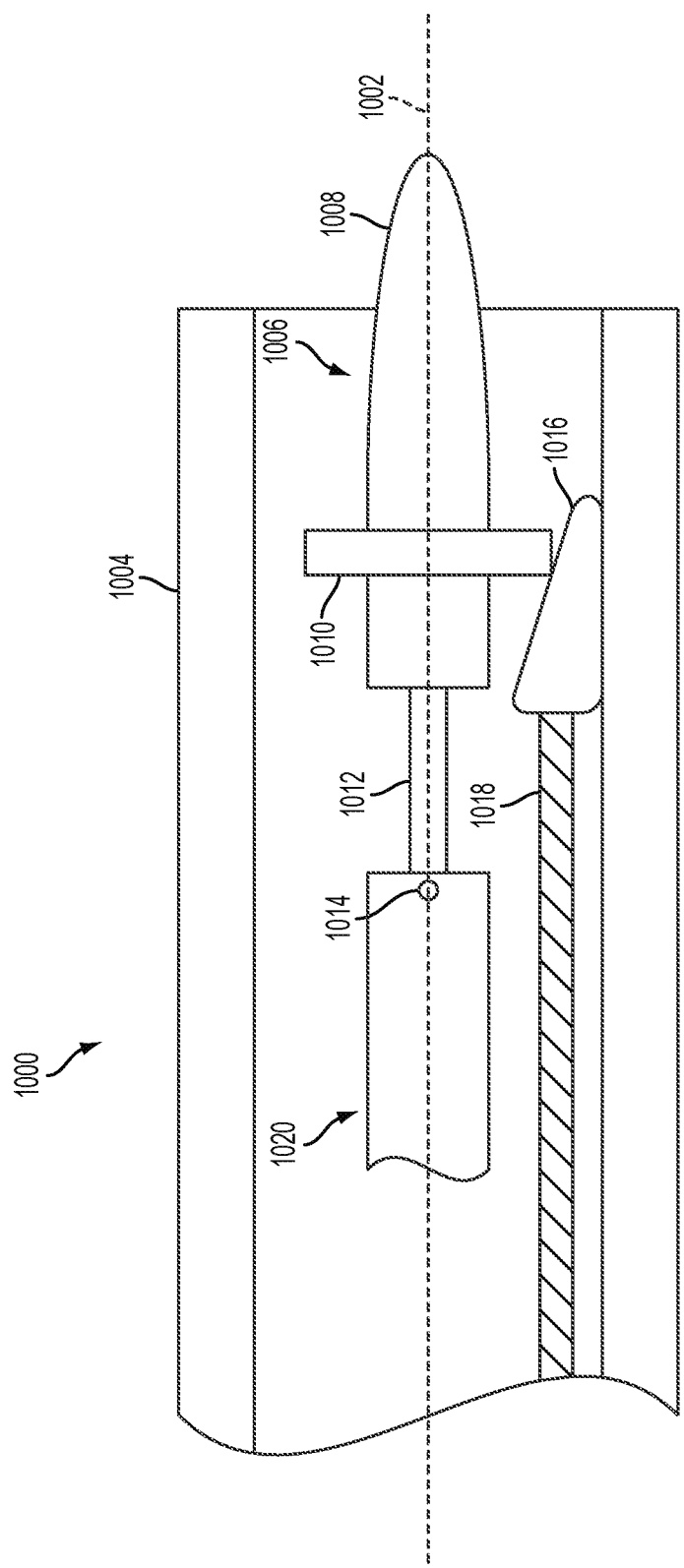
FIG. 52 illustrates one embodiment of a shaft that may be utilized with various surgical instruments, including those described herein.

FIG. 52 illustrates one embodiment of a shaft 1000 that may be utilized with various surgical instruments, including those described herein. An end effector 1006 is positioned within a shaft body 1004 and may comprise an ultrasonic blade 1008. The ultrasonic blade 1008 may be acoustically coupled to a waveguide 1020 extending proximally from the blade 1008. The waveguide 1020 may comprise a bendable portion 1012, such as the bendable portions 1506, 1530, 1576, etc., described herein above. Also positioned within the shaft 1000 is a wedge 1016 coupled to a translating cable 1018 that extends proximally from the wedge 1016. The wedge 1016 may reciprocate proximally and distally under the control of the cable 1018. The cable 1018 may be made of any suitable material including, for example, a material that is rigid enough to provide a distally directed force on the wedge 1016 when the cable 1018 is pushed distally (e.g., from a handle, from a robotic instrument mounting portion, etc.). In some embodiments, the cable 1018 may be made from a metal material.

Figure 53:
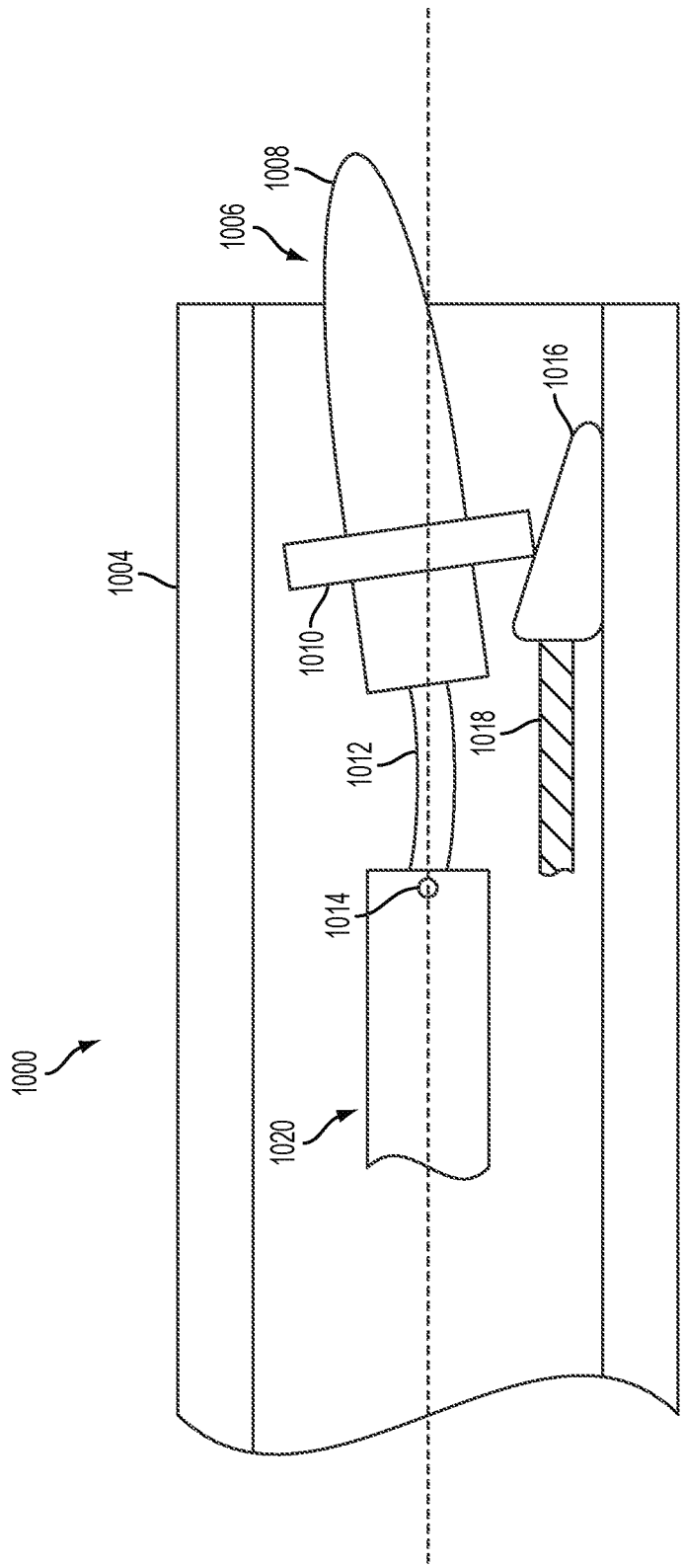
FIG. 53 illustrates one embodiment of the shaft of FIG. 52 with the wedge translated distally and the blade pivoted, as described.

The ultrasonic waveguide 1020 may be coupled to the shaft body 1004 at a pivot point 1014. For example, the pivot point 1014 may represent a pin received through the waveguide 1020 to hold the waveguide stationary relative to the shaft body 1004 at about the pivot point 1014. The pivot point may be located proximally from the bendable portion 1012. Distal of the bendable portion 1012 of the waveguide 1020, the waveguide 1020 and/or ultrasonic blade 1008 defines a flange 1010. As the wedge 1016 is translated distally, it may come into contact with the flange 1010. As the flange 1010 rides up the wedge 1016, the waveguide 1020 may pivot about the pivot point, tending to pivot the blade 1008 and waveguide 1020 away from a longitudinal axis 1002 of the shaft 1000. FIG. 53 illustrates one embodiment of the shaft 1000, with the wedge 1016 translated distally and the blade 1008 pivoted, as described. Proximal translation of the wedge 1016 from the position shown in FIG. 53 may release the force on the flange 1010 tending to cause deflection of the blade 1008. Absent the force, the blade 1008 and waveguide 1020 may return to the resting position illustrated in FIG. 52. For example, the blade 1008 and/or waveguide 1020 may be constructed from a resilient material that regains its original shape after bending. For example, in various embodiments, the wedge 1016 may not push the blade 1008 and/or the waveguide 1020 past their respective points of plasticity. The flange 1010 and pivot point 1014 may both be positioned at nodes of the waveguide 1020 (e.g., portions where there is substantially no movement of the waveguide 1020). In some embodiments, the flange 1010 and pivot point 1014 may be separated by a single wavelength.

The wedge 1016 and cable 1018 may be translated distally and proximally according to any suitable method or mechanism. For example, when the shaft 1000 is used in conjunction with a manual or hand held surgical instrument, the cable 1018 may be translated distally and proximally in a manner similar to that described herein above with respect to the reciprocating tubular actuating member 58 of the instrument 10 and/or the axially moving member 378 of the instrument 300. Also, for example, when the shaft 1000 is used in conjunction with a surgical robot, the cable 1018 may be translated distally and proximally in a manner similar to that described above with respect to the tissue cutting element 555 of the instrument 310.

Figure 54:
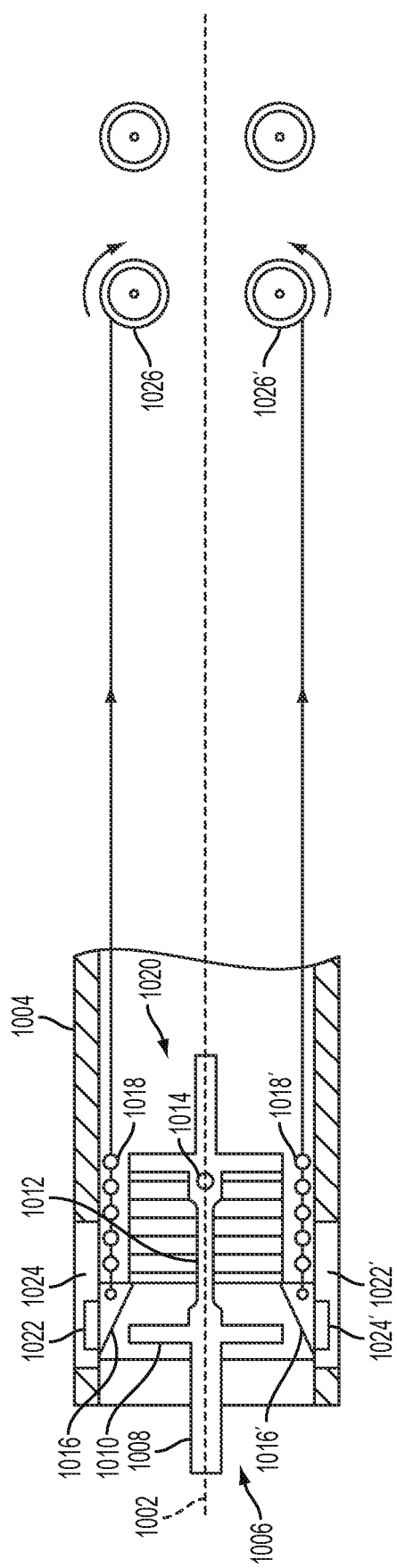
FIG. 54 illustrates an alternative embodiment of the shaft of FIG. 52 comprising several additional features.

FIG. 54 illustrates an alternative embodiment of the shaft 1000 comprising several additional features. For example, the shaft 1000, as illustrated in FIG. 54 comprises an optional second wedge 1016' and cable 1018'. The second wedge 1016' and cable 1018' may operate similar to the wedge 1016 and cable 1018 described herein above. The second wedge 1016' and cable 1018', however, may be offset from the first wedge 1016 and cable 1018 about the longitudinal axis such that distal translation of the first wedge 1016 causes the end effector 1008 and waveguide 1020 to pivot in a first direction and distal translation of the second wedge 1016' causes the end effector 1008 and waveguide 1020 to pivot in a second direction. In various example embodiments, the first and second directions may be 180° opposed from one another about the longitudinal axis. In the example embodiment illustrated in FIG. 54, the shaft body 1004 also comprises slots 1022, 1022' for receiving slot members 1024, 1024' of the respective wedges 1016, 1016'. The slots 1022, 1022' and slot members 1024, 1024' may serve to maintain axially alignment of the respective wedges 1016, 1016'.

FIG. 54 also illustrates one example mechanism for translating the wedges 1016, 1016' and cables 1018, 1018' distally and proximally (e.g., in a robotic surgical embodiment). For example, each cable 1018, 1018' may be wound around respective spools 1026, 1026'. The spools 1026, 1026', in turn, may be coupled to a robotically controlled component such as, for example, respective rotatable bodies 612 as described herein. Clockwise and counter clockwise rotation of the spools 1026, 1026' may wind and unwind the cables 1018, 1018' providing alternating distal and proximally translation to the wedges 1016, 1016'.

Figure 56:
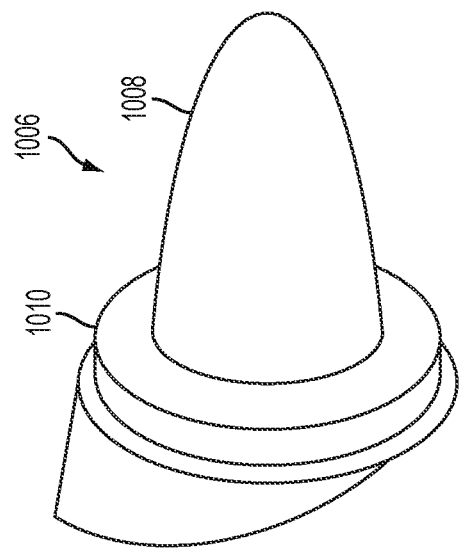
FIG. 56 illustrates the wedge in conjunction with an end effector comprising an ultrasonic blade as well as a flange.
Figure 55:
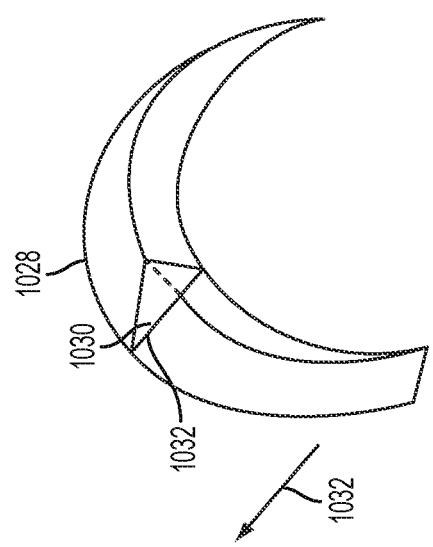
FIG. 55 illustrates one embodiment of an example wedge having a curved or rounded shape.

The wedges 1016, 1016' of FIGS. 52-54 are shown in two dimensions. Wedges according to various embodiments, however, can have different three dimensional shapes. FIG. 55 illustrates one embodiment of an example wedge 1028 having a curved or rounded shape. A cross-section 1030 of the wedge 1028 shows a wedge face portion 1032 for contacting the flange 1010. The arrow 1032 indicates a distal direction along the longitudinal axis 1002. FIG. 56 illustrates the wedge 1028 in conjunction with an end effector 1006 comprising an ultrasonic blade 1008 as well as a flange 1010.

Figure 58:
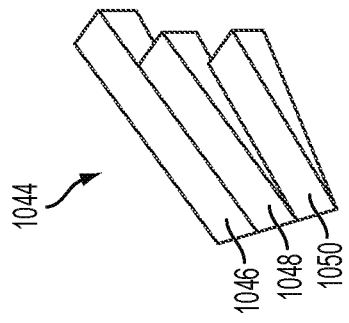
FIG. 58 illustrates one embodiment of a keyed wedge comprising steps matching the notches of the keyed flange of FIG. 57.
Figure 57:
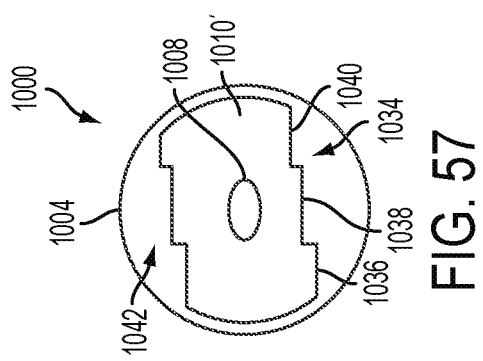
FIG. 57 illustrates a cross-section of one embodiment of the shaft showing a keyed flange.

FIG. 57 illustrates a cross-section of one embodiment of the shaft 1000 showing a keyed flange 1010'. The flange 1010' comprises a first keyed surface 1038 for receiving a keyed wedge. The keyed surface 1038 defines first, second and third notches 1036, 1038, 1040 for receiving a steps of a correspondingly keyed wedge. FIG. 58 illustrates one embodiment of a keyed wedge 1044 comprising steps 1046, 1048, 1050 matching the notches 1036, 1038, 1040 of the keyed flange 1010'. In various embodiments, the longitudinal slopes of the various steps 1046, 1048, 1050 are equal. The keyed flange 1010' is also illustrated with an optional second keyed surface 1042, for example, for interfacing with a second keyed wedge (not shown) in a multi-wedge embodiment such as that shown in FIG. 54. Also, although three notches 1036, 1038, 1040 and three steps 1046, 1048, 1050 are shown, it will be appreciated that keyed surfaces 1038 and wedges 1044 may have more or fewer notches and steps.

Figure 59:
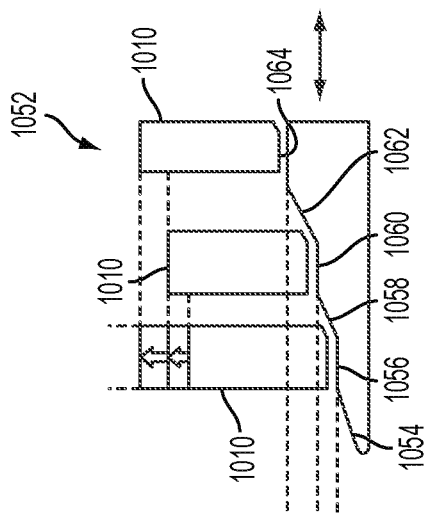
FIG. 59 illustrates a wedge for use with the shaft, the wedge having a stepped profile.

FIG. 59 illustrates a wedge 1052 for use with the shaft 1000, the wedge 1052 having a stepped profile. The stepped profile may allow the wedge 1052 to pivot the ultrasonic blade 1008 and waveguide 1020 by discrete amounts. For example, as the wedge 1052 is translated distally, a first wedge portion 1054 pushes the flange 1010, pivoting the blade 1008 and waveguide 1020 by a first amount. As the flange 1010 reaches a first flat portion 1056, it may be held, pivoted by the first amount, until the flange 1010 encounters a second wedge portion 1058. The second wedge portion 1058 may pivot the blade 1008 and waveguide 1020 by a second amount, which is again held as the flange 1010 slides across a second flat portion 1060. A third wedge portion 1062 and third flat portion 1064 may operate in a similar fashion as the wedge 1052 continues to translate distally. When the wedge 1052 is retracted proximally, the flange 1010 (and therefore the blade 1008 and waveguide 1020) may transition back through the discrete pivot amounts associated with each wedge portion and flat portion pair.

FIG. 60 illustrates one example embodiment of a shaft 1066 for use with various surgical instruments, including those described herein having a cammed articulation mechanism. Positioned within the shaft 1066 is a waveguide 1020 coupled to the shaft 1066 at a pivot point 1014. The waveguide 1020 is acoustically coupled to an ultrasonic blade 1008, as described above. The flange 1068 may be a cammed flange defining a waveguide cam feature 1072 configured to contact a shaft cam feature 1070 to deflect the waveguide 1020 and blade 1008 about the pivot point 1012. FIG. 61 illustrates a cross-sectional view of the shaft 1066 providing a view of the shaft cam feature 1070 and waveguide cam feature 1072. In various example embodiments, the shaft body 1004 may be rotatable about the longitudinal axis 1002. As the shaft body 1004 rotates, the shaft cam feature 1070 may come into contact with the waveguide cam feature 1072, causing the waveguide 1020 and blade 1008 to pivot about the pivot point 1014 away from the shaft cam feature 1070.

In some example embodiments, as illustrated in FIG. 61, the flange 1068 may define additional waveguide cam features 1074, 1076, 1078 that may operate in a manner similar to the waveguide cam feature 1072. For example, as the shaft body 1004 rotates, the shaft cam feature 1070 may, in turn, contact each of the additional waveguide cam features 1074, 1076, 1078, causing the waveguide 1020 and blade 1008 to pivot away from the shaft cam feature 1070 about the pivot point 1014. In various embodiments, the shaft body 1004 may define additional shaft cam features (not shown). The shaft body 1004 may be rotated in any suitable manner. For example, in manual or hand-operated surgical instruments, the shaft body 1004 may be rotated in a manner similar to that described above with respect to the distal rotation assembly 13 and shaft assembly 14. In robotic surgical instruments, for example, the shaft body 1004 may be rotated in a manner similar to those described above with respect to FIGS. 32-46C. Also, FIG. 60 illustrates another embodiment for rotating the shaft body 1004, for example, in a robotic setting. For example, a proximal end of the shaft body 1004 may comprise first and second spools 1085, 1087. Additional spools 1081, 1083 are positioned to be rotated by a robot (e.g., the spools 1081, 1083 may be coupled to rotatable bodies 612, as described herein. A cable 1093 may be wound around spools 1085 and 1081. Similarly, a cable 1091 may be wound around spools 1083, 1087. Rotation of spool 1081 may cause the cable 1093 to wind off of the spool 1085 to the spool 1081, thereby rotating the shaft body 1004 in a first direction. The shaft rotation in the first direction may also cause cable 1091 to wind off of spool 1083 and onto spool 1087. In some embodiments, spool 1083 may be separately driven to facilitate this winding. To rotate the shaft body 1004 in a direction opposite the first direction, the spool 1083 may be rotated in an opposite direction, causing cable 1091 to wind from the spool 1087 to the spool 1093. At the same time, spool 1085 may draw cable 1093 from spool 1081. Again, spool 1081 may be separated driven to facilitate this winding.

Figure 62:
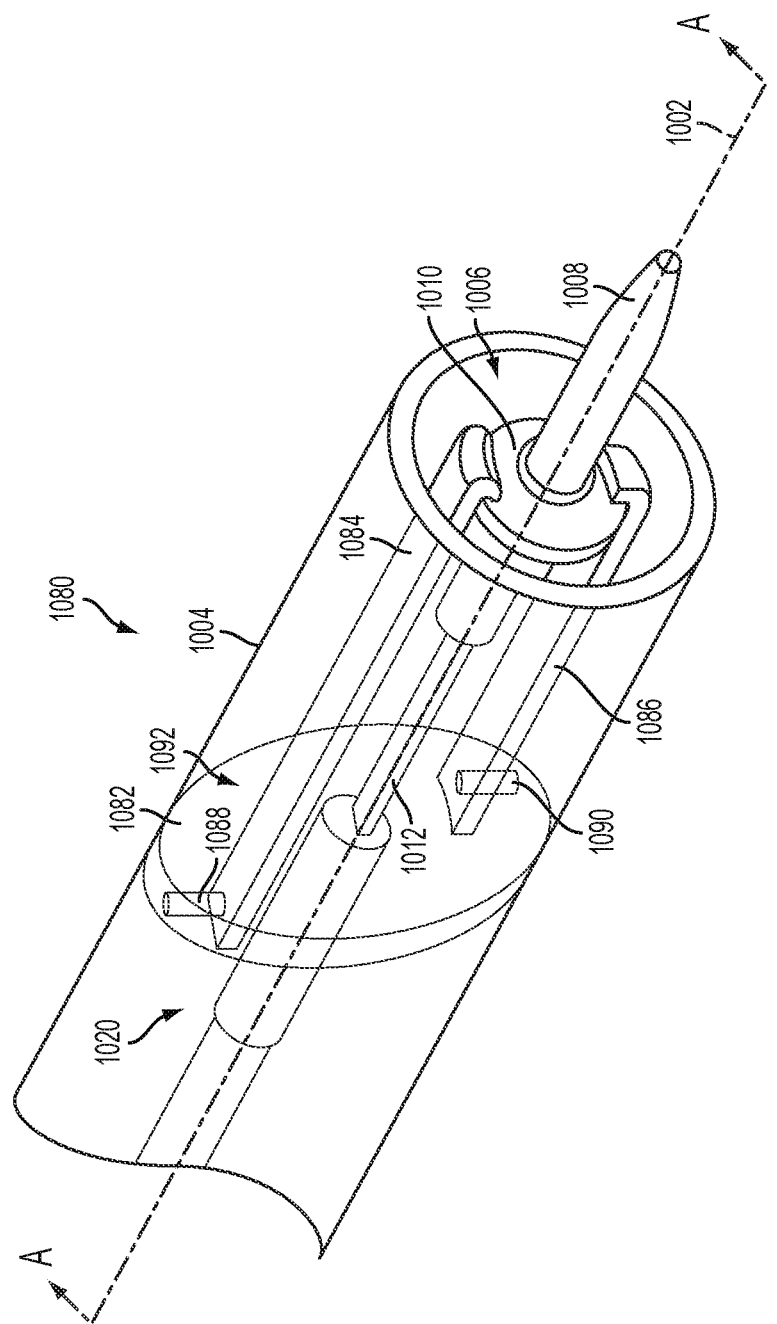
FIG. 62-64 illustrates one embodiment of an articulating shaft that may be utilized with various surgical instruments, including those described herein.
Figure 63:
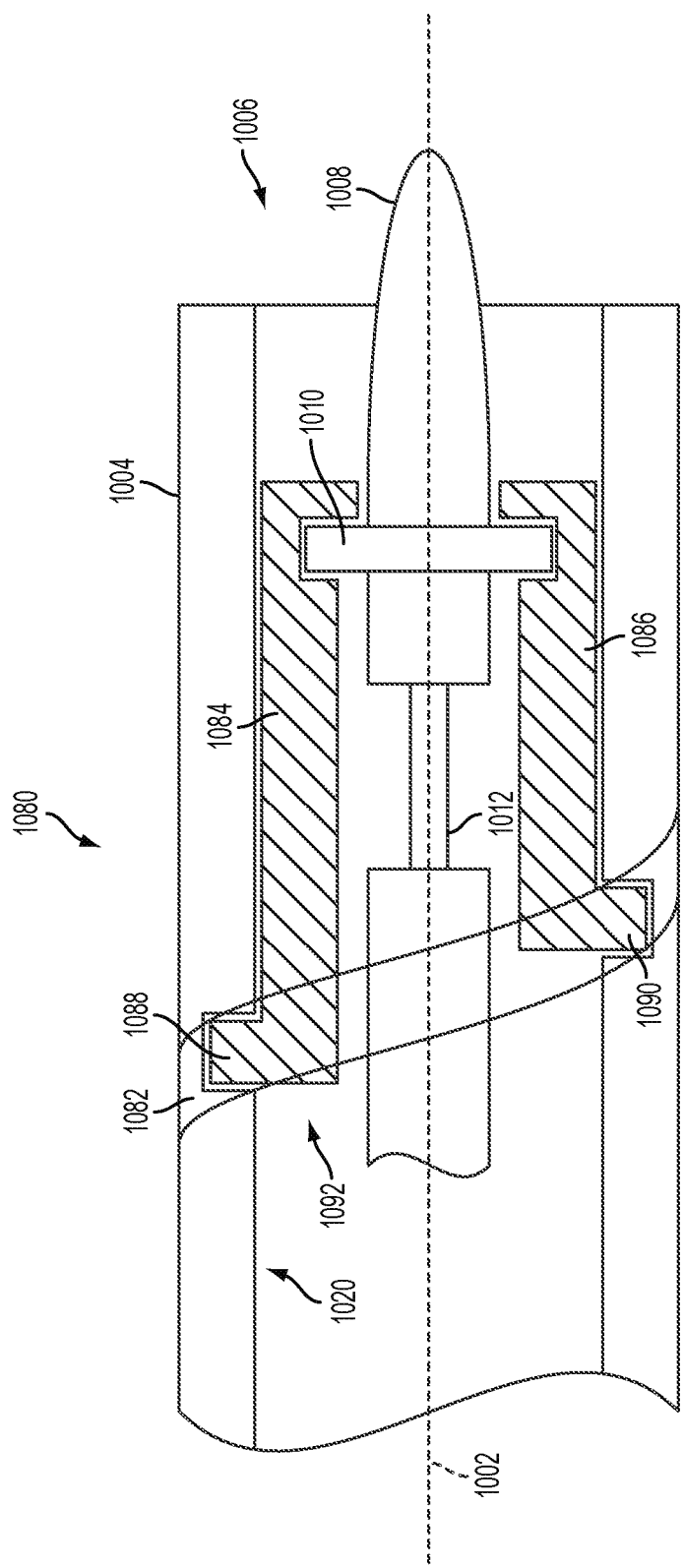
Figure 64:
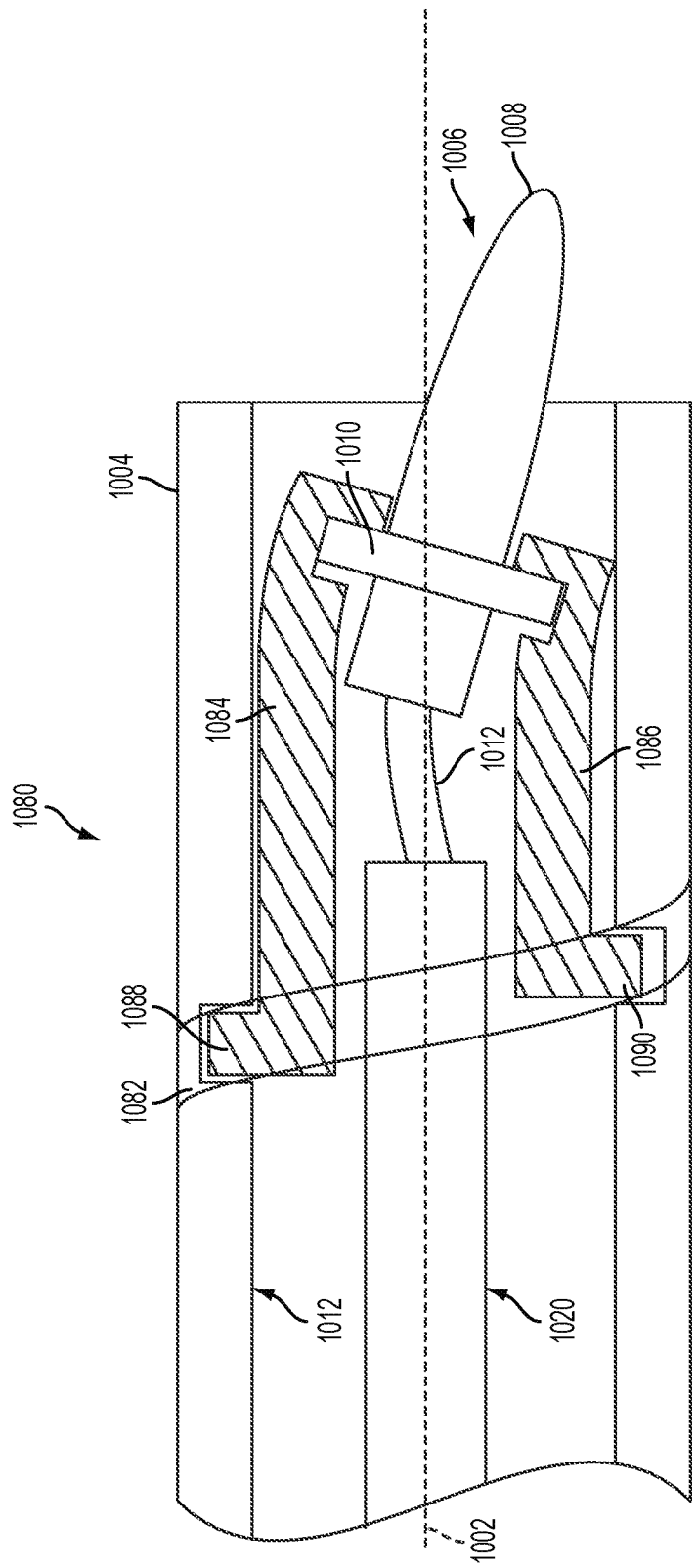

FIG. 62-64 illustrates one embodiment of an articulating shaft 1080 that may be utilized with various surgical instruments, including those described herein. The shaft body 1004 comprises an interior wall 1092 defining a groove 1082. The groove 1082 may have different portions positioned at different axial distances from the end effector 1006. For example, in some example embodiments, the groove 1082 may be an ovaloid. Also, in some example embodiments, as illustrated by FIGS. 62-64, the groove 1082 may represent a partial or complete cross-section of the shaft body 1004 taken in a plane that intersects the longitudinal axis 1002, but is not perpendicular to the axis 1002.

The flange 1010 of the waveguide 1020 (and/or end effector 1006) may be coupled to a pair of interface members 1084, 1086 at a coupling point (represented in FIGS. 62-64 as the flange 1010). A first interface member 1084 may extend proximally from the flange 1010 and may comprise and/or define a first peg member 1088 positioned to ride within the groove 1082. A second interface member 1084 may extend proximally from the flange 1010 and, similarly, may comprise and/or define a second peg member 1090 also positioned to ride within the groove 1082. As illustrated, the length of the first interface member 1084 between the flange 1010 and the first peg 1088 is longer than the length of the second interface member 1086 between the flange 1010 and the second peg 1090, although this is not necessary.

In the example embodiment shown in FIGS. 62-64, the end effector 1006 is pivoted away from the longitudinal axis 1002 by rotating the shaft body 1004 relative to the waveguide 1020, blade 1008 and interface members 1084, 1086. This relative rotation be brought about by rotation of the shaft body 1004, rotation of the waveguide 1020, or both. As the relative rotation takes place, the peg members 1088, 1090 may ride within the groove 1082. As the peg members 1088, 1090 ride within portions of the groove that are closer to and further from the end effector 1006, the peg members 1088, 1090 may be pushed close to and further from the end effector 1006. Differential axial translation of the peg members 1088, 1090 may cause bending of the interface members 1084, 1086, resulting in pivoting of the end effector 1006. For example, as illustrated in FIG. 64, the peg members 1088, 1090 are placed at a position roughly equidistant from the end effector 1006. As the interface member 1084 is longer than the interface member 1086 in the example of FIG. 64, member 1084 may be pushed distally, while member 1086 is pulled proximally. This may result in the pivoting of the end effector 1006 away from the longitudinal axis 1002 as shown.

The shaft body 1004 and/or waveguide 1020 may be rotated in any suitable manner. For example, in manual or hand-operated surgical instruments, the shaft body 1004 and/or waveguide 1020 may be rotated in a manner similar to that described above with respect to the distal rotation assembly 13 and shaft assembly 14. In robotic surgical instruments, for example, the shaft body 1004 and/or waveguide 1020 may be rotated in a manner similar to those described above with respect to FIGS. 32-46C.

Figure 65:
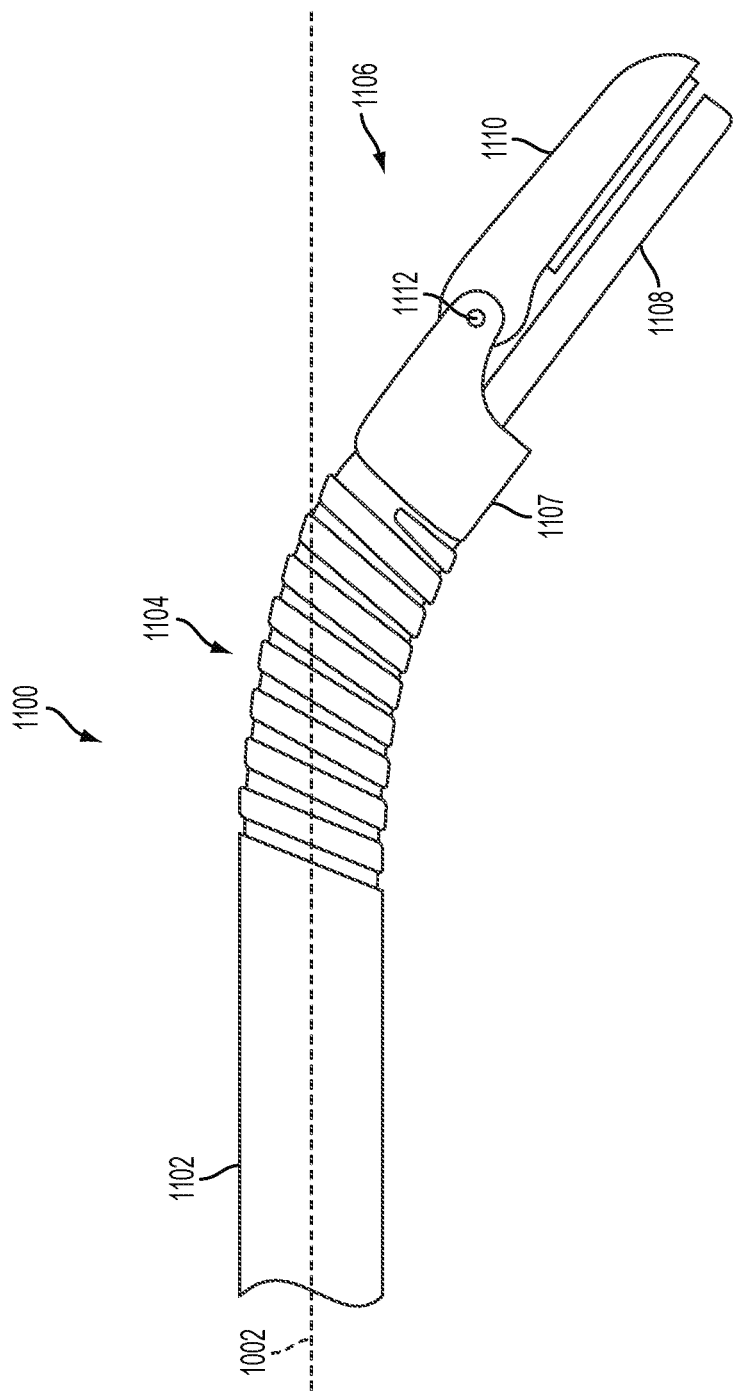
FIGS. 65-67 illustrate one example embodiment of a shaft coupled to an end effector comprising an ultrasonic blade and a pivotable clamp arm.
Figure 66:
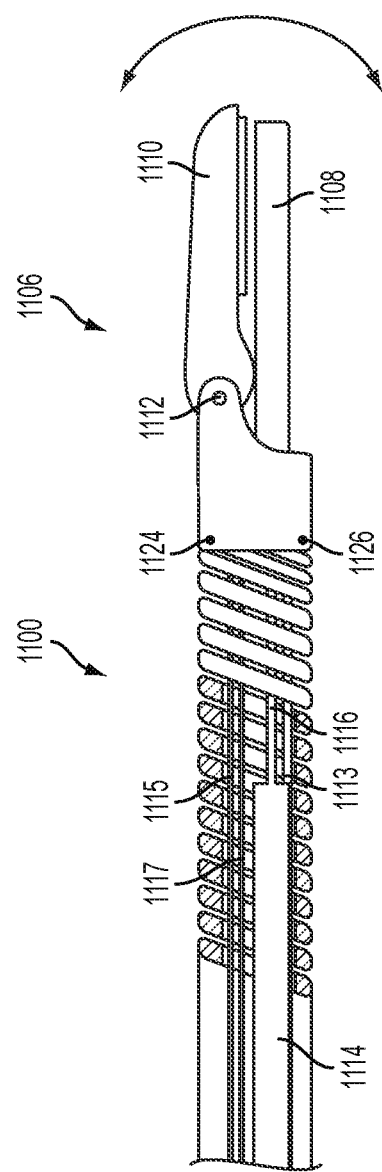
Figure 67:
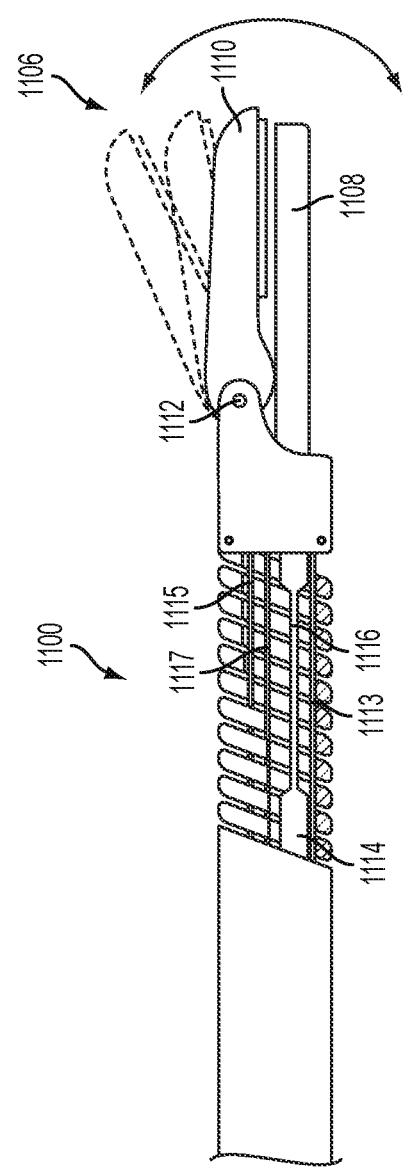

FIGS. 65-67 illustrate one example embodiment of a shaft 1100 coupled to an end effector 1106 comprising an ultrasonic blade 1108 and a pivotable clamp arm 1110. The shaft 11102 comprises a proximal tube 1102 and a flexible portion 1104 with the end effector 1106 coupled to the flexible portion 1104. A clamp arm 1110 is pivotably coupled to the end effector 1106 (e.g., an end effector member 1107) at pivot point 1112. FIGS. 66-67 are cut-away views showing components positioned inside of the shaft 1100. For example, a waveguide 1114 may be acoustically coupled to the ultrasonic blade 1108 and may comprise a bendable portion 1116 at about the position of the flexible portion 1104 of the shaft 1100. Articulation translating members 1113, 1115 may be coupled to the end effector member 1107 at points 1126 and 1124, respectively, to bring about articulation of the end effector 1106, as described below. A clamp arm member 1117 may be coupled to the clamp arm 1110 and may translate distally and proximally to open and close the clamp arm 1110, as described herein below.

Figure 68:
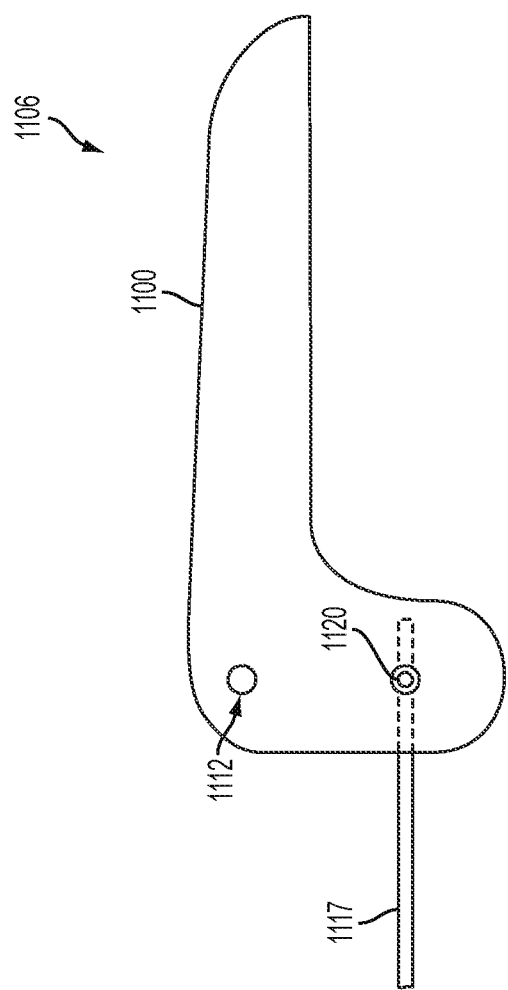
FIG. 68 illustrates one embodiment of the end effector of FIGS. 65-67 illustrating a first way to utilize the clamp arm member to open and close the clamp arm.

FIG. 68 illustrates one embodiment of the end effector 1106 illustrating a first way to utilize the clamp arm member 1117 to open and close the clamp arm 1110. As described above, the clamp arm 1110 may be pivotably coupled to the end effector member 1107 at pivot point 1112. In the example embodiments shown in FIG. 68, the clamp arm member 1117 is a translating member that is coupled to the clamp arm 1110 at 1120. Distal translation of the clamp arm member 1117 may push the point 1120 of the clamp arm 1110 distally, causing the clamp arm 1110 to pivot about the pivot point 1112 to an open position (as illustrated by the dotted lines in FIG. 67). Alternately, pulling the clamp arm member 1117 proximally may pull the point 1120 proximally, causing the clamp arm 1110 to pivot back to the closed position shown in FIGS. 65-66 and 68. The translating clamp arm member 1117 may be translated distally and proximally in any suitable manner. For example, when the shaft 1100 is used in conjunction with a manual or hand held surgical instrument, the translating member 1117 may be translated distally and proximally in a manner similar to that described herein above with respect to the reciprocating tubular actuating member 58 of the instrument 10 and/or the axially moving member 378 of the instrument 300. Also, for example, when the shaft 1100 is used in conjunction with a surgical robot, the translating member 1117 may be translated distally and proximally in a manner similar to that described above with respect to the tissue cutting element 555 of the instrument 310.

Figure 69:
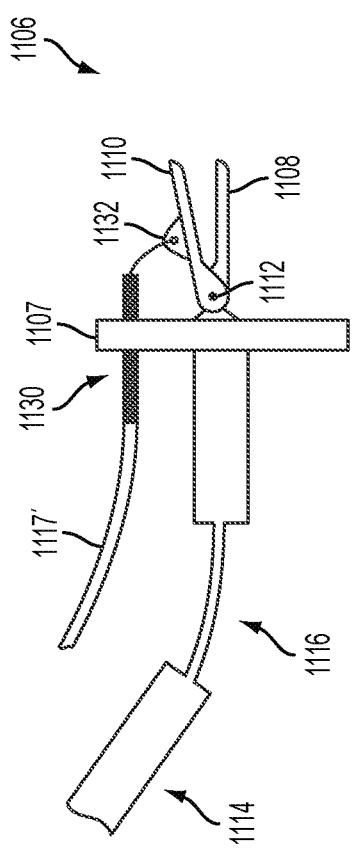
FIGS. 69-70 illustrate another example embodiment of the end effector of FIGS. 65-67 illustrating an additional way to utilize the clamp arm member to open and close the clamp arm.
Figure 70:
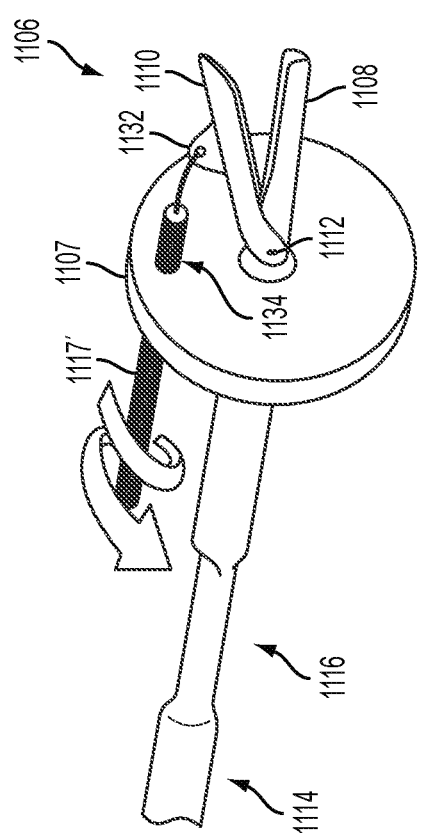

FIGS. 69-70 illustrate another example embodiment of the end effector 1106 illustrating an additional way to utilize a clamp arm member 1117' to open and close the clamp arm 1110. The clamp arm member 1117' may be a flexible, threaded cable defining a threaded portion 1130 that may extend through a threaded hole 1134 of the end effector member 1107. A distal portion of the clamp arm member 1117' may be coupled to a mount 1132 positioned distally from the pivot point 1112. As the clamp arm member 1117' is rotated in a first direction, it may translate distally, pushing distally on the mount 1132 and clamp arm 1110 and tending to close the clamp arm 1110. As the clamp arm member 1117' is rotated in a second direction opposite the first direction, it may translate proximally, pulling proximally on the mount 1132 and tending to open the clamp arm 1110. The clamp arm member 1117' may be rotated in any suitable manner. For example, in manual or hand-operated surgical instruments, the clamp arm member 1117' may be rotated in a manner similar to that described above with respect to the distal rotation assembly 13 and shaft assembly 14. In robotic surgical instruments, for example, the clamp arm member 1117' may be rotated in a manner similar to those described above with respect to FIGS. 32-46C.

Referring now again to FIGS. 65-67, it will be appreciated that articulation of the end effector 1106 may be brought about in any suitable manner. For example, when the translating member 1113 is pulled proximally, the end effector 1106 may pivot toward the translating member 1113 as shown in FIG. 65. Conversely, when the translating member 1115 is pulled proximally, the end effector 1106 may pivot towards the translating member 1115.

Figure 71:
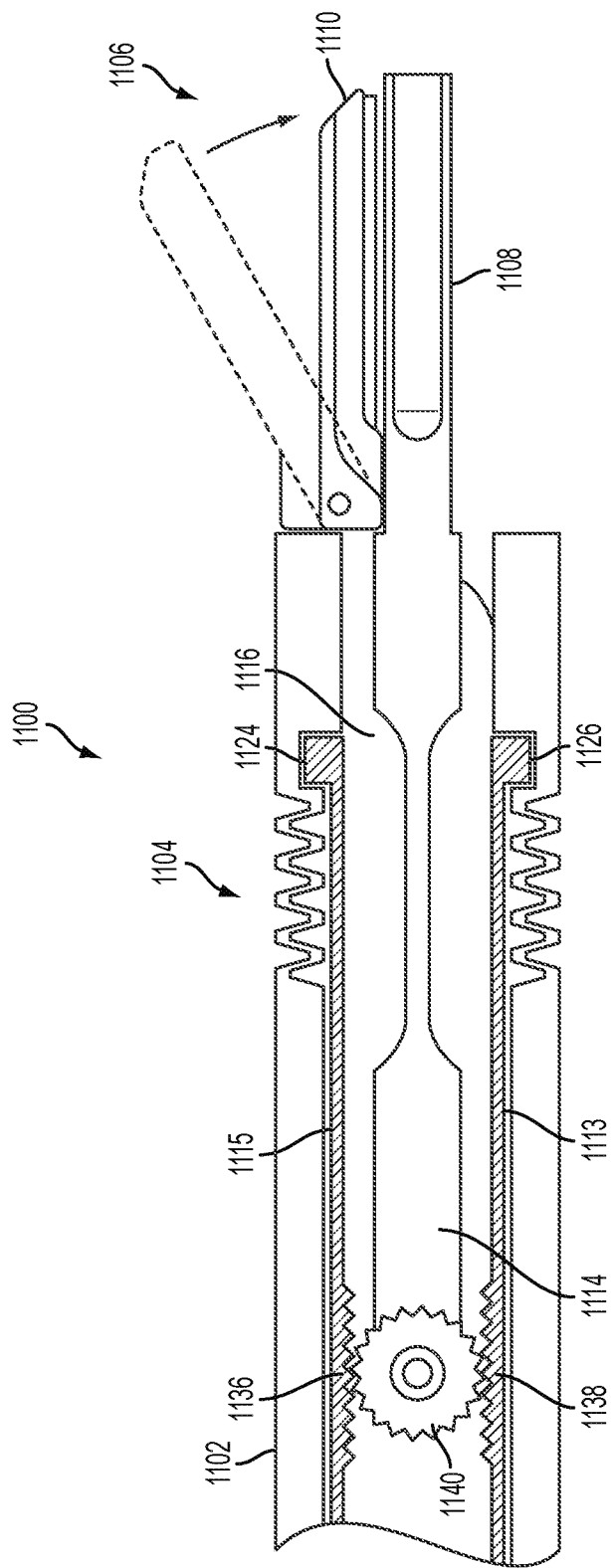
FIGS. 71-72 illustrate one example embodiment of the shaft of FIGS. 65-67 showing an example mechanism for managing differential translation of the translating members.
Figure 72:
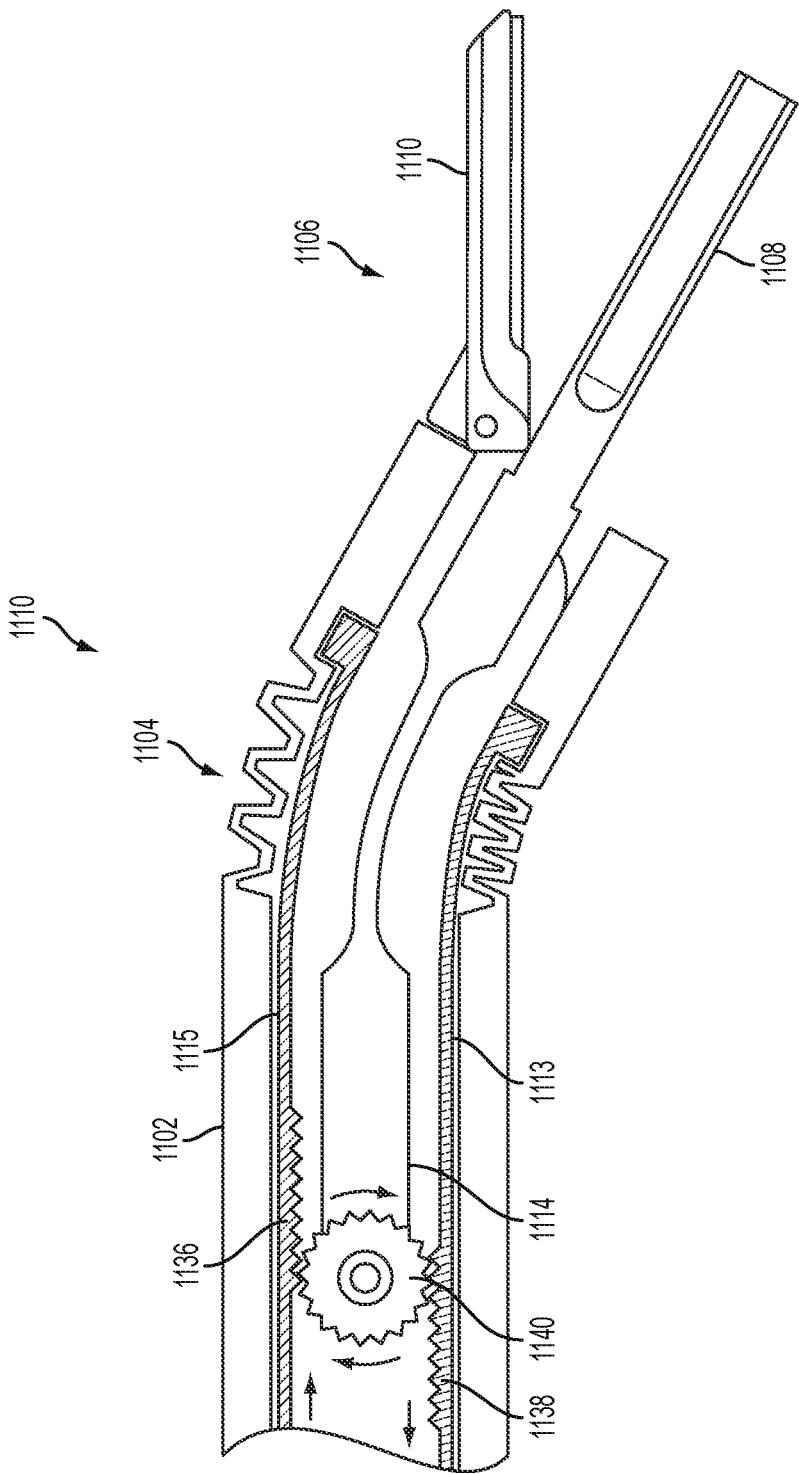

FIGS. 71-72 illustrate one example embodiment of the shaft 1110 showing an example mechanism for managing differential translation of the translating members 1113, 1115. As shown in FIGS. 71-72, the translating members may comprise and/or define respective rack gears 1138, 1136. A pinion gear 1140 may be positioned to engage both of the rack gears 1138, 1136. When one of the translating members 1113 is translated along the longitudinal axis, rack gear 1138 may interface with the pinion gear 1140 causing corresponding and oppositely-directed translation of the opposite translating member 1115, and visa versa. This may facilitate differential translation of the members 1113, 1115. In some embodiments, the pinion gear 1140 may be driven, either manually via a lever and/or automatically (e.g., by a robotic surgical device). When the pinion gear 1140 is driven, it may, in turn, drive rack gears 1138, 1136 causing differential proximal and distal translation of the translating members 1113, 1115 and articulation of the end effector 1106.

Figure 73:
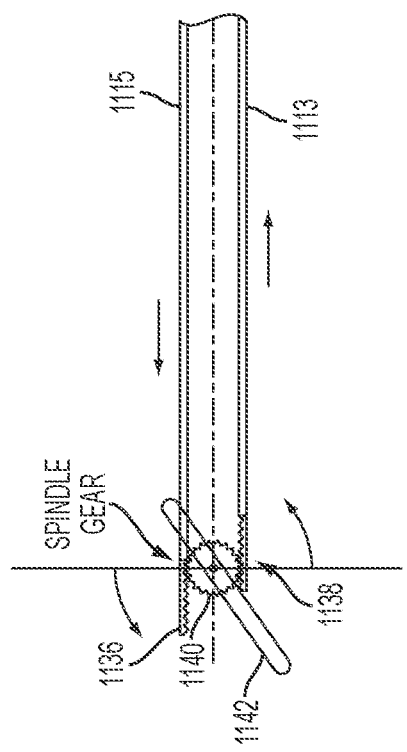
FIGS. 73-74 illustrate one embodiment of a hand-held surgical instrument utilizing the shaft of FIGS. 65-67 in the configuration shown in FIGS. 71-72.
Figure 74:
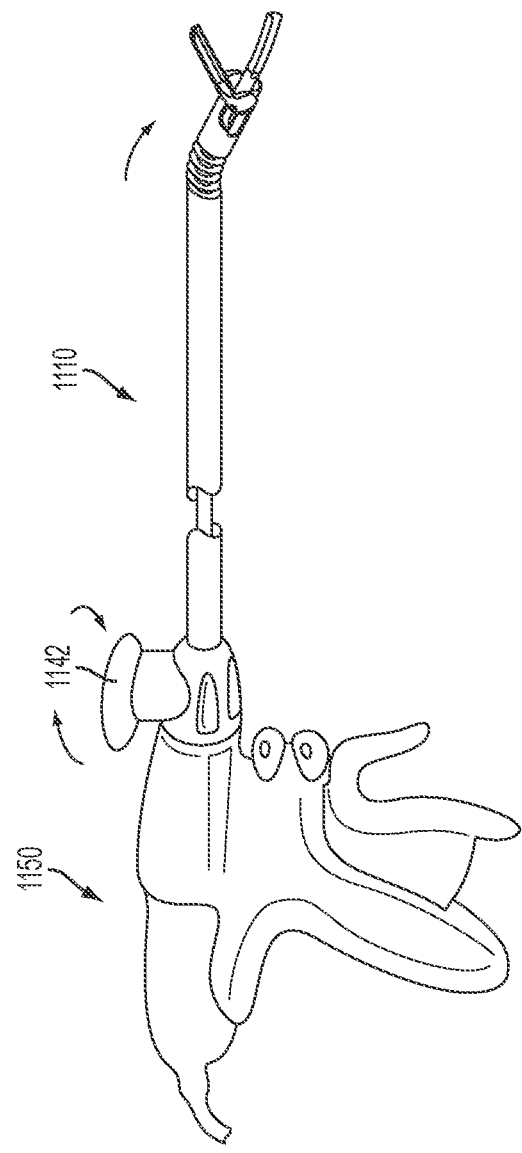

Differential translation of the translating members 1113, 1115 may be accomplished in any suitable manner. For example, when the shaft 1100 is utilized in the context of a surgical robot, the members 1170, 1172 may be differentially translated utilizing any of the methods and/or mechanisms described herein above with respect to FIGS. 32-46C. Alternatively, FIGS. 73-74 illustrate one embodiment of a hand-held surgical instrument utilizing the shaft 1100 in the configuration shown in FIGS. 71-72. Pinion gear 1140 is shown in FIG. 73 as coupled to a lever 1142 that may be rotated by a clinician to bring about articulation of the end effector 1106, as described herein above. FIG. 74 shows the instrument 1150 including the lever 1142, demonstrating placement and use of the lever 1142 to bring about articulation.

Figure 75:
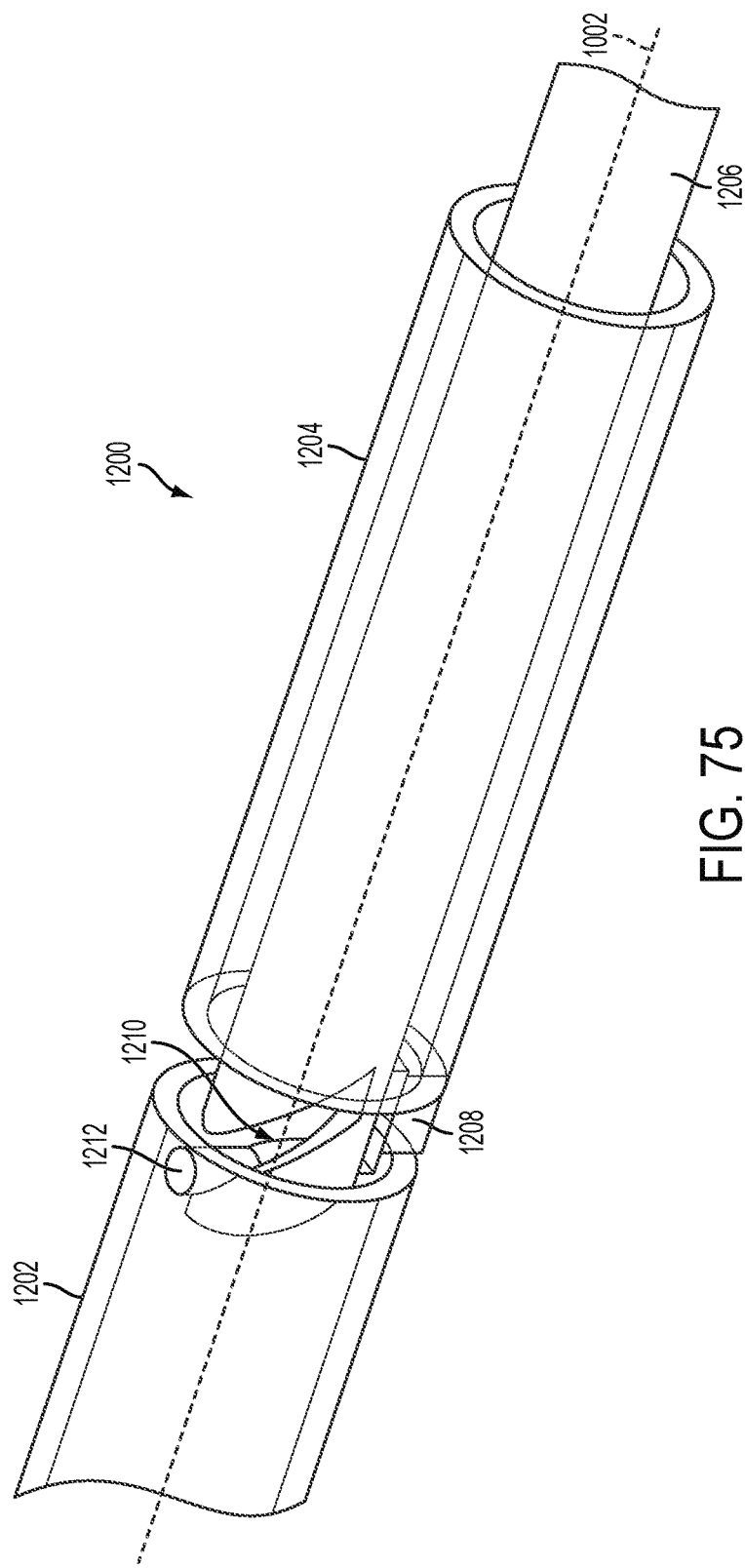
FIGS. 75-76 illustrate one embodiment of an articulating shaft that may be utilized with various surgical instruments, including those described herein.
Figure 76:
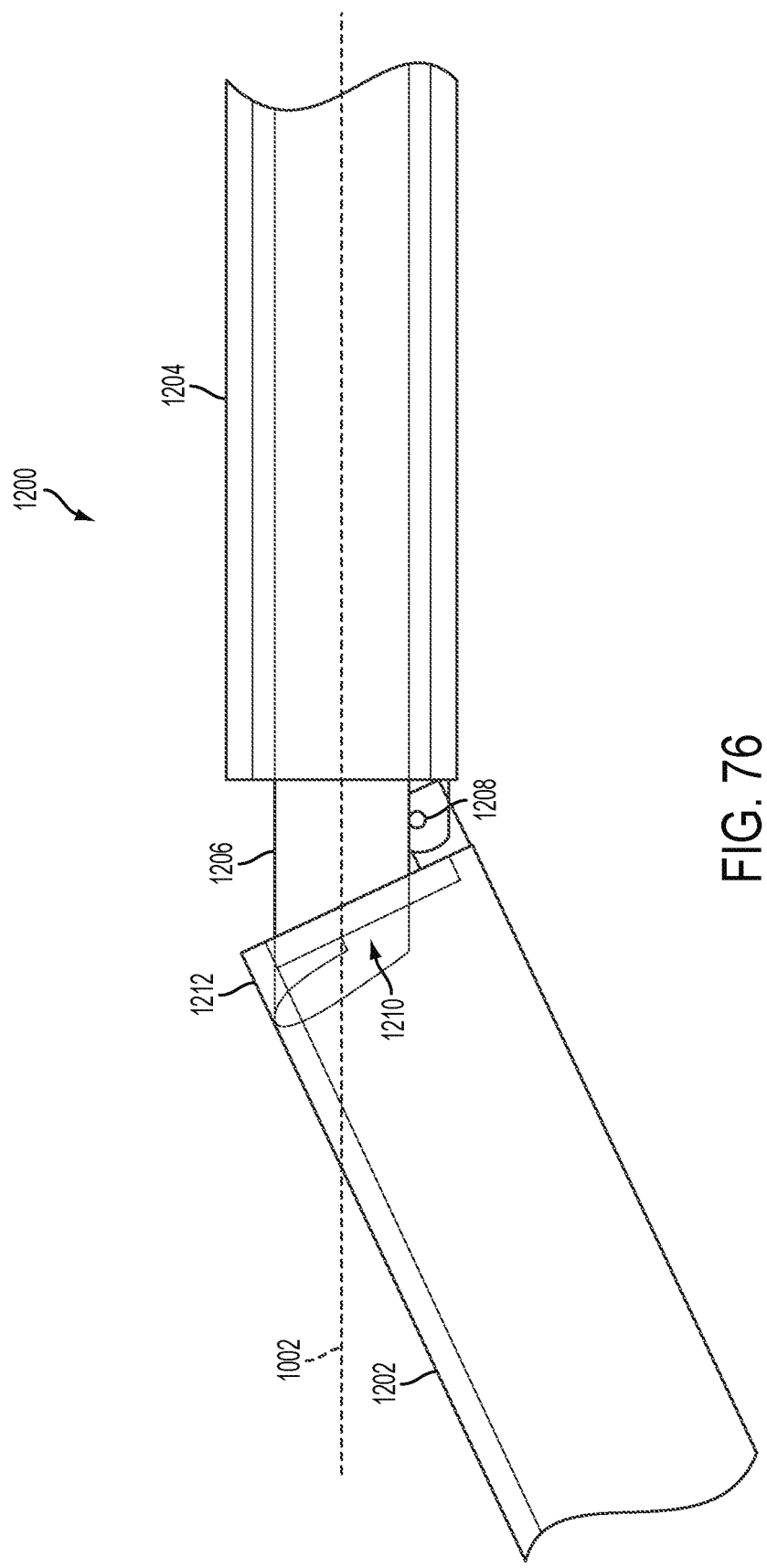

FIGS. 75-76 illustrate one embodiment of an articulating shaft 1200 that may be utilized with various surgical instruments, including those described herein. The shaft 1200 comprises a distal tube 1202 pivotably coupled to a proximal tube 1204 via a hinge interface 1208. The hinge interface 1208 may be and/or comprise any suitable type of hinge and may, in some example embodiments, comprise a pin. An inner rotatable member 1206 may extend proximally through the proximal tube 1204 and at least a portion of the distal tube 1202. The inner rotatable member 1206 may define a slanted slot 1210. The distal tube 1202 may comprise a peg 1212 positioned to ride within the slanted slot 1210.

The peg 1212, as illustrated, may be positioned opposite the longitudinal axis 1002 from the hinge interface 1208. Due to the slant of the slot 1210, rotation of the inner rotatable member 1206 and slot 1210 in a first direction may tend to push the peg 1212, and thereby the distal tube 1202, distally. Rotation of the inner rotatable member 1206 and slot 1210 in a second direction opposite the first direction may tend to pull the peg 1212 and distal tube 1202 proximally. When the peg 1212 and distal tube 1202 are pushed distally by rotation of the member 1206 and slot 1210, the distal tube 1202 may pivot about the hinge interface 1208 away from the longitudinal axis 1002, as illustrated in FIG. 76. When the peg 1212 and distal tube 1202 are pulled proximally by rotation of the member 1206 and slot 1210, the distal tube 1202 may pivot back towards the longitudinal axis 1002 to the position illustrated in FIG. 75. Rotation of the rotatable member 1206 may be actuated in any suitable manner. For example, in manual or hand-operated surgical instruments, the member 1206 may be rotated in a manner similar to that described above with respect to the distal rotation assembly 13 and shaft assembly 14. In robotic surgical instruments, for example, the member 1206 may be rotated in a manner similar to those described above with respect to FIGS. 32-46C. It will be appreciated that the shaft 1200 may be used with any suitable type of surgical instrument including, for example, an ultrasonic surgical instrument, an electrosurgical instrument, etc. In some embodiments, wire, waveguides and/or other control devices for a surgical instrument may pass through the proximal and distal tubes 1204, 1202. For example, in some embodiments, a waveguide extending through the proximal and distal tubes 1204, 1202 may have a bendable portion 1046, for example, similar to the bendable portions 1506, 1530, 1576, etc., described herein above. The bendable portion may be positioned at about the hinge interface 1208 so as to bend as the distal tube 1202 pivots.

Figure 77:
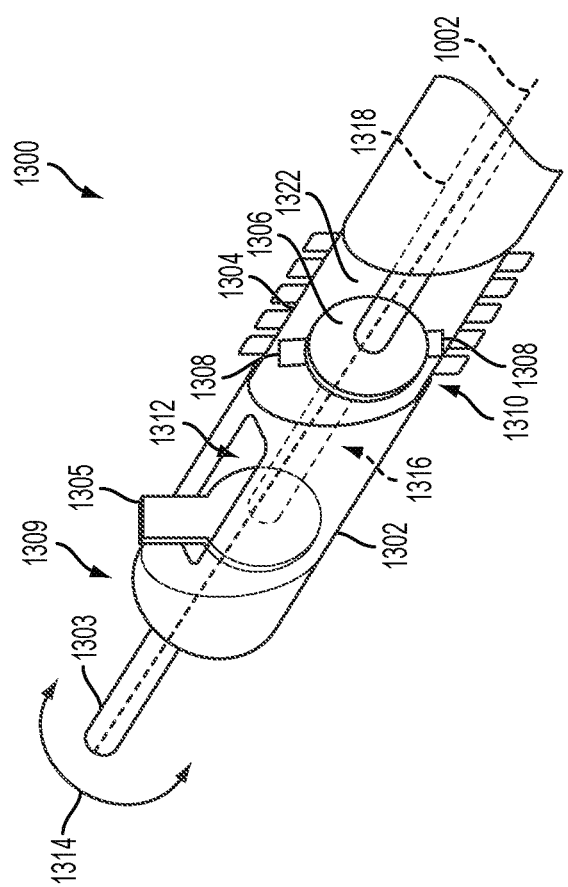
FIG. 77 illustrates one embodiment of a shaft that may be utilized with various surgical instruments, including those described herein.

FIG. 77 illustrates one embodiment of a shaft 1300 that may be utilized with various surgical instruments, including those described herein. An end effector 1309 is positioned within an inner shaft 1322 and an outer shaft 1302. The end effector 1309 comprises an ultrasonic blade 1303. Moving proximally, the blade 1303 is acoustically coupled to a flange 1305 that extends through a slot 1312 in the outer shaft 1302. The flange 1305 is coupled to a second flange 1306 via a bendable waveguide portion 1316 (e.g., similar to the bendable portions 1506, 1530, 1576 described herein above). The second flange 1306 may be fixedly coupled to the inner shaft 1322 via supports 1308. The second flange 1306 and supports 1308 may form pivot point 1304. The outer shaft 1302 defines a slot 1312 that receives the flange 1305. When the outer shaft 1302 is translated distally relative to the inner shaft 1322, the flange 1305 may reach a proximal-most portion of the slot 1312, causing the blade 1303 to pivot about the pivot point 1304. The blade 1303 may return to its rest position when the outer shaft 1302 is pulled proximally again. In various embodiments, the respective flanges 1306, 1305 may be positioned at nodes of the waveguide 1308 at the resonant wavelength of the system. In some embodiments, the flanges 1306, 1305 are separated by a single resonant wavelength.

Figure 78:
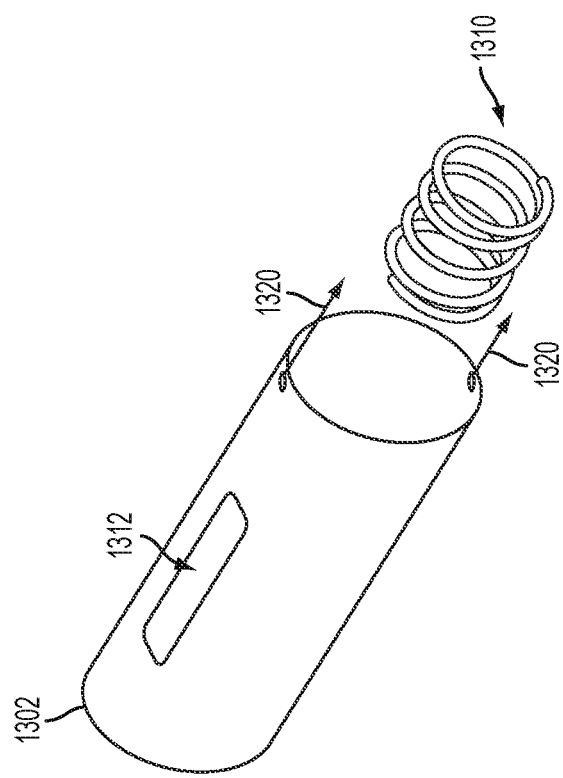
FIG. 78 illustrates a view showing additional details of one embodiment of an outer shaft shown in FIG. 77.

The outer shaft 1302 may be translated distally and proximally in any suitable manner. FIG. 78 illustrates a view showing additional details of one embodiment of the outer shaft 1302. In certain embodiments, the outer shaft 1302 biased distally by a spring 1310. Reciprocating control members 1320 may be utilized to pull the outer shaft 1302 proximally, overcoming the bias of the spring 1310. When tension on the control members 1320 is released, the spring 1310 may bias the outer shaft distally, causing articulation as described above. The control members 1320 may be translated distally and proximally in any suitable manner. For example, when the shaft 1200 is used in conjunction with a manual or hand held surgical instrument, the control members 1320 may be translated distally and proximally in a manner similar to that described herein above with respect to the reciprocating tubular actuating member 58 of the instrument 10 and/or the axially moving member 378 of the instrument 300. Also, for example, when the shaft 1300 is used in conjunction with a surgical robot, the control members 1320 may be translated distally and proximally in a manner similar to that described above with respect to the tissue cutting element 555 of the instrument 310. In certain embodiments, however, the spring 1310 may be omitted. For example, both proximal and distal force may be provided to the outer shaft 1302 by the reciprocating control members.

Figure 79:
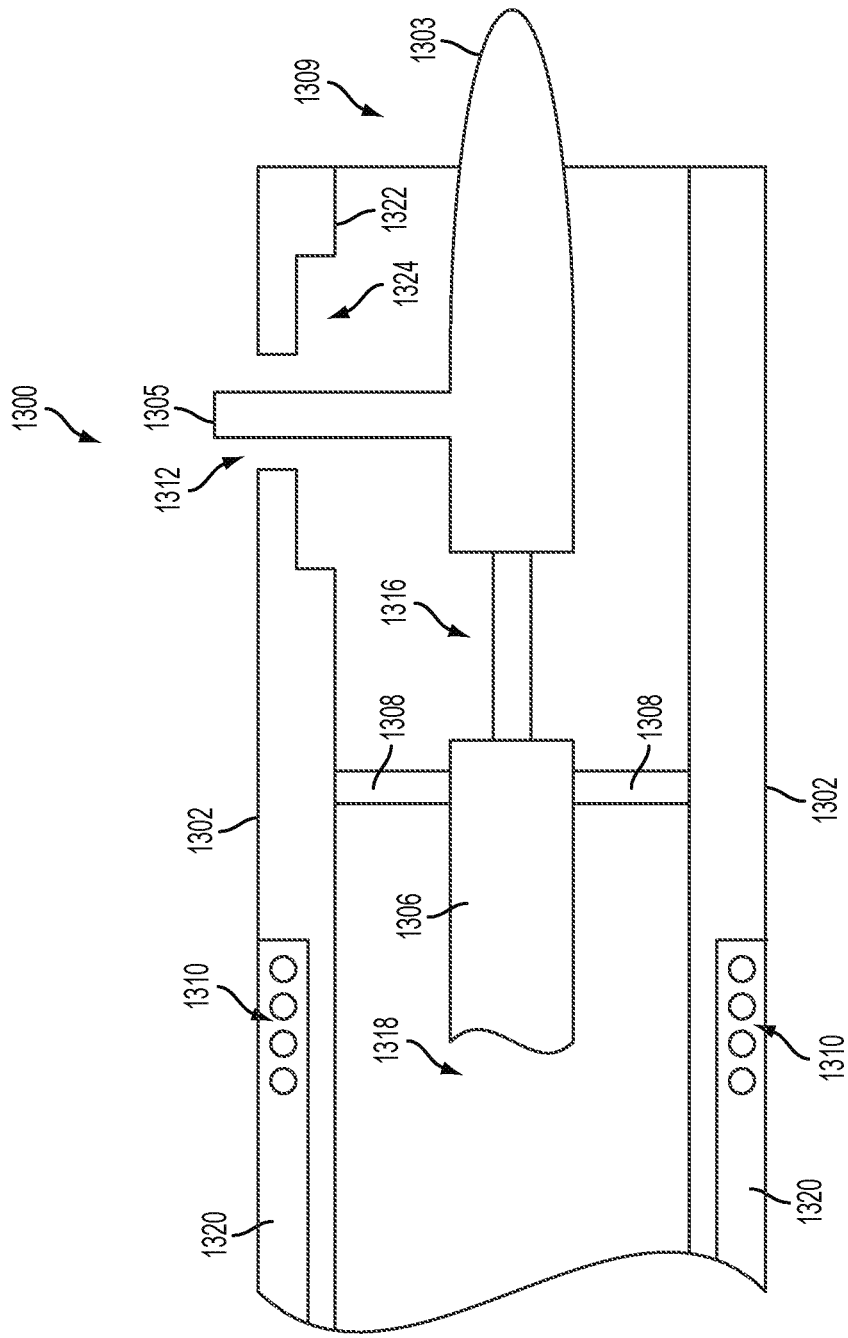
FIG. 79 illustrates a cut-away view of one embodiment of the shaft shown in FIG. 77.
Figure 80:
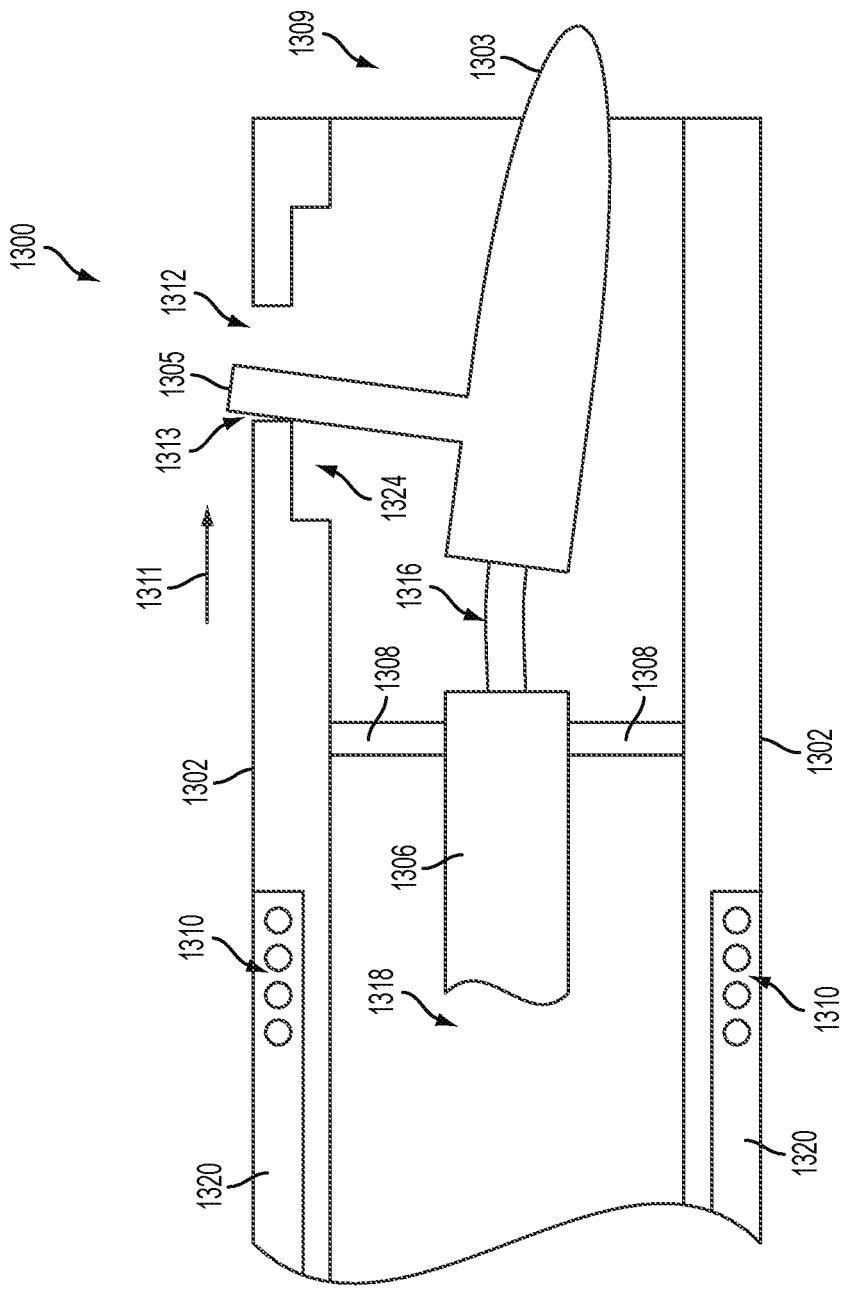
FIG. 80 illustrates the cut-away view of one embodiment of the shaft of FIG. 79, with the outer shaft extended distally to articulate the blade.

FIG. 79 illustrates a cut-away view of one embodiment of the shaft 1300. FIG. 79 shows additional features of the inner shaft 1322. For example, the inner shaft 1322 may define a slot 1324 which may also receive the flange 1305. The slot 1324 may have an area larger than that of the slot 1312. For example, the flange 1305 may not contact the edges of the slot 1324 during normal operation. FIG. 80 illustrates the cut-away view of one embodiment of the shaft 1300, with the outer shaft 1302 extended distally to articulate the blade 1303. As illustrated, a distal edge 1313 of the slot 1312 contacts the flange 1305 pushing it distally in the direction of arrow 1311. This, in turn, causes the blade 1303 and flange 1305 to pivot (at bendable waveguide portion 1316) to the position shown.

Figure 81:
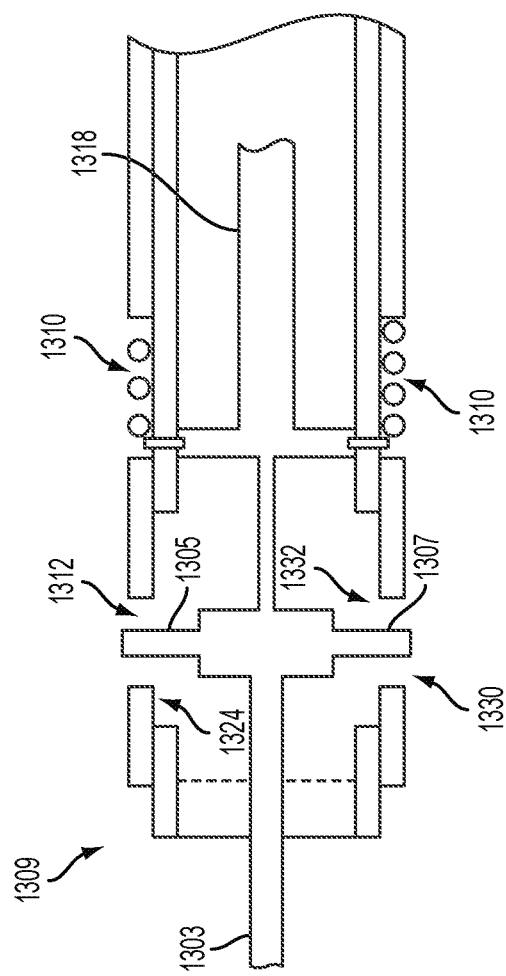
FIG. 81 illustrates one embodiment of the shaft of FIG. 77 having an additional distal flange.

FIG. 81 illustrates one embodiment of the shaft 1300 having an additional distal flange 1307. The flange 1307 may extend substantially opposite the flange 1305. To prevent interference with articulation, the outer and inner shafts 1302, 1322 may define additional slots 1330, 1332 of a size sufficient such that the flange 1307 does not contact any edges of the slots 1330, 1332 during articulation. Also, although articulation in the described embodiment is provided by distal and proximal translation of the outer shaft 1302, it will be appreciated that similar shafts may be constructed having a reciprocating inner slotted shaft to perform the function provided by the outer shaft 1302 as described herein. For example, the inner shaft may be translatable within an outer shaft and may define a slot for receiving the flange 1305. As the inner shaft translates distally, its slot may contact the flange 1305, causing the blade 1303 to articulate, as shown in FIG. 80.

Non-Limiting Examples

Various embodiments are directed to articulatable surgical instruments comprising an end effector comprising an ultrasonic blade, a hollow shaft extending proximally from the end effector along a longitudinal axis and a waveguide extending through the shaft and acoustically coupled to the ultrasonic blade. In certain embodiments, the waveguide comprises a distally positioned flange positioned within the hollow shaft proximally from the blade. The waveguide may also be held stationary at a first pivot point positioned within the hollow shaft proximally from the flange. A reciprocating wedge may be positioned within the hollow shaft such that distal motion of the wedge pushes the wedge between the flange and the hollow shaft, causing the ultrasonic blade to pivot about the first pivot in a first direction.

In certain embodiments, the hollow shaft may comprise a first shaft defining a slot and a second shaft. The first and second shafts may be translatable relative to one another along the longitudinal axis. The waveguide may comprise a distally positioned first flange positioned within the hollow shaft proximally from the blade, a bendable portion positioned proximally from the first flange, and a second flange positioned proximally from the bendable portion and fixedly coupled to the second shaft. The first flange may extend through the slot. Also, the first shaft may be translatable from a distal position where a proximal edge of the slot pushes the first flange distally, bending the ultrasonic blade away from the longitudinal axis to a proximal position.

In certain embodiments, an interior portion of the hollow shaft defines a shaft cam feature directed towards the longitudinal axis. Further, the waveguide may define a waveguide cam feature directed away from the longitudinal axis. In this way, rotation of the hollow shaft relative to the waveguide causes the shaft cam feature to come into contact with the waveguide cam feature, resulting in bending of the waveguide and ultrasonic blade away from the longitudinal axis about the first pivot point in a first direction. In certain embodiments, the end effector comprises a clamp arm coupled to a member positioned around the ultrasonic blade. The clamp arm may be pivotably coupled to the member at a pivot point. A flexible control cable may be coupled to the clamp arm at a point offset from the pivot point. Distal and proximal translation of the control cable may cause the clamp arm to pivot relative to the ultrasonic blade. In certain embodiments, the member may define a threaded hole through which extends a flexible, threaded cable. The cable may also be coupled to the clamp arm such that rotation of the cable causes it to translate proximally and distally, depending on the direction of rotation. Such proximally and distal translation may cause the clamp arm to open and close.

Also, various embodiments are directed to articulatable surgical instruments comprising an end effector comprising an ultrasonic blade and a hollow shaft extending proximally from the end effector. An interior wall of the hollow shaft may define a groove, where different positions of the groove are positioned at different axial distances from the end effector. A first interface member may be coupled to either a waveguide or the ultrasonic blade at a coupling point and extending proximally. The first interface member may comprise a first peg member positioned within the groove. A second interface member may be coupled to the waveguide or the ultrasonic blade at the coupling point and may extend proximally. The second interface member may also comprise a peg member positioned within the groove. Upon rotation of the hollow shaft relative to the waveguide, the first and second peg members may translate within the groove causing bending of the first and second interface members and deflection of the first and second interface members away from the longitudinal axis.

Various embodiments are directed to articulatable surgical instruments comprising an end effector and a shaft extending proximally from the end effector along a longitudinal axis. The shaft may comprise a proximal tube and a distal tube pivotably coupled to the proximal tube at a hinge interface offset from the longitudinal axis. The distal tube may comprise an axially directed peg member. The surgical instruments may further comprise an inner rotatable member extending proximally through at least a portion of the proximal tube and at least a portion of the distal tube. The inner rotatable member may define a slanted slot such that the axially directed peg member rides at least partially within the slanted slot and such that rotation of the inner rotatable member in a first direction pushes the peg member and distal tube distally and rotation of the inner rotatable member in a second direction opposite the first direction pushes the peg member and distal tube proximally.

Applicant also owns the following patent applications that are each incorporated by reference in their respective entireties:

U.S. patent application Ser. No. 13/536,271, filed on Jun. 28, 2012 and entitled "Flexible Drive Member," now U.S. Pat. No. 9,204,879;

U.S. patent application Ser. No. 13/536,288, filed on Jun. 28, 2012 and entitled "Multi-Functional Powered Surgical Device with External Dissection Features," now U.S. Patent Application Publication No. 2014-0005718 A1;

U.S. patent application Ser. No. 13/536,295, filed on Jun. 28, 2012 and entitled "Rotary Actuatable Closure Arrangement for Surgical End Effector," now U.S. Pat. No. 9,119,657;

U.S. patent application Ser. No. 13/536,326, filed on Jun. 28, 2012 and entitled "Surgical End Effectors Having Angled Tissue-Contacting Surfaces," now U.S. Pat. No. 9,289,256;

U.S. patent application Ser. No. 13/536,303, filed on Jun. 28, 2012 and entitled "Interchangeable End Effector Coupling Arrangement," now U.S. Pat. No. 9,028,494;

U.S. patent application Ser. No. 13/536,393, filed on Jun. 28, 2012 and entitled "Surgical End Effector Jaw and Electrode Configurations," now U.S. Patent Application Publication No. 2014-0005640 A1;

U.S. patent application Ser. No. 13/536,362, filed on Jun. 28, 2012 and entitled "Multi-Axis Articulating and Rotating Surgical Tools," now U.S. Pat. No. 9,125,662; and U.S. patent application Ser. No. 13/536,417, filed on Jun. 28, 2012 and entitled "Electrode Connections for Rotary Driven Surgical Tools," now U.S. Pat. No. 9,101,385.

It will be appreciated that the terms "proximal" and "distal" are used throughout the specification with reference to a clinician manipulating one end of an instrument used to treat a patient. The term "proximal" refers to the portion of the instrument closest to the clinician and the term "distal" refers to the portion located furthest from the clinician. It will further be appreciated that for conciseness and clarity, spatial terms such as "vertical," "horizontal," "up," or "down" may be used herein with respect to the illustrated embodiments. However, surgical instruments may be used in many orientations and positions, and these terms are not intended to be limiting or absolute.

Various embodiments of surgical instruments and robotic surgical systems are described herein. It will be understood by those skilled in the art that the various embodiments described herein may be used with the described surgical instruments and robotic surgical systems. The descriptions are provided for example only, and those skilled in the art will understand that the disclosed embodiments are not limited to only the devices disclosed herein, but may be used with any compatible surgical instrument or robotic surgical system.

Reference throughout the specification to "various embodiments," "some embodiments," "one example embodiment," or "an embodiment" means that a particular feature, structure, or characteristic described in connection with the embodiment is included in at least one example embodiment. Thus, appearances of the phrases "in various embodiments," "in some embodiments," "in one example embodiment," or "in an embodiment" in places throughout the specification are not necessarily all referring to the same embodiment. Furthermore, the particular features, structures, or characteristics illustrated or described in connection with one example embodiment may be combined, in whole or in part, with features, structures, or characteristics of one or more other embodiments without limitation.

While various embodiments herein have been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. For example, each of the disclosed embodiments may be employed in endoscopic procedures are, laparoscopic procedures, as well as open procedures, without limitations to its intended use.

It is to be understood that at least some of the figures and descriptions herein have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein.

While several embodiments have been described, it should be apparent, however, that various modifications, alterations and adaptations to those embodiments may occur to persons skilled in the art with the attainment of some or all of the advantages of the disclosure. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosure as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An articulatable surgical instrument comprising:
a hollow outer shaft comprising a first slot and a longitudinal axis;
a hollow inner shaft movable within the hollow outer shaft, wherein the hollow inner shaft comprises a second slot, and wherein the second slot is at least partially aligned with the first slot;
an end effector positioned within the hollow inner shaft, the end effector comprising an ultrasonic blade, wherein the ultrasonic blade comprises a first flange and wherein the first flange extends through the first slot and the second slot;
a waveguide extending through the hollow inner shaft and acoustically coupled to the ultrasonic blade and a second flange, wherein the waveguide comprises a flexible portion, and wherein the second flange is coupled to the hollow inner shaft; and
wherein the hollow outer shaft is configured to translate between a proximal position and a distal position in response to a user input, and wherein the first flange moves between a proximal slot position and a distal slot position and causes the ultrasonic blade to pivot about the longitudinal axis as the hollow outer shaft translates between the proximal position and the distal position.

2. The articulatable surgical instrument of claim 1, further comprising a spring, wherein the spring is configured to bias the hollow outer shaft distally.

3. The articulatable surgical instrument of claim 2, further comprising reciprocating control members configured to create a tension on the spring to translate the hollow outer shaft proximally, wherein the control members are further configured to release the tension on the spring to translate the hollow outer shaft distally.

4. The articulatable surgical instrument of claim 1, wherein the hollow inner shaft and the hollow outer shaft are translatable relative to one another along the longitudinal axis.

5. The articulatable surgical instrument of claim 1, wherein translating the hollow outer shaft from the proximal position to the distal position causes a proximal edge of the first slot to push the first flange distally.

6. The articulatable surgical instrument of claim 1, wherein the hollow inner shaft is configured to translate between an inner proximal position and an inner distal position in response to a user input, and wherein the first flange moves between the proximal slot position to the distal slot position and causes the ultrasonic blade to pivot about the longitudinal axis as the hollow inner shaft translates between the inner proximal position and the inner distal position.

7. The articulatable surgical instrument of claim 6, wherein translating the hollow inner shaft from the inner proximal position to the inner distal position causes a proximal edge of the second slot to push the first flange distally.

8. The articulatable surgical instrument of claim 1, wherein:
the ultrasonic blade further comprises a third flange extending opposite the first flange,
the hollow outer shaft comprises a third slot,
the hollow inner shaft comprises a fourth slot,
the fourth slot is at least partially aligned with the third slot, and
the third flange extends through the third slot and the fourth slot.

9. An articulatable surgical instrument comprising:
a first hollow shaft comprising an opening and a longitudinal axis, wherein the first hollow shaft is configured to translate between a proximal position and a distal position in response to an input;
a second hollow shaft concentric with the first hollow shaft; and an end effector movable within the second hollow shaft, the end effector comprising an ultrasonic blade, wherein the ultrasonic blade comprises a flange extending through the opening, translating the first hollow shaft between the proximal position and the distal position causes movement of the flange, and the movement of the flange causes the ultrasonic blade to pivot about the longitudinal axis, wherein the second hollow shaft is configured to translate between an inner proximal position and an inner distal position in response to a user input to further cause the movement of the flange.

10. The articulatable surgical instrument of claim 9, wherein the second hollow shaft and the first hollow shaft are translatable relative to one another along the longitudinal axis.

11. The articulatable surgical instrument of claim 9, wherein translating the first hollow shaft from the proximal position to the distal position causes a proximal edge of the opening to push the flange distally.

12. The articulatable surgical instrument of claim 9, wherein translating the second hollow shaft from the inner proximal position to the inner distal position causes a proximal edge of the second hollow shaft to push the flange distally.

13. The articulatable surgical instrument of claim 9, wherein:

the flange is a first flange and the opening is a first opening, the ultrasonic blade further comprises a second flange extending opposite the first flange, the first hollow shaft comprises a second opening, and the second flange extends through the second opening.

14. The articulatable surgical instrument of claim 9, further comprising:

a waveguide extending through the second hollow shaft and acoustically coupled to the ultrasonic blade.

15. The articulatable surgical instrument of claim 9, further comprising:

a spring configured to bias the first hollow shaft distally; and a control member configured to create a tension on the spring for overcoming biasing of the spring so as to translate the first hollow shaft proximally.

16. The articulatable surgical instrument of claim 15, wherein the control member is further configured to release the tension on the spring.

17. The articulatable surgical instrument of claim 15, wherein the control member is a reciprocating control member configured to generate reciprocating motion along the longitudinal axis.

* * * * *